US012668670B1

(12) United States Patent
Shi et al.

(10) Patent No.: US 12,668,670 B1
(45) Date of Patent: Jun. 30, 2026

(54) COMPOSITION FOR MANUFACTURE OF HYDROGEL MATERIAL, HYDROGEL MATERIAL, METHOD OF MANUFACTURE OF HYDROGEL MATERIAL, METHOD OF MANUFACTURE OF HYDROGEL STRUCTURE, AND METHOD OF USING DEVICE INCLUDING HYDROGEL MATERIAL

(71) Applicant: City University of Hong Kong, Hong Kong (HK)

(72) Inventors: Peng Shi, Hong Kong (HK); Jin Qu, Hong Kong (HK); Kai Xie, Hong Kong (HK)

(73) Assignee: City University of Hong Kong, Kowloon Tong (HK)

( * ) Notice: Subject to any disclaimer, the term of this patent is extended or adjusted under 35 U.S.C. 154(b) by 784 days.

(21) Appl. No.: 17/804,864

(22) Filed: Jun. 1, 2022

(51) Int. Cl.
| | |
|---|---|
| *C08J 3/075* | (2006.01) |
| *A61N 1/05* | (2006.01) |
| *C08F 2/50* | (2006.01) |
| *C08F 220/38* | (2006.01) |
| *C08J 3/24* | (2006.01) |
| *C08K 5/00* | (2006.01) |
| *C08K 5/46* | (2006.01) |

(52) U.S. Cl.
CPC ............ *C08J 3/075* (2013.01); *A61N 1/0534* (2013.01); *C08F 2/50* (2013.01); *C08F 220/387* (2020.02); *C08J 3/24* (2013.01); *C08K 5/0025* (2013.01); *C08K 5/46* (2013.01); *C08J 2333/14* (2013.01); *C08K 2201/001* (2013.01)

(58) Field of Classification Search
CPC .......... C08J 3/075; C08J 3/24; C08J 2333/14; C08F 220/387; C08F 2/50; A61N 1/0534; C08K 5/0025; C08K 5/46; C08K 2201/001
See application file for complete search history.

(56) References Cited

U.S. PATENT DOCUMENTS 8,374,696 B2 2/2013 Sanchez et al.

FOREIGN PATENT DOCUMENTS

| CN | 113769120 A | * | 12/2021 |
|---|---|---|---|
| CN | 114044920 A | * | 2/2022 |

OTHER PUBLICATIONS

CN114044920A machine translation (Year: 2022).*
Zhang et al., Highly stretchable, self-adhesive, biocompatible, conductive hydrogels as fully polymeric strain sensors, 2020, Journal of Materials Chemistry A, vol. 8 ESI, p. S1-S20 (Year: 2020).*

(Continued)

*Primary Examiner* — Mark Eashoo
*Assistant Examiner* — Caitlin Norine Illing
(74) *Attorney, Agent, or Firm* — Melvin Li; Heslin Rothenberg Farley & Mesiti P.C.

(57) ABSTRACT

One aspect of the present invention is concerned with a composition for the manufacture of a hydrogel material. The composition has N-(3-Sulfopropyl)-N-methacroyloxyethyl-N,N-dimethylammonium betaine (DMAPS) serving as a backbone of the hydrogel material, poly(3,4-ethylenedioxythiophene) polystyrene sulfonate (PEDOT:PSS) serving as a conductive component, and at least one crosslinking agent.

8 Claims, 53 Drawing Sheets

(56) References Cited

OTHER PUBLICATIONS

Zhang et al., Highly stretchable, self-adhesive, biocompatible, conductive hydrogels as fully polymeric strain sensors, 2020, Journal of Materials Chemistry A, vol. 8, p. 20474-20485 (Year: 2020).*

Ding et al., High-Throughput Screening of Self-Healable Polysulfobetaine Hydrogels and their Applications in Flexible Electronics, 2021, Advanced Functional Materials, vol. 31, issue 18, 2100489 (Year: 2021).*

CN113769120A machine translation (Year: 2021).*

Han et al., Improved cell viability for large-scale biofabrication with photo-crosslinkable hydrogel systems through a dual-photoinitiator approach, 2020, Biomaterials Science, vol. 8, p. 450-461 (Year: 2020).*

Mage, et al., Closed-loop control of circulating drug levels in live animals, Nature Biomedical Engineering, vol. 1 May 10, 2017.

Srinivasan, et al., Closed-loop functional optogenetic stimulation, Nature Communications, https://doi.org/10.1038/s41467-018-07721-w, vol. 9, p. 5303 2018.

Armstrong, et al., Closed-loop optogenetic intervention in mice, Nature Protocols, vol. 8, No. 8 2013.

Yu, et al., Glucose-responsive insulin patch for the regulation of blood glucose in mice and minipigs, Nature Biomedical Engineering, https://doi.org/10.1038/s41551-019-0508-y, vol. May 4, 2020.

Li, et al., A Fully Integrated Closed-Loop System Based on Mesoporous Microneedles-Iontophoresis for Diabetes Treatment, Research Article, Advanced Science, vol. 8 2021.

Bouthour, et al., Biomarkers for closed-loop deep brain stimulation in Parkinson disease and beyond, Perspectives, Nature Reviews, Neurology, https://doi.org/10.1038/s41582-019-0166-4, published online Apr. 1, 2019 Apr. 1, 2019.

Merchant, et al., Real-Time Closed-Loop Suppression of Repolarization Alternans Reduces Arrhythmia Susceptibility In Vivo, Circulation: Arrhythmia and Electrophysiology, DOI: 10.1161/CIRCEP.119.008186 Jun. 2020.

Bergey, et al., Long-term treatment with responsive brain stimulation in adults with refractory partial seizures, 2015 American Academy of Neurology 2015.

Vonck, et al., Closing the loop for patients with epilepsy, Nature Reviews, Neurology, vol. 84, pp. 810-817 2015.

Qazi, et al., Wireless optofluidic brain probes for chronic neuropharmacology and photostimulation, Nature Biomedical Engineering, vol. 3, pp. 655-669, https://doi.org/10.1038/S41551-019-0432-1 Aug. 2019.

Mickle, et al., A wireless closed-loop system for optogenetic peripheral neuromodulation, Springer Nature Limited, https://doi.org/10.1038/s41586-018-0823-6, vol. 565 Jan. 17, 2019.

Proctor, et al., Electrophoretic drug delivery for seizure control, Science Advances, Research Article, Health and Medicine Aug. 29, 2018.

Joo, e al., Soft implantable drug delivery device integrated wirelessly with wearable devices to treat fatal seizures, Science Advances, Research Article, Health and Medicine Jan. 1, 2021.

Grosenick, et al., Closed-Loop and Activity-Guided Optogenetic Control, Elsevier Inc., Neuron Review Apr. 8, 2015.

McGlynn, et al., The Future of Neuroscience: Flexible and Wireless Implantable Neural Electronics, Progress Report, Wiley-VCH GmbH, Advanced Science, DOI: 10.1002/advs.202002693 2021.

Qu, et al., Injectable antibacterial conductive hydrogels with dual response to an electric field and pH for localized "smart" drug release, Elsevier, Aca Biomaterialia, https://doi.org/10.1016/j.actbio.2018.03.018 2018.

Hao, et al., Spatiotemporal Magnetocaloric Microenvironment for Guiding the Fate of Biodegradable Polymer Implants, Wiley-VCH GmbH, Advanced Functional Materials 2021.

Ge, et al., Drug Release from Electric-Field-Responsive Nanoparticles, ACS Nano, vol. 6, No. 1, pp. 227-233 2012.

Xie, et al., Organic electrochemical transistor arrays for real-time mapping of evoked neurotransmitter release in vivo, eLife, Research Article, DOI: https://doi.org/10.7554/eLife.50345 2020.

English, et al., Programmable CRISPR-responsive smart materials, Science, Biomaterials, vol. 365, pp. 780-785 Aug. 23, 2019.

Liu, et al., Genetically targeted chemical assembly of functional materials in living cells, tissues, and animals, Research, Biotechnology, Science, vol. 367, pp. 1372-1376 2020.

Liu, et al., Soft and elastic hydrogel-based microelectronics for localized low-voltage neuromodulation, Nature Biomedical Engineering, https://doi.og/10/1038/s41551-018-0335-6, vol. 3, pp. 58-68 Jan. 2019.

Yuk, et al., 3D printing of conducting polymers, Nature Communications, https://doi.org./10.1038/s41467-020-15316-7 2020.

Chen, et al., Stretchable, Injectable, and Self-Healing Conductive Hydrogel Enabled by Multiple Hydrogen Bonding toward Wearable Electronics, Chemistry of Materials, ACS Publications, American Chemical Society, DOI: 10.1021/acs.chemmater.9bo1239, vol. 31, pp. 4553-4563 2019.

Zhao, et al., Injectable antibacterial conductive nanocomposite cryogels with rapid shape recovery for noncompressible hemorrhage and wound healing, Nature Communications, DOI: 10.1038/s41467-018-04998-9 2018.

Sriprachuabwong, et al., Inkjet-printed graphene-PEDOT:PSS modified screen printed carbon electrode for biochemical sensing, Journals of Materials Chemistry, vol. 22, pp. 5478-5485 2012.

Patil, et al., Implantable neurotechnologies: a review of microand nanoelectrodes for neural recording, Med. Biol. Eng, Comput. vol. 54, pp. 23-44, DOI: 10.1007/s11517-015.1430-4 2016.

Akhtar, et al., Characterizing the elastic properties of tissues, Elsevier, Materials Today, vol. 14, No. Mar. 3, 2011.

Yuk, et al., Tough bonding of hydrogels to diverse non-porous surfaces, Nature Materials, vol. 15 Feb. 2016.

Wang, et al., A highly stretchable, transparent, and conductive polymer, Science Advances, Research Article, Applied Sciences and Engineering Mar. 10, 2017.

Stringer, et al., Epileptiform Discharges Induced by Altering Extracellular Potassium and Calcium in the Rat Hippocampal Slice, Experimental Neurology vol. 101, pp. 147-157 1988.

Rutecki, et al., Epileptiform Activity Induced by Changes in Extracellular Potassium in Hippocampus, Journal of Neurophysiology, vol. 54, No. Nov. 5, 1985.

Wenzel, et al., Reliable and Elastic Propagation of Cortical Seizures In Vivo, Cell Press, Cell Reports, vol. 19, pp. 2681-2693 2017.

Nam, et al., Supramolecular Peptide Hydrogel-Based Soft Neural Interface Augments Brain Signals through a Three-Dimensional Electrical Network, ACS Publications, American Chemical Society, https://dx.doi.org/10.1021/acsnono.9b07396, vol. 14, pp. 664-675 2020.

Cook, et al., Anti-seizure therapy with along-term implanted intracerebroventricular delivery system for drug-resistant epilepsy: A first-in-man study, Elsevier, EClinicalMedicine, vol. 22 2020.

Pirozzi, et al., Butyrate prevents valproate-induced liver injury: In vitro and in vivo evidence, FASEB Journal, Research Article, vol. 34, pp. 679-690 2020.

Feig, et al., Mechanically tunable conductive interpenetrating network hydrogels that mimic the elastic moduli of biological tissue, Nature Communications, vol. 9, DOI: 10.1038/s41467-018-05222-4 2018.

Deng, et al., Multifunctional Stimuli-Responsive Hydrogels with Self-Healing, High Conductivity, and Rapid Recovery through Host-Guest Interactions, ACS Publications, Chemistry of Materials, vol. 30, pp. 1729-1742, DOI: 10.1021/acs.chemmater.8b00008 2018.

Shi, et al., Conductive "Smart" Hybrid Hydrogels with PNIPAM and Nanostructured Conductive Polymers, Advanced Functional Materials, vol. 25, pp. 1219-1225, DOI: 10.1002/adfm.201404247 2015.

Zhao, et al., Soft Materials by Design: Unconventional Polymer Networks Give Extreme Properties, ACS Publications, Chemical Reviews, vol. 121, pp. 4309-4372, https://doi.org/10.1021/acs.chemrev.)c01088 2021.

Jonsson, et al., Therapy using implanted organic bioelectronics, Sci. Adv., Research Article, Neuroscience' May 8, 2015.

(56)     References Cited

OTHER PUBLICATIONS

Amorini, et al., Electrically Controlled "Sponge Effect" of PEDOT:PSS Governs Membrane Potential and Cellular Growth, ACS Publications, Applied Materials & Interfaces, vol. 9, pp. 6679-6689, DOI: 10.1021/acsami.6b12480 2017.

Park, et al., Three-dimensional, multifunctional neural interfaces for cortical spheroids and engineered assembloids, Science Advances, Research Article, Applied Sciences and Engineering Mar. 17, 2021.

Kim, et al., Soft subdermal implant capable of wireless battery charging and programmable controls for applications in optogenetics, Nature Communications, https://doi.org/10.1038/s41467-020-20803-y 2021.

Won, et al., Emerging Modalities and Implantable Technologies for Neuromodulation, Elsevier Inc., Leading Edge Review Apr. 2, 2020.

Li, et al., Stimuli-Responsive Drug- Delivery Systems Based on Supramolecular Nanovalves, Elsevier Inc., Cell Press Reviews, Matter, vol. 1, pp. 345-368 Aug. 7, 2019.

Berenyi, et al., Closed-Loop Control of Epilepsy by Transcranial Electrical Stimulation, Science, vol. 337 Aug. 10, 2012.

Proctor, et al., Electrophoretic drug delivery for seizure control, Science Advances, Research Article, Health and Medicine, vol. 4 Aug. 29, 2018.

Joo, et al., Soft implantable drug delivery device integrated wirelessly with wearable devices to treat fatal seizures, Science Advances, Research Article, Health and Medicine, vol. 7 Jan. 1, 2021.

Zeglio, et al., Conjugated Polymers for Assessing and Controlling Biological Functions, WILEY-VCH Verlag GmbH & Co., Advanced Materials, Review, DOI: 10.1002/adma.201806712, vol. 31 2019.

* cited by examiner a

PEDOT:PSS solution → DMAPS → PEDOT:PSS hydrogel → UV exposure I2959 → DMA/PEDOTS-IPN hydrogel PSS  PEDOT  PEDOT:PSS micelle  DMAPS  PF127-DA  MBAA 1 cm  100 um  15 um  5 um Control 2 weeks 4 weeks Sham control 2 weeks     4 weeks PF127 → Acryloyl chloride / RT 24 h → PF127-DA

FIG. 7a

DMAPS

+

PF127-DA

+

MBAA

→ UV exposure / I2959 → DMA/PEDOTS-IPN

COMPOSITION FOR MANUFACTURE OF HYDROGEL MATERIAL, HYDROGEL MATERIAL, METHOD OF MANUFACTURE OF HYDROGEL MATERIAL, METHOD OF MANUFACTURE OF HYDROGEL STRUCTURE, AND METHOD OF USING DEVICE INCLUDING HYDROGEL MATERIAL

FIELD OF THE INVENTION

The present invention is concerned with a composition for manufacture of a hydrogel material, a hydrogel material, a method of manufacture of hydrogel material, a method of manufacture of hydrogel structure, and a method of using a device including a hydrogel material.

BACKGROUND OF THE INVENTION

There are a variety of ways to administer a therapeutic agent to a patient in need thereof. Further, there are a variety of ways to detect bio-signs of a patient. Nevertheless, there are very few, if any all, single means which can serve to do both, or both simultaneously.

There are also a variety of medical conditions or illnesses which require constant monitoring. In response to results from the monitoring, one or more actions, e.g. administration of a therapeutical agent, would be needed. There have been conventional systems which would address the tasks of monitoring and administration. For instance, in the context of a hospital setting, multiple apparatus would be needed to monitor different physiological parameters. Then when one or more such physiological fallen outside of an acceptable range indicative of an abnormality are detected, a medical attendant, e.g. a medical attendant, a nurse or a doctor on duty, would need to respond to address the abnormality. This process is often far from ideal because, for example, if/when there are multiple patients who require unexpected attention at the same time, the medical staff on duty might not be able to attend to the patients and delay of treatment would cause further adverse medical conditions or even liability.

Another problem with managing a medical condition of a patient is that, conventionally, the focus is to address the medical condition when adverse or acute symptoms have already developed. This is far from ideal because once the adverse or acute symptoms have developed, the difficulties to then counter the symptoms would be much higher compared to if the medical condition could be addressed before any significant or severe symptoms have kicked in.

The aforementioned conventional systems can be understood as an open loop system in that the steps of monitoring or detection of a patient's conditions is not linked, or at least not directly, electronically or real-time linked, to any treatment provided in response. Also due to the present of the element of a human (medical staff) which is required to take action, problems due to delay, inefficiency, passivity, management, etc. inevitably tend to arise.

The present invention seeks to address at least the aforementioned problems, or at least to provide alternatives to the public, by providing a composition for manufacture of a hydrogel material, a hydrogel material, a method of manufacture of hydrogel material, a method of manufacture of hydrogel structure, and a method of using a device including a hydrogel material, which are important elements for used in building devices and systems for medical monitoring and therapeutic administrative purposes.

SUMMARY OF THE INVENTION

According to a first aspect of the present invention, there is provided a composition for the manufacture of a hydrogel material, comprising N-(3-Sulfopropyl)-N-methacroyloxy-ethyl-N,N-dimethylammonium betaine (DMAPS) serving as a backbone of the hydrogel material, poly(3,4-ethylene-dioxythiophene) polystyrene sulfonate (PEDOT:PSS) serving as a conductive component, and at least one crosslinking agent.

Preferably, the crosslinking agent may be or may include a compound provided with acryloyl groups as terminal groups, and wherein the crosslinking agent may be selected from the group consisting of N, N'-Methylenebisacrylamide (MBA), diacrylate functionalized PF127, diacrylate functionalized PEG, diacrylate functionalized hyaluronic acid, and diacrylate functionalized dextran.

Suitably, the composition may comprise a photo-initiator or a photo-initiator auxiliary element, or a catalyst, for facilitating crosslinking of the DMAPS and the PEDOT:PSS in the hydrogel material. In an embodiment, the photo-initiator may be or may include 2-hydroxy-4'-(2-hydroxy-ethoxy)-2-methylpropiophenone (Irgacure 2959). The photo-initiator auxiliary element may be selected from the group consisting of I2959, LAP, ITX, 2-(4-methylbenzyl)-2-(dimethyamino)-1-(4-morpholinophenyl)butan-1-one (Irgacure 379), phenylbis(2,4,6-trimethylbenzoyl)phosphine oxide (Irgacure 819), 2-methyl-4'-(methylthio)-2-morpholinopropiophenone (Irgacure 907) and TPO. The catalyst may be ammonium persulfate and N,N,N',N'-tetramethyl-ethylenediamine.

According to a second aspect of the present invention, there is provided a hydrogel material comprising an inter-penetrating structure of N-(3-Sulfopropyl)-N-methacroy-loxyethyl-N,N-dimethylammonium betaine (DMAPS) serving as a backbone of the hydrogel material, poly(3,4-ethylenedioxythiophene) polystyrene sulfonate (PEDOT:PSS) serving as a conductive component, and at least one crosslinking agent linking the DMAPS and the PEDOT:PSS together in the hydrogel material forming a network of polymerized PEDOT:PSS and PEDOT:PSS (DMA/PE-DOTS).

The crosslinking agent may be or may be include a compound provided with acryloyl groups as terminal groups, and wherein the crosslinking agent is selected from the group consisting of N, N'-Methylenebisacrylamide (MBA), diacrylate functionalized poly(ethylene glycol)-b-poly(propylene glycol)-b-poly(ethylene glycol) (PF127), diacrylate functionalized PEG, diacrylate functionalized hyaluronic acid, and diacrylate functionalized dextran. The content of the DMAPS in the hydrogel material may be 5-60 wt %, and the content of the PEDOT:PSS in the hydrogel material is 0.01-20 wt %. The hydrogel material may comprise a photo-initiator or a photo-initiator auxiliary element, or a catalyst, for assisting the photo-crosslinking of the DMAPS and the PEDOT:PSS by the crosslinking agent. The photo-initiator may be or may include 2-hydroxy-4'-(2-hydroxyethoxy)-2-methylpropiophenone (Irgacure 2959). The photo-initiator auxiliary element may be selected from the group consisting of I2959, LAP, ITX, 2-(4-methylben-zyl)-2-(dimethyamino)-1-(4-morpholinophenyl)butan-1-one (Irgacure 3791, phenylbis(2,4,6-trimethylbenzoyl)phos-phine oxide (Irgacure 819), 2-methyl-4'-(methylthio)-2- morpholinopropiophenone (Irgacure 907) and TPO. The catalyst may be ammonium persulfate and N,N,N',N'-te-tramethylethylenediamine.

According to a third aspect of the present invention, there is provided a method of manufacture of a hydrogel material, comprising the steps of mixing a first homogenous solution with a second homogenous solution to firm a first mixture, —adding a crosslinking agent to the first mixture thus forming a second mixture, and effecting linking of the PEDOT:PSS with the DMAPS in the second mixture for forming the hydrogel material, wherein the first homogenous solution is formed from dissolving a conductive component of poly(3,4-ethylenedioxythiophene) polystyrene sulfonate (PEDOT:PSS), the second homogeneous solution is formed from dissolving N-(3-Sulfopropyl)-N-methacroyloxyethyl-N,N-dimethylammonium betaine (DMAPS), the PEDOT:PSS acts as a conductive component and the DMAPS acts as a backbone in the hydrogel material, the content of the DMAPS in the hydrogel material is 5-60 wt %, and the content of the PEDOT:PSS in the hydrogel material is 0.01-20 wt %, Preferably, the method comprise a step of effecting photo-crosslinking of the PEDOT:PSS with the DMAPS by the cross-linking agent in the presence of a photo-initiator or photo-initiator auxiliary element. The photo-initiator may be the photo-initiator or may include Irgacure 2959, and the photo-initiator auxiliary element is selected from the group consisting of I2959, LAP, ITX, Irgacure 379, Irgacure 819, Irgacure 907 and TPO. The method may comprise a step of effecting free-radical polymerization of the PEDOT:PSS with the DMAPS by the cross-linking agent in the presence of a catalyst.

The catalyst may be ammonium persulfate and N,N,N', N'-tetramethylethylenediamine. The A method crosslinking agent may be or may include a compound provided with acryloyl groups as terminal groups, wherein the crosslinking agent may be selected from the group consisting of N, N'-Methylenebisacrylamide (MBA), diacrylate functionalized PF127, diacrylate functionalized PEG, diacrylate functionalized hyaluronic acid, and diacrylate functionalized dextran. The first homogeneous solution may be formed from dissolving the PEDOT:PSS to a physiological solution selected from the group consisting of phosphate buffered saline (PBS), distilled water, diethyl pyrocarbonate water (DEPC water), diethyl pyrocarbonate phosphate buffered saline (DEPC PBS). The PEDOT:PSS may have a content from 0.01% wt to 20% wt in the hydrogel material. The second homogeneous solution may be formed from dissolving the DMAPS to a physiological solution selected from the group consisting of phosphate buffered saline (PBS), distilled water, diethyl pyrocarbonate water (DEPC water), diethyl pyrocarbonate phosphate buffered saline (DEPC PBS). The DMAPS may have a content from 5% wt to 60% wt in the hydrogel material.

Suitably, the crosslinking agent may have a content from 0.01% wt to 50% wt in the second mixture.

In one embodiment, the duration of time of the photo-crosslinking may range from 1 min to 60 min. The duration of time of the free radical polymerization time may be from 1 min to 24 hours.

According to a fourth aspect of the present invention, there is provided a method of manufacture of a hydrogel structure comprising a method of manufacture of a hydrogel material as described above. The method may comprise a step of injection molding, case molding, 3D-printing or photolithographing of the hydrogel material and thus forming the hydrogel structure.

According to a fifth aspect of the present invention, there is provided a method of using a device including a hydrogel material as described above, wherein the device may be configured to engage with a body of a subject in need thereof, and may be configured to detect physiological bioelectronic signals therefrom.

Preferably, the device may be configured to engage with the heart, spinal cord, skin, muscle or brain of the subject. The hydrogel material may be fabricated as electrodes for real-time detection of the physiological bioelectronic signals. The device may be configured as miniaturized implantable electrodes acting a probe for providing deep brain stimulation for the treatment of Parkinson's disease, essential tremors, heart failures or spinal cord injuries. The device may be configured for use as neural interfaces for robotic prostheses.

Suitably, the device may be preloaded with a therapeutic agent selected from the group of DNAs, RNAs, chemical compounds, liposome, nanoparticles, micelle and protein for administration to the subject.

In an embodiment, the device may be configured to, on receiving an external electrical stimulus, release the preloaded agent.

The external electrical stimulus to the device may be DC voltage or DC current.

The method may comprise a step of controlling the rate of release, amount of release, duration of release and/or status of release of the pre-loaded agent by controlling the DC voltage or DC current.

In one embodiment, the preloaded agent may be charged molecules, and the method may comprise a step of releasing the preloaded molecules from the hydrogel material into biological membrane of cells of the body by electro-osmosis.

Suitably, the method may comprise a step of supplying power from an external power source to the device, wherein the external power source is a source meter, wave generator, potable power, flexible battery or flexible capacitor.

Advantageously, the hydrogel material may be configured as a biocompatible tissue scaffold for tissue repairing.

In one embodiment, the hydrogel material may be applied on the brain, spinal cord, cardiac muscle or skeletal muscle for treatment or repair.

BRIEF DESCRIPTION TO THE DRAWINGS

Some embodiments of the present invention will now be explained, with reference to the accompanied drawings, in which:

FIG. 1 is a schematic diagram illustrating the use of an embodiment of an electronic device in a closed-loop methodology in accordance with the present invention for monitoring conditions of a subject (e.g. patient) and to provide treatment to the subject in response to results from the monitoring.

FIGS. 2*a* to 2 *h* are representations, photographic images and graphs illustrating formation of a hydrogel material for use in making the electronic device, structure of the hydrogel material and various characteristics of the hydrogel material.

FIGS. 3*a* to 3*i* are representations, photographic images and graphs showing embodiments of a fabrication of an electronic device, the electronic device as fabricated according the present invention, and various characteristics of the electronic device fabricated.

FIGS. 4*a* to 4*i* are graphs and schematic diagrams showing various characteristics of the electronic device.

FIGS. 7a to 7c illustrate an embodiment of a fabrication of a hydrogel material according to the present invention.

Figure 12:
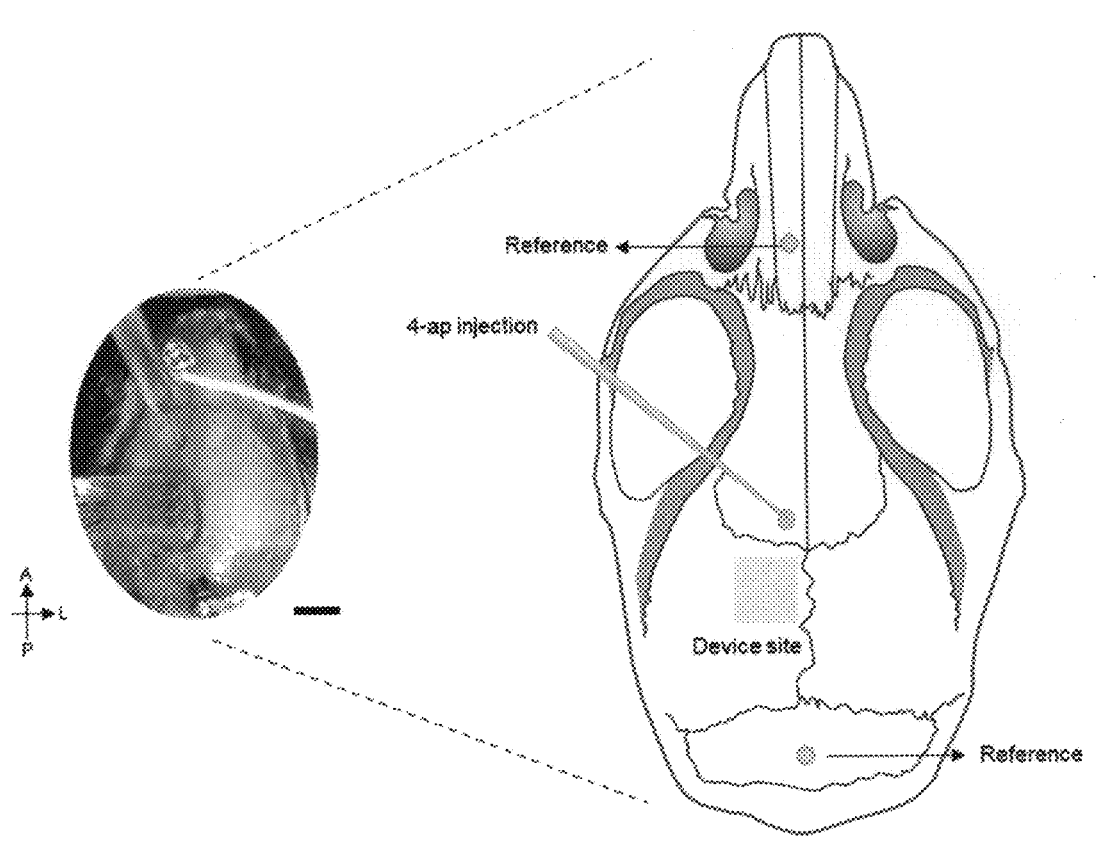

FIG. 12 includes a photographic image and a schematic diagram corresponding thereto illustrating the implantation of an electronic device to the brain of a mouse for monitoring signals from the mouse brain and for providing treatment to the mouse in response to signals detected.

FIGS. 13a to 13e are graphs comparing the detection of signals from a normal mouse (FIG. 13a) and an epileptic mouse (FIG. 13b) under different conditions.

Figure 14:
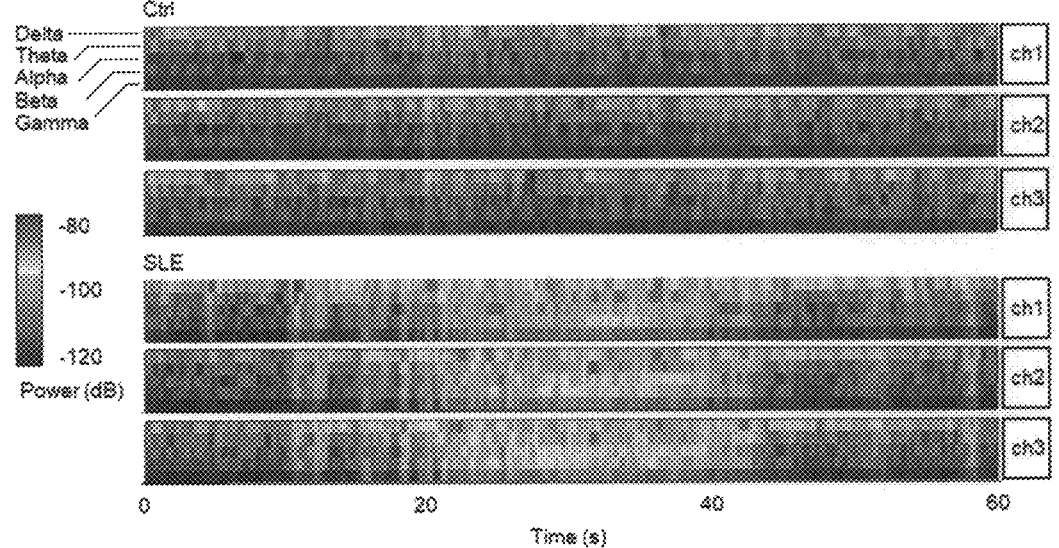

FIG. 14 is a representation showing an analysis of spectrum power of neural oscillation frequency for signals acquired from normal (control) and epileptic (SLE) animals.

Figure 15:
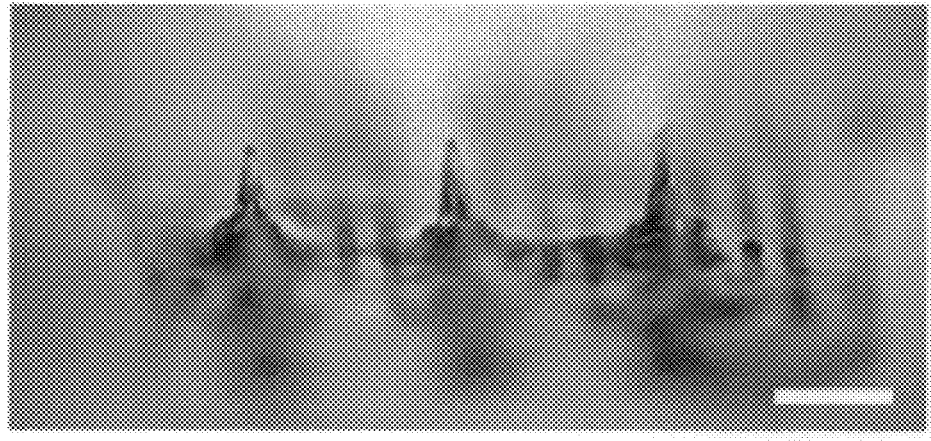

FIG. 15 is a photogram showing an embodiment of an a μNTron device applied on the brian of a mouse brain. (Scale bar, 500 μm FIGS).

Figure 16A:
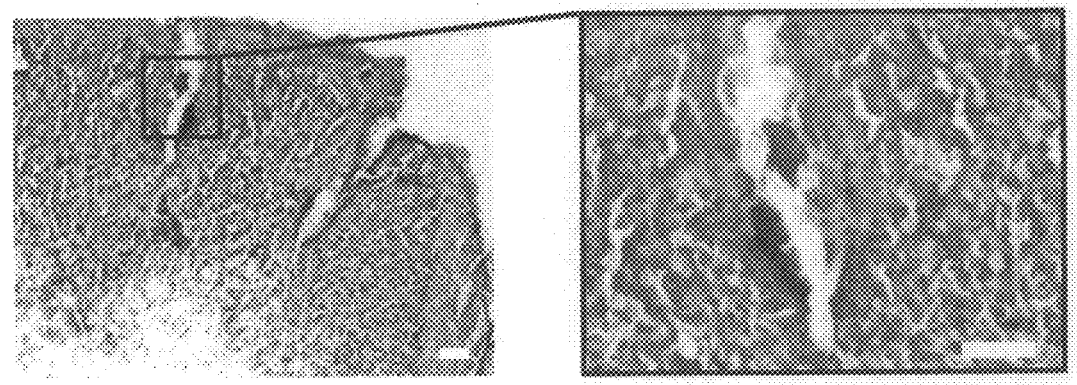
Figure 16B:
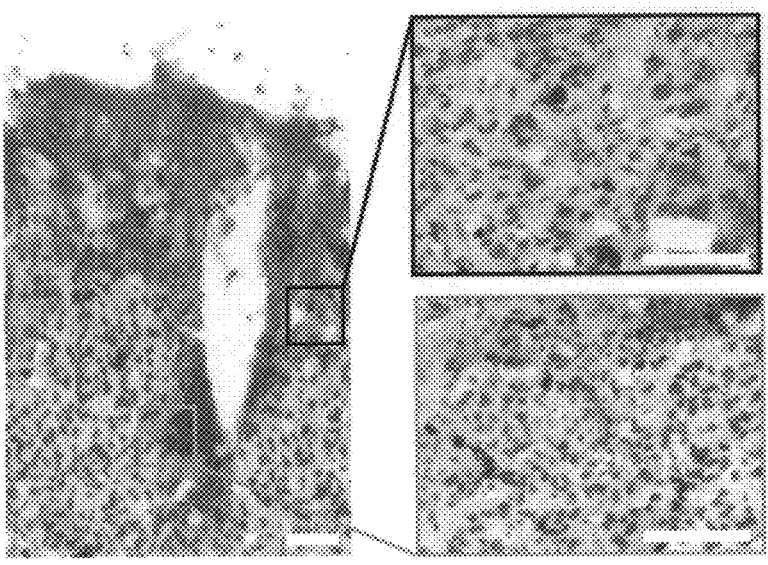

FIGS. 16a-16b are photographic representations illustrating histology staining for H&E (FIG. 16a) and Nissel blue (FIG. 16b) in the coronal section brain tissues, and showing the implantation of an electronic device.

Figure 17A:
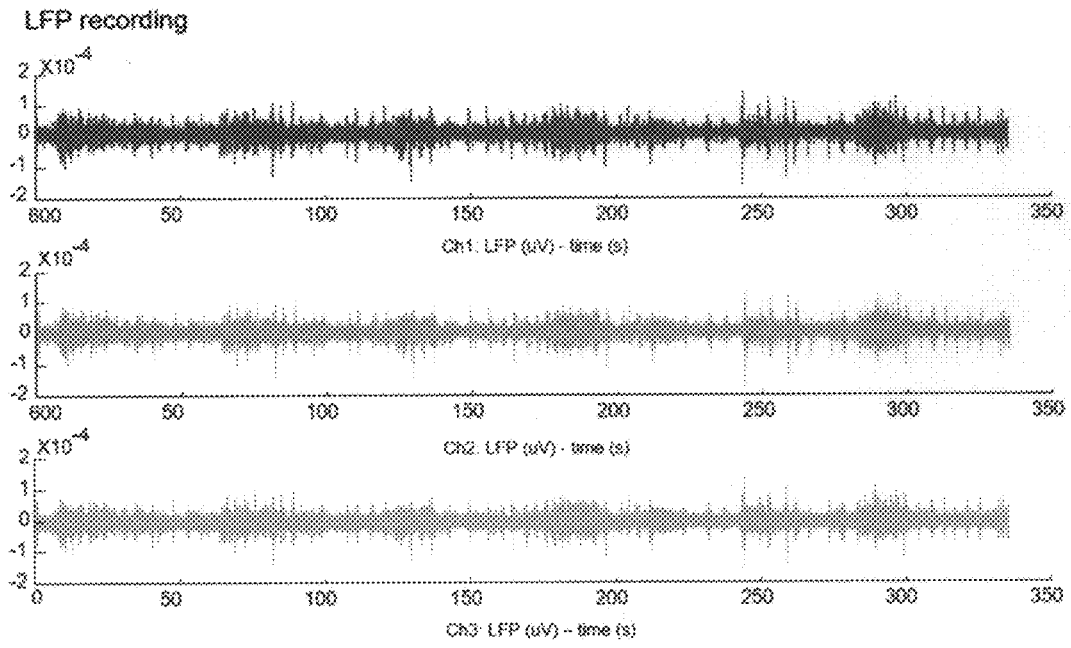
Figure 17B:
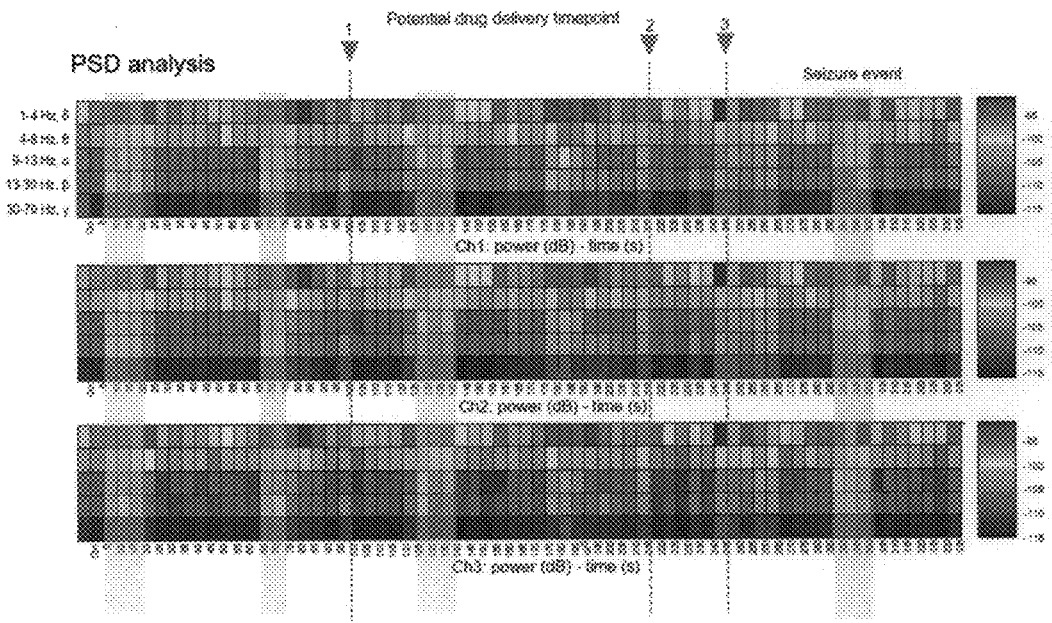

FIGS. 17a to 17b are representations showing real-time local field potential (LEP) recording and frequency analysis.

Figure 18A:
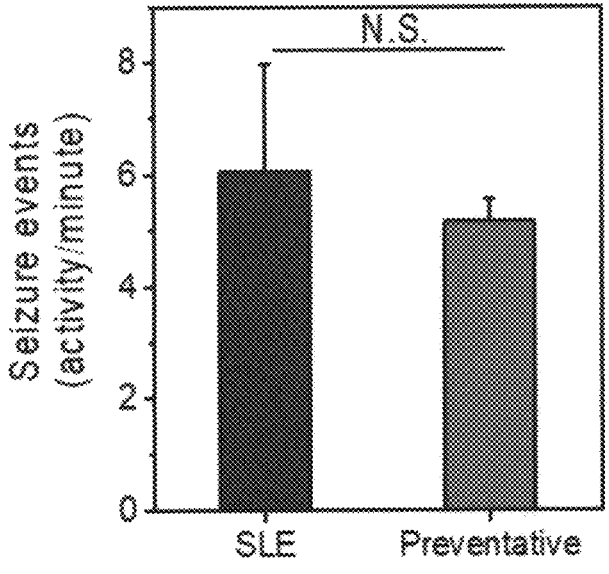

FIG. 18a is a graph showing the quantification of SLE events in epileptic animals without any treatment or being treated with a blank device (no GABA) (n=6).

Figure 18B:
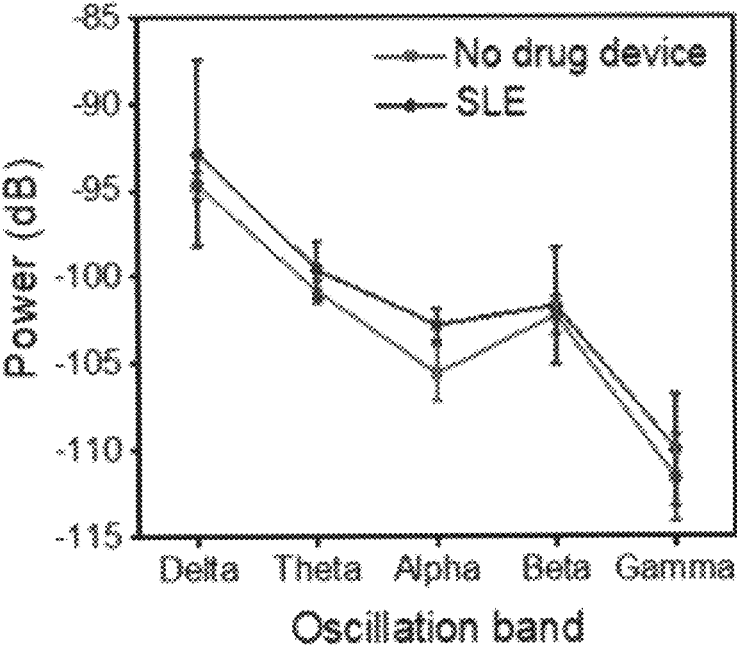

FIG. 18b is a graph showing a power spectrum analysis of the LFP recordings in epileptic animals without any treatment or being treated with a blank device (no GABA) (n=6).

Figure 18C:
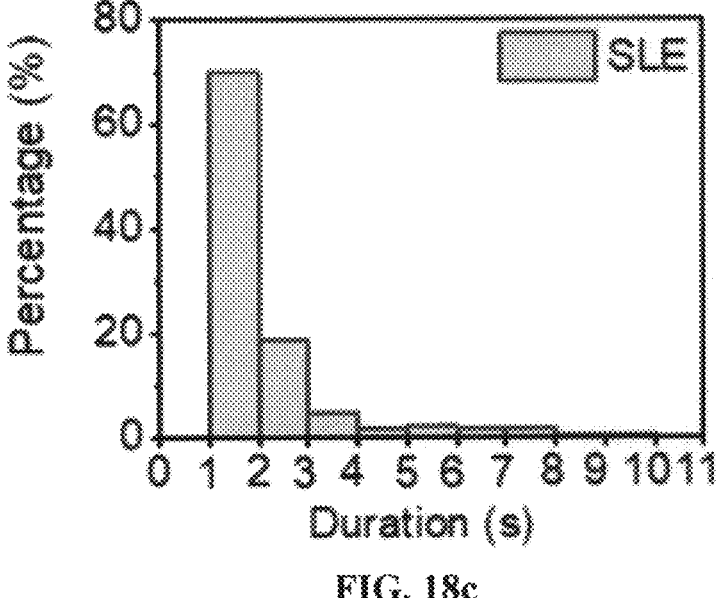
Figure 18D:
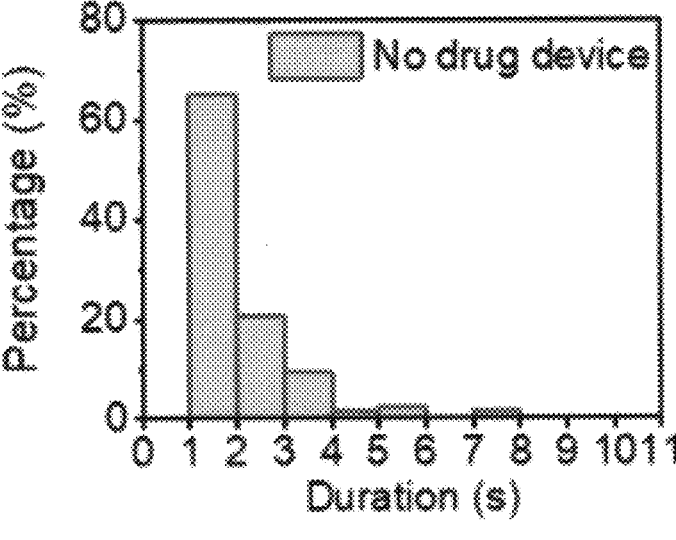

FIGS. 18c-d are graphs showing the analysis of the duration SLE activity in untreated (FIG. 18c) and the blank (FIG. 18d) devices.

Figure 19:
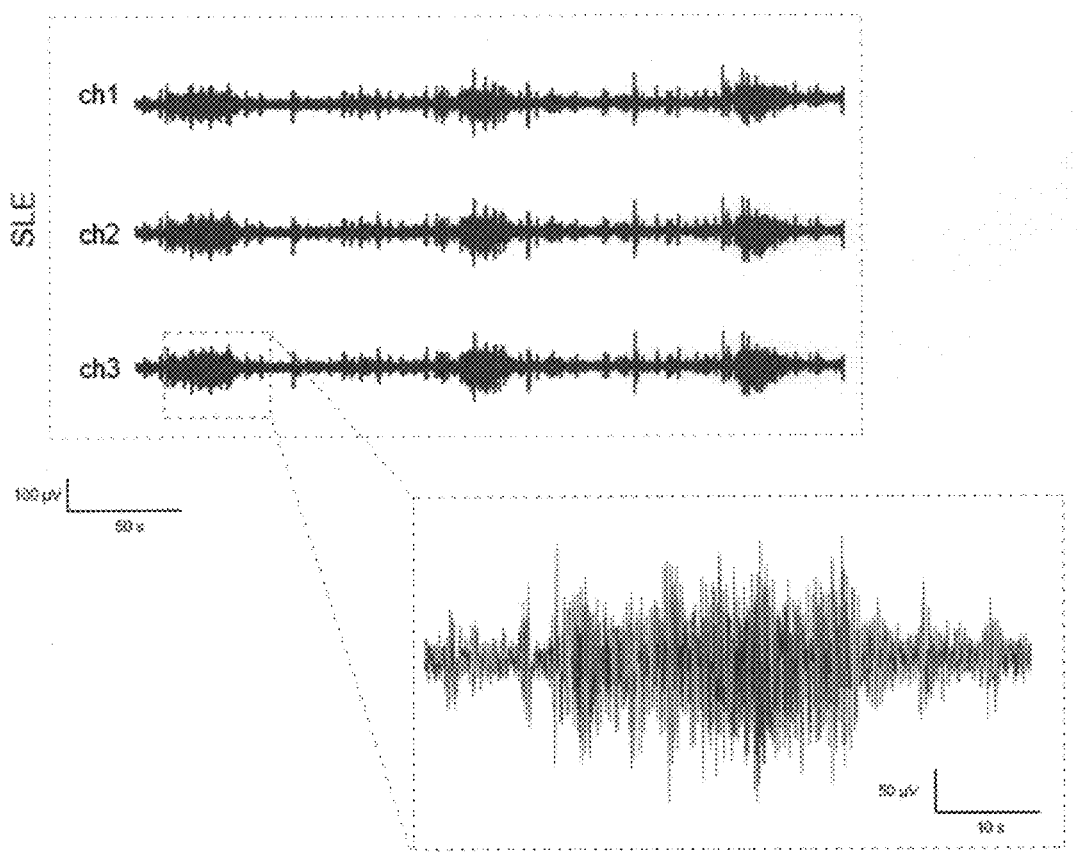

FIG. 19 is a representation of multiple-channel LFP recording of the seizure signal by using the μNTron electrodes.

Figure 20:
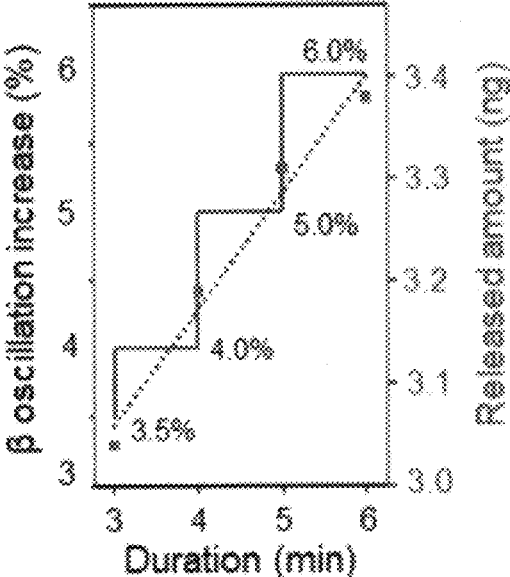

FIG. 20 is a graph showing adaptive dosing control by varying voltage stimulation (200 mV, 3~6 minutes) based on the change of β oscillation amplitude to trigger drug release from individual electrodes of a μNTron device.

DETAILED DESCRIPTION OF PREFERRED EMBODIMENTS OF THE INVENTION

Hydrogel Composition, Hydrogel Material, Method of Manufacture of Hydrogel Material, Method of Manufacture of Hydrogel Structure One component of the present invention is to provide a composition for the manufacture of a hydrogel material. The hydrogel material has two core ingredients, namely N-(3-

Sulfopropyl)-N-methacroyloxyethyl-N,N-dimethylammonium betaine (DMAPS) which mainly serves as a backbone of the hydrogel material, and poly(3,4-ethylenedioxythiophene) polystyrene sulfonate (PEDOT:PSS) which mainly serves as a conductive component in the hydrogel material. In order for the two ingredients to link together, at least one crosslinking agent is provided. Studies and experiments leading to the present invention indicate that suitable crosslinking agents are com pounds provided with acryloyl groups as terminal groups. In specific embodiments, the crosslinking agents are selected from the group consisting of N, N'-Methylenebisacrylamide (MBA), diacrylate functionalized PF127, diacrylate functionalized PEG, diacrylate functionalized hyaluronic acid, and diacrylate functionalized dextran. In addition, external polymers can be added into this system as the supplement reagents to improve the mechanical strength of the hydrogel, including sodium alginate, chitosan, gelatin, hyaluronic acid, etc.

In an embodiment, the hydrogel material composition may also comprise a photo-initiator or a photo-initiator auxiliary element, or a catalyst, for facilitating crosslinking of the DMAPS and the PEDOT:PSS in the hydrogel material. In specific embodiments, the photo-initiator is or includes Irgacure 2959, the photo-initiator auxiliary element is selected from the group consisting of I2959, LAP, ITX, Irgacure 379, Irgacure 819, Irgacure 907 and TPO, and the catalyst is ammonium persulfate and N,N,N',N'-tetramethyl ethylenediamine.

When the DMAPS and the PEDOT:PSS are linked together in the hydrogel material, a network of polymerized PEDOT:PSS and PEDOT:PSS (DMA/PEDOTS) is formed. Studies and experiments illustrate that the workable content of the DMAPS in the hydrogel material is 5-60 wt %, and the workable content of the PEDOT:PSS in the hydrogel material is 0.01-20 wt %.

In an embodiment of a method of manufacture of a hydrogel material of the present invention, there is provided the steps of mixing a first homogenous solution with a second homogenous solution to form a first mixture, adding a crosslinking agent to the first mixture thus forming a second mixture, and effecting linking of the PEDOT:PSS with the DMAPS in the second mixture for forming the hydrogel material. The first homogenous solution is formed from dissolving a conductive component of poly(3,4-ethylenedioxythiophene) polystyrene sulfonate (PEDOT:PSS), the second homogeneous solution is formed from dissolving N-(3-Sulfopropyl)-N-methacroyloxyethyl-N,N-dimethylammonium betaine (DMAPS), and the PEDOT:PSS acts as a conductive component and the DMAPS acts as a backbone in the hydrogel material.

One embodiment of the method includes a step of effecting photo-crosslinking of the PEDOT:PSS with the DMAPS by the cross-linking agent in the presence of a photo-initiator or photo-initiator auxiliary element. The photo-initiator is or includes Irgacure 2959, and the photo-initiator auxiliary element is selected from the group consisting of I2959, LAP, ITX, Irgacure 379, Irgacure 819, Irgacure 907 and TPO.

In an alternative embodiment, the method comprises a step of effecting free-radical polymerization of the PEDOT: PSS with the DMAPS by the cross-linking agent in the presence of a catalyst.

The first homogeneous solution is formed from dissolving the PEDOT:PSS to a physiological solution selected from the group consisting of phosphate buffered saline (PBS), distilled water, diethyl pyrocarbonate water (DEPC water), diethyl pyrocarbonate phosphate buffered saline (DEPC PBS). The second homogeneous solution is formed from dissolving the DMAPS to a physiological solution selected from the group consisting of phosphate buffered saline (PBS), distilled water, diethyl pyrocarbonate water (DEPC water), diethyl pyrocarbonate phosphate buffered saline (DEPC PBS). In preferred embodiments, the crosslinking agent has a content from 0.01% wt to 50% wt in the second mixture, the duration of time of the photo-crosslinking ranges from 1 min to 60 min, and the duration of time of the free radical polymerization time can be from 1 min to 24 hours.

In an embodiment, the workable content of sodium alginate or chitosan or gelatin or hyaluronic acid in the hydrogel is 0-60 wt %. They can be dissolved in physiological solution selected from the group consisting of phosphate buffered saline (PBS), distilled water, diethyl pyrocarbonate water (DEPC water), diethyl pyrocarbonate phosphate buffered saline (DEPC PBS). And these supplements are dissolved with DMAPS solution together.

The afore-illustrated hydrogel composition and hydrogel material can be used to fabricate a hydrogel structure by way of, for example, injection molding, case molding, 3D-printing or photolithographing of the hydrogel material and thus forming the hydrogel structure.

The afore-illustrated hydrogel structure can be used to fabricate a device configured to engage with a body of a subject in need thereof, and is configured to detect physiological bioelectronic signals therefrom. The device can be configured to engage with the heart, spinal cord, skin, muscle or brain of the subject. The hydrogel material can be fabricated as electrodes for real-time detection of the physiological bioelectronic signals. The device can be configured as miniaturized implantable electrodes acting a probe for providing deep brain stimulation for the treatment of Parkinson's disease, essential tremors, heart failures or spinal cord injuries. The device can be configured for use as neural interfaces for robotic prostheses. In preferred embodiments, the device is preloaded with a therapeutic agent selected from the group of DNAs, RNAs, chemical compounds, liposome, nanoparticles, micelle and protein for administration to the subject. The device is configured to, on receiving an external electrical stimulus, release the preloaded agent. The external electrical stimulus to the device is a DC voltage or DC current.

Preferred embodiments of a method of using the device include the steps of controlling the rate of release, amount of release, duration of release and/or status of release of the pre-loaded agent by controlling the DC voltage or DC current, and supplying power from an external power source to the device, wherein the external power source is a source meter, wave generator, potable power, flexible battery or flexible capacitor. The preloaded agent are charged molecules, the preloaded molecules from the hydrogel material are releasable into biological membrane of cells of the body by electro-osmosis. The hydrogel material is configured as a biocompatible tissue scaffold for tissue repairing. The hydrogel material can be applied on the brain, spinal cord, cardiac muscle or skeletal muscle for treatment or repair.

Electronic Device and System for Detection of Electrophysiological Signals from and/or provision of stimuli to a subject in need of treatment, and Method of Fabricating the Electronic One focus of the present invention is to provide a closed loop system for attending to a patient's needs. Specifically, the closed loop system ties both the areas of monitoring the conditions of a patient and providing pre-determined treatment together electronically. The closed loop system features a dose-adaptive and time-sensitive modulation of pathological activities which leads to a promising forefront of therapy regimes. The closed loop system can provide greater effectiveness. In the context in which a therapeutic agent is needed, the closed loop system can achieve the greater effectiveness with a minimal dose of the therapeutical agent.

Compared to the closed loop system of the present invention, conventional techniques based on the integration of different components in one device are not compatible, or at least not fully compatible or electronically communicable, with each other, partly due to the lack of multifunctionality. For example, conventional techniques often cause compromised temporospatial resolution of in situ recording and molecular delivery.

In one aspect of the present invention, there is provided an organic multifunctional microneedle electronics ($\mu$NTron) developed to address limitations of the conventional techniques. Specifically, there is provided an interpenetrating network structure of an electroactive hydrogel. The hydrogel needles are pre-loaded with therapeutical molecules which can be released, e.g. by electro-osmosis upon low voltage applied. The organic multifunctional microneedle electronics can thus be understood to include addressable hydrogel microneedles which allow for multiplexed electrophysiological recording and selective voltage-driven molecular delivery at the same time. Accordingly, the organic multifunctional microneedle electronics allows and enables localized and efficient feedback-based intervention. Experiments were conducted using a mouse seizure model. It is demonstrated that the organic multifunctional microneedle electronics empowers a preventative disruption of propagated seizure based on early seizure signals and adaptive dose, and further inhibits the full seizure outburst. The organic multifunctional microneedle electronics opens a door for closed loop medical systems as discussed above.

An electroactive hydrogel with brain tissue-like mechanical property is fabricated into a novel bioelectrode array for closed-loop neurotreatment. The biointerface composes of multiple channels for electrophysiological signal record and pharmacological intervention synergistic. When the electrode detects unusual neural spiking signals, drug molecules preloaded in hydrogel electrodes are released intelligently to intervene as feedback in pathological conditions. The effect of drug feedback therapeutic is evaluated and controlled by real-time neural signals until the symptoms vanish and the epilepsy animal recover to a normal state. This hydrogel electrode array integrated neurostimulation with pharmacological intervention in a highly accurate time and spatial manner to achieve superior efficacy.

The present invention of providing a closed loop system of providing intelligent medical services bridges the gap of combining the utilizing of organic electronics and stimulus-responsive materials.

Experiments

Figure 1:
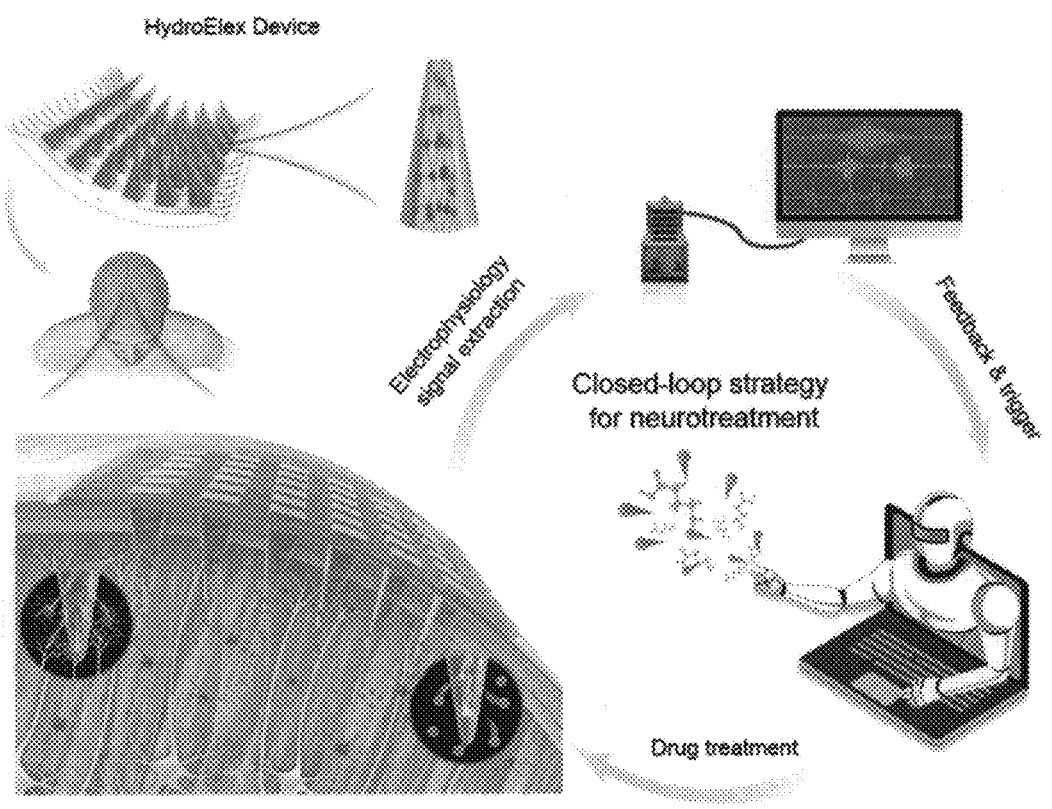

The present invention has been developed to provide a flexible organic electronic device for intelligent disease monitoring and closed-loop anti-seizure treatment in epileptic animals. The core of the device was made of conductive hydrogels and was fabricated as a flexible array of microneedle electronics ($\mu$NTron), which can be closely interfaced to curved brain tissues to continuously perform electrophysiology recording. FIG. 1 are schematic diagram providing an overview of the closed-loop strategy empowered by organic multifunctional $\mu$NTron. FIG. 1 shows the $\mu$NTron with an array of addressable microneedles loaded with biomolecules, which can be applied for multiplexed electrophysiological recording and voltage-driven molecular delivery; μNTron applied for the closed-loop intervention strategy can be contacted with the cortex; and FIG. 1 illustrates that the closed-loop strategy can record LFP signals and deliver pre-loaded molecules to inhibit the onset of seizure. Electrophysiology signals indicative or predictive of onset of seizure signal facilitates the optimized timing and dose of delivery of a therapeutic agent. Pre-emptive administration, for example, of the therapeutic agent can achieve an optimal outcome compared to the traditional methods which deliver treatment only after a full outburst of symptoms. The recorded neural signal then acts as feedback to trigger a voltage-driven drug release in detected pathological conditions, where seizures are preluded by a real-time cortical spiking conditions analysis based the electrophysiological conditions. Specifically, the hydrogel material or substrate synthesized using the N-(3-Sulfopropyl)-N-methacryloxyethyl-N,N-dimethylammonium betaine (DMAPS) as a backbone, to which conductive PEDOT:PSS was electrostatically linked, render an interpenetrating network (IPN) structure for improved conductivity and mechanical strength. As a proof-of-concept, experiments were conducted to show that, when implanted into 4-Aminopyridine (4-ap) induced epileptic animals, the μNtron device was used to implement a closed-loop feedback strategy for preventative anti-seizure management. With the help of real-time surveillance of anomalous neural activity, the outburst of seizure is well-controlled by this hydrogel-based μNTron device in a dose-adaptive manner, decreasing all the duration, power, and frequency of seizure-like events (SLE), and thereby to prevent seizure progression effectively. It is thus demonstrated that the single-component, multifunctional μNTron device opens new path towards in vivo closed-loop neuro-treatment by employing organic electronics and artificial intelligence. Such a strategy can be further extended for use in precise and autonomous pharmaceutical administration in a broad range of chronic diseases or medical conditions to achieve smart health management.

The μNTron device discussed above was implanted on, for example, the cortex of mouse to detect local field potential (which a kind of neural signal). In the context of an experiment on the mouse, the mouse was anesthetized by intraperitoneal (I.P.) injection of pentobarbital (40 mg/kg, Ceva Santé Animal). Another I.P. injection of atropine (3.25 mg/kg) was performed to suppress bronchial secretion that may cause suffocation. After the mouse was mounted on a stereotaxic apparatus (Narishige), an incision was made on the scalp to expose the skull. A square craniotomy window (3×3 mm$^2$) was created at cortical region (window center at −2.2 mm A/P and 1.5 mm M/L) to allow the placement of a μNTron device. A small access hole (0.5 mm diameter, 0.8 mm A/P and 0.2 mm M/L) was drilled on the skull to insert a glass micropipette for 4-ap injection. A metal screw was secured on the skull around cerebellum region to serve as the ground electrode for both electrophysiological recording and voltage-driven drug releasing. Throughout an experiment, a heating pad was placed beneath the animal to maintain a stable temperature at 37° C.

The μNTron device was connected to a flexible flat cables (FFC) socket soldered on a customized circuit board for convenient connection to a preamplifier (TDT). The LFP signal was recorded using Synapse software (TDT). During recording, the sampling frequency was set at 1017 Hz, while a high-pass filter and low-pass filter was set with a cut-off frequency of 1 Hz and 200 Hz, respectively. A customized MATLAB program was developed to process the recorded LFP signal. Power spectrum density (PSD) was calculated by fast-Fourier transformation with a multiband analysis method. In the power spectrum analysis using the built-in spectrogram function in MATLAB, the signal of frequency around 50 Hz (48~52 Hz) was omitted from the analysis. PSDs in six distinct frequency bands were then summed, i.e., 1-4 Hz (δ-band), 4-7 Hz (θ-band), 7-13 Hz (α-band), 13-30 Hz (β-band), and 30-70 Hz (γ-band). The analysis data were randomly chosen from the long-term recording data for the three cases: untreated cases, prevention mode and clearance mode which were chosen after seizure onset, respectively.

In experiments to assess the long-term biocompatibility of a μNTron device, the mouse underwent the same surgical procedures. After the implantation, dental cement was carefully applied to seal the surgical region. After a recovery period of 2 or 4 weeks, the mice were sacrificed for histology analysis.

Seizures were characterized as high-frequency, high-voltage, and synchronized neural spiking. The early onset of a seizure like event (SLE) was indicated by a 3.5% or greater power increase of the β oscillation of LFP (13-30 Hz), and an SLE was defined as a more than 6% power increase of β oscillation. For controlled drug releasing, an electrical stimulator (A.M.P.I) was used to provide constant voltage stimuli ranging from 50 mV to 400 mV at selected electrode to drive the release of biomolecules (GABA, VPA). For GABA administrations, 1 mg/mL GABA was loaded in a μNTron device, a drug release was triggered upon the detection of an onset indicator of SLE in the "Prevention" group; or triggered after the detection of a full seizure outburst in the "Clearance" group.

SI Information

Morphological and Chemical Characterizations

The FT-IR spectra of DMAPS, PF127-DA, and DMA/PEDOTS-IPN hydrogels were recorded on a Nicolet 6700 FT-IR spectrometer (Thermo Scientific) in the 4000-600 cm$^{-1}$ range. Hydrogel samples (DMA/PEDOTS-IPN10, DMA/PEDOTS-IPN20, DMA/PEDOTS-IPN30, and DMA/PEDOTS-IPN40) were sprayed with a thin gold layer, then the morphologies of freeze-dried hydrogels were examined by a field emission scanning electron microscope (FEI Quanta 250 E-SEM). FIJI software was employed to measure the electrode height, tip morphology of μNTron samples. As for the pore diameters of hydrogel samples, FIJI was also employed to measure with the same procedure. Finally, the above data was analyzed by Student's t-test, where if p value <0.05 and it can be considered statistical significance. The volume change ratio of the hydrogels was determined by swelling tests. The hydrogels (DMA/PEDOTS-IPN30 and PAAm hydrogel group), with the same volume (7 mm×7 mm×1 mm), were immersed in 10 mL PBS solution (pH=7.4) at 37° C. At the predetermined time intervals, all hydrogel samples were taken out from PBS and measured length (l), width (w) and height (h) after wiping the external water. The volume change ratio was calculated according to the following formula:

$$\text{Volume change ratio of } (\%) = (V_t - V_0)/V_0 \times 100\%$$

$$V = l \times w \times h$$

where $V_t$ and $V_0$ are the volume of the hydrogel samples at different time points in PBS and the original volume of the initial hydrogels, respectively.

In vitro degradation test, the in situ formed hydrogel samples (DMA/PEDOTS-IPN30 and PAAm hydrogel group), with the same volume (7 mm×7 mm×1 mm), were immersed in 10 mL PBS (pH=7.4) at 37° C. Hydrogel samples were picked out from PBS solution after different time intervals. Next, all the hydrogel samples were rinsed with DI water to remove excess salinity. they were then dried in an oven at 70° C. overnight and weighed until stable values. The weight remaining ratio % of hydrogels were then defined by the following equation:

$$\text{Weight remaining ratio of hydrogel} = W_t/W_0 \times 100\%$$

where $W_t$ and $W_0$ are the dry weight of the remaining hydrogels after degradation at different time points and the dry weight of the initial hydrogels, respectively.

Conductivity Characterization

The conductivity measurements of DMA/PEDOTS-IPN10, DMA/PEDOTS-IPN20, DMA/PEDOTS-IPN30, and DMA/PEDOTS-IPN40 were carried out at 25° C. using a direct current (d.c.) four-point probe method with a Keithley 2612B System Source Meter to get the resistance (R). And the conductivity (σ) was calculated as following equation:

$$\sigma = 1/R \cdot 1/(w \cdot t)$$

where width (w) and length (l) of the hydrogel film are measured with calliper carefully.

Electrochemical Characterization

An Electrochemical Workstation (CHI 760E Instruments) was employed to get the cyclic voltammetry (CV) of DMA/PEDOTS-IPN hydrogels. A classical three-electrode system was employed with Ag/AgCl as the reference electrode and platinum electrode as the auxiliary electrode. The prepared hydrogel samples were fixed with a platinum electrode holder at constant exposure area as the working electrode in PBS. Then the solution was deoxygenated by pouring N2 for several minutes. The scan rate was 10 mV/s from −0.45 mV to 0.45 mV.

Electrochemical impedance spectroscopy (EIS) and AC impedance were measured by using the hydroElex sample as the working electrode which was immersed in PBS with one needle. And platinum electrode, Ag/AgCl were chosen as auxiliary electrode and reference electrode, respectively. AC impedance measurements were obtained between 1 Hz and 10 kHz at 100 mV amplitude.

Mechanical Strength Test

The mechanical tensile stress-strain evaluation was carried out by the uniaxial tensile test employing an Instron materials test system (Instron 5942 Mechanical Tester) equipped with a 500 N tension sensor at room temperature. All the hydrogel samples were prepared into standard stripes (12.5 mm in length×3.2 mm in width×1.4 mm in thickness). The Young's modulus, tensile strength and elongation at break were obtained at a crosshead rate of 1.2 mm/min. The Young's modulus was determined from the slope of the stress-strain curve.

As for the mechanical strength of the electrode was evaluated by pressing vertically them which were fixed on a stainless-steel plate. Briefly, the test station sensor probe was set to vertical move at a speed of 0.1 mm/min. The initial distance of the probe with electrode tips was set as 2 mm. Displacement and force measurements began when the sensor first touched the electrode tips and continued until when the electrode began to buckle.

Ex Vivo Electrical Signals Recordings.

By using a function generator (DSO-X 3012A, Agilent Technologies), three kinds of square pulses with 5000, 1000 and 100 Hz were generated respectively. All these signals were measured in PBS by μNTron device and commercial tungsten microelectrode (FHC, 223207) as a control group.

H&E and Nissl Staining

After LFP recording test, the implanted μNTron device was taken out from the experimental mice brain carefully. The mice were transcardially perfused with ice-cold PBS and subsequently 4% paraformaldehyde (PFA, in PBS) before they were sacrificed. The brain was then harvested to be further fixed in 4% PFA (in PBS) overnight, followed by dehydration in 30% sucrose (in PBS) until settled at the bottom. The frozen samples were sectioned into was later sectioned to coronal slices (50 μm thickness) using a Cryostar NX70 cry sectioning instrument (Thermo Scientific) storage at −80° C.

All the frozen samples were stained by the Hematoxylin-Eosin (H&E) and Nissl staining as the standard protocols to evaluate the biocompatibility and brain damage at the implantation site for the hydroElex device. The stained sections of each sample were examined by a microscope (Olympus, Japan).

Results

Synthesis of the Electroactive Stimuli-Responsive Hydrogels

Figure 2A:
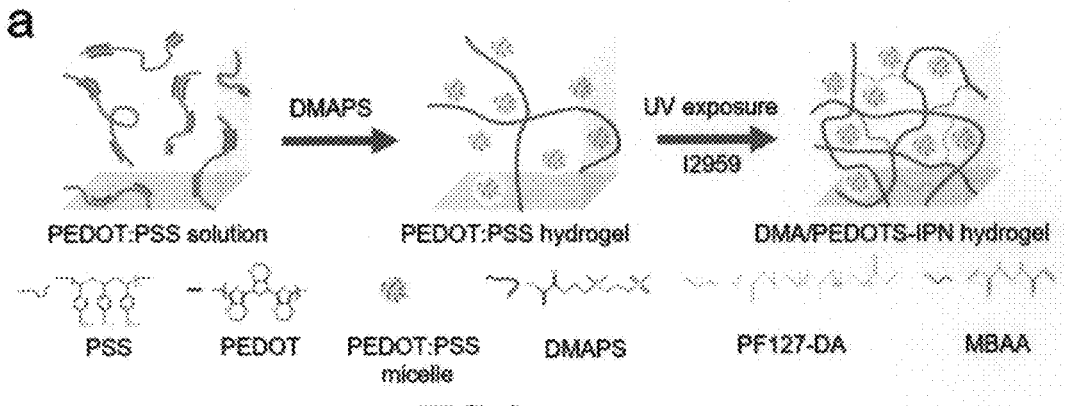
Figure 2B:
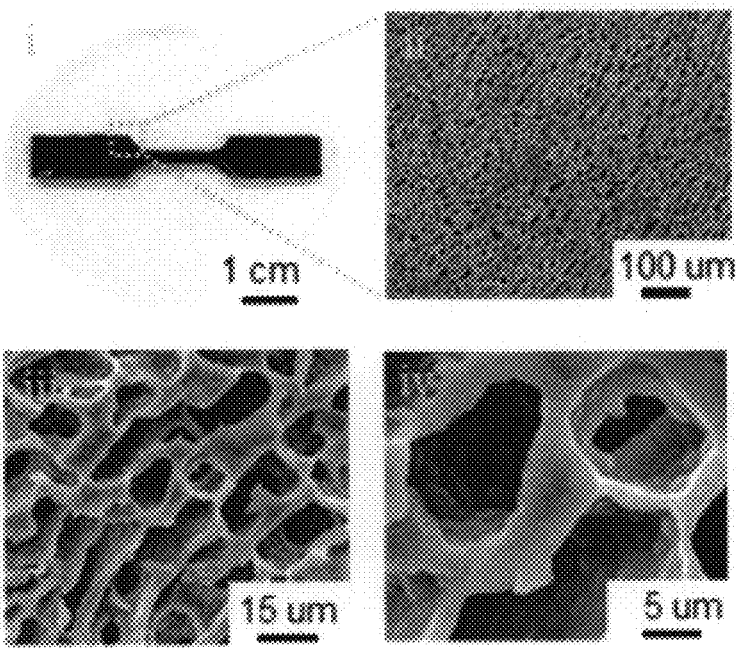
Figure 2C:
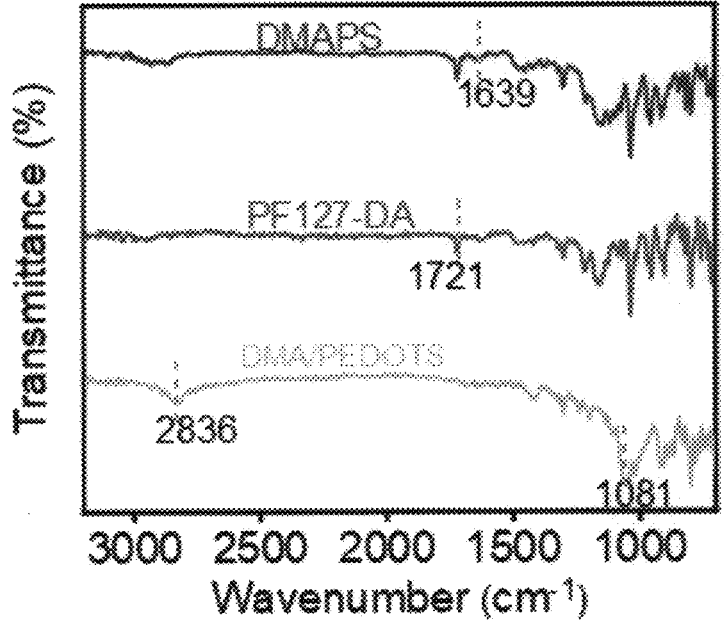
Figure 2D:
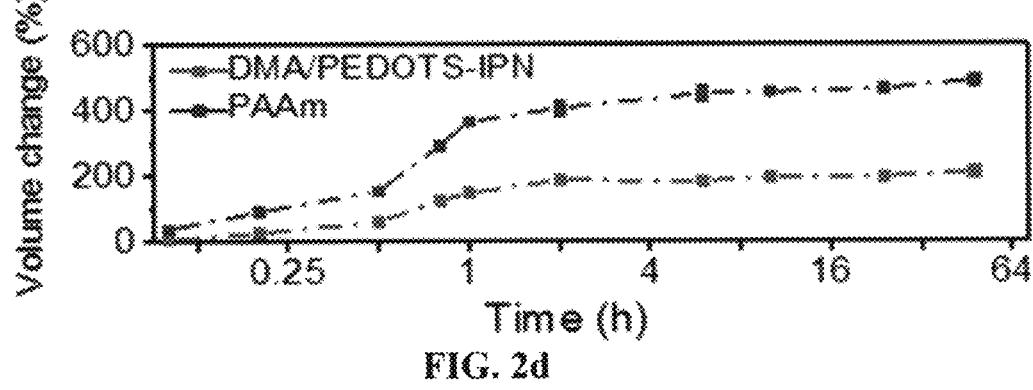
Figure 2E:
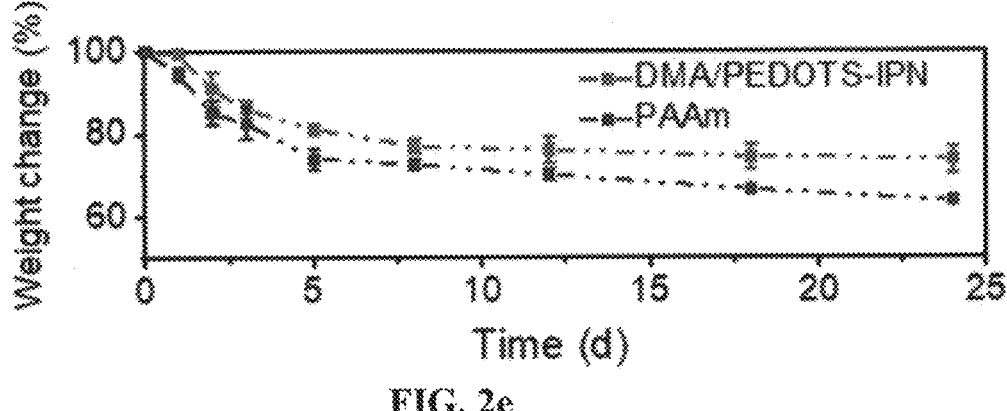
Figure 2F:
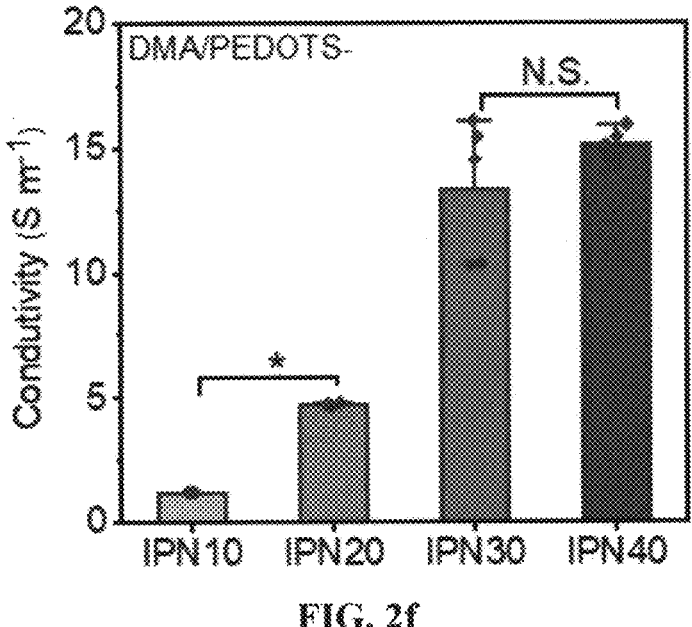
Figure 2G:
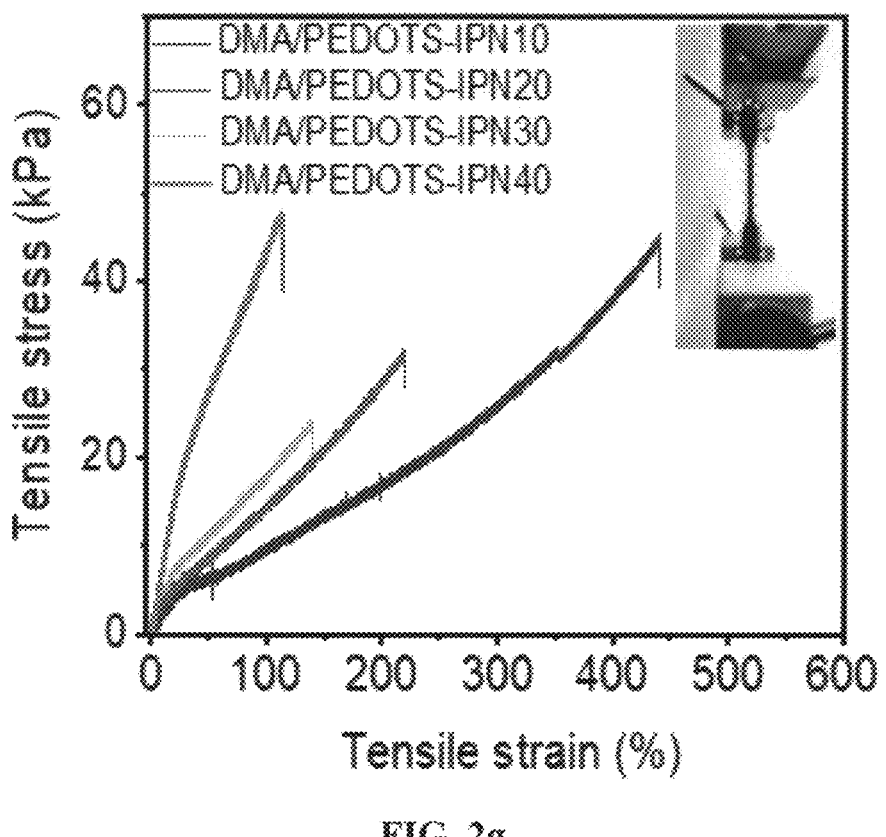
Figure 2H:
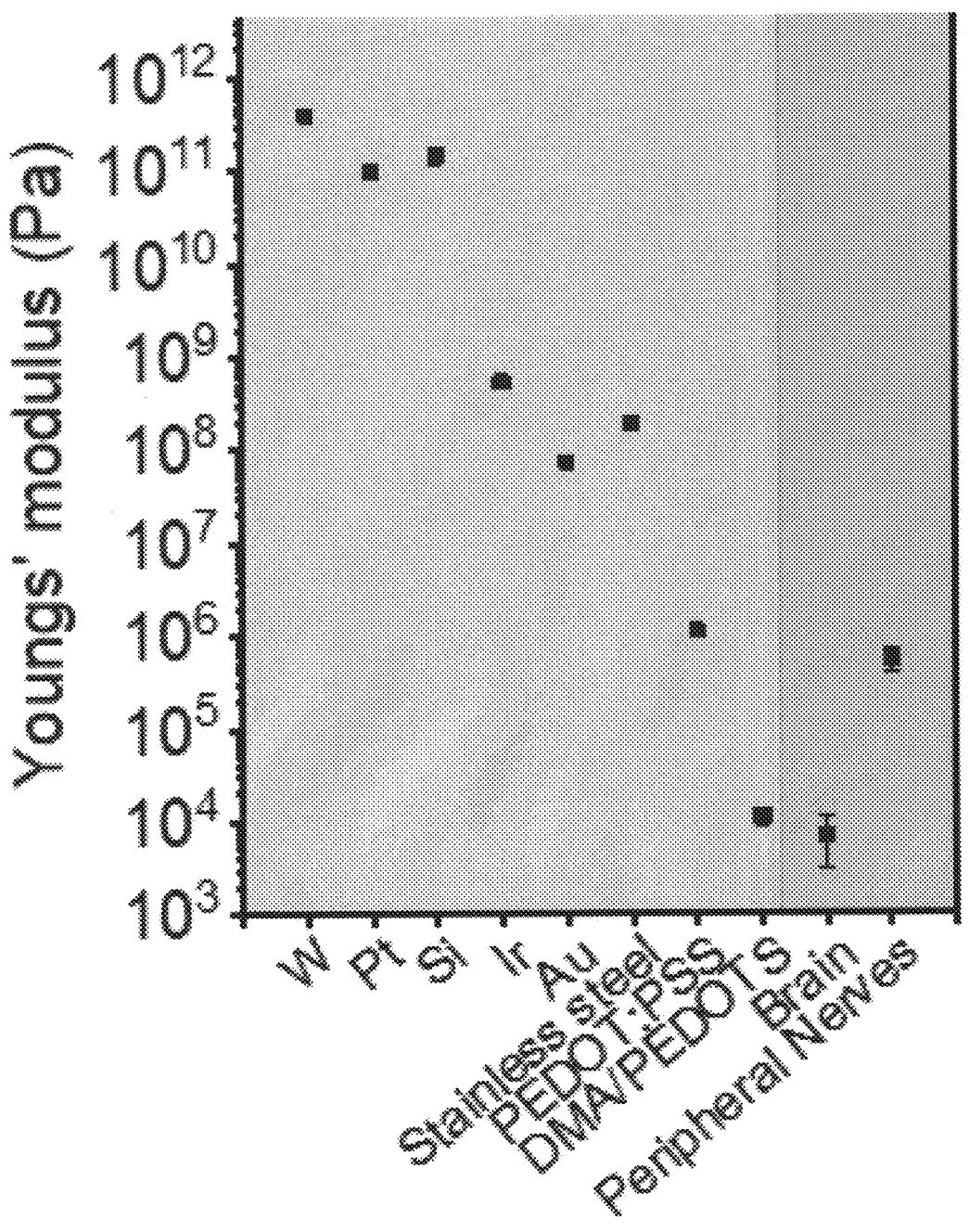

The μNTron device is featured as an array of in situ polymerized microneedles on flexible thin film, where each of the microneedles can be independently addressed and function as signal recording and drug releasing unit. Please see FIG. 1. To prepare the electroactive hydrogel, PEDOT:PSS dispersions (~1.1 wt % solid content) were mixed with DMAPS to form a primary crosslinking network. The mixing was followed by addition of crosslinker diacrylate-functionalized poly(ethylene glycol)-b-poly(propylene glycol)-b-poly(ethylene glycol) (PF127-DA), bis-acrylamide (MBAA) and photo-initiator Irgacure 2959. Please see FIG. 2a. FIGS. 2a to 2h illustrate the synthesis and characterization of DMA/PEDOTS-IPN hydrogel. Specifically, FIG. 2a is a schematic diagram showing the synthesis of the DMA/PEDOTS-IPN; FIG. 2b are representations of the synthesized DMA/PEDOTS-IPN in which portion (i) is a photogram, and portions (ii), (iii), (iv) are and SEM images [scale bar, 1 cm (i), 100 μm (ii), 15 μm (iii), and 5 μm (iv)]; FIG. 2c shows FT-IR spectra of the components in DMA/PEDOTS-IPN hydrogel; FIG. 2d shows volume change of the DMA/PEDOTS-IPN hydrogel in the biomimetic physiological environment in vitro (n=3); FIG. 2e shows chronic degradation of the DMA/PEDOTS-IPN hydrogel in terms of the change of weight (n=3); FIG. 2f shows conductivity of the DMA/PEDOTS-IPN hydrogels with different amount of DMAPS content (n=5); FIG. 2g shows tensile test of the DMA/PEDOTS-IPN hydrogels (n=3); and FIG. 2h shows comparison of Young's modulus values between commonly used for penetrating nerve electrodes and the DMA/PEDOTS-IPN hydrogel. (In these figures, conductive materials and nerve tissue are shaded in bule and pink, respectively. All error bars denote the s.d. * for p<0.05, NS, not significant by test.)

Figures 7A, 7B:
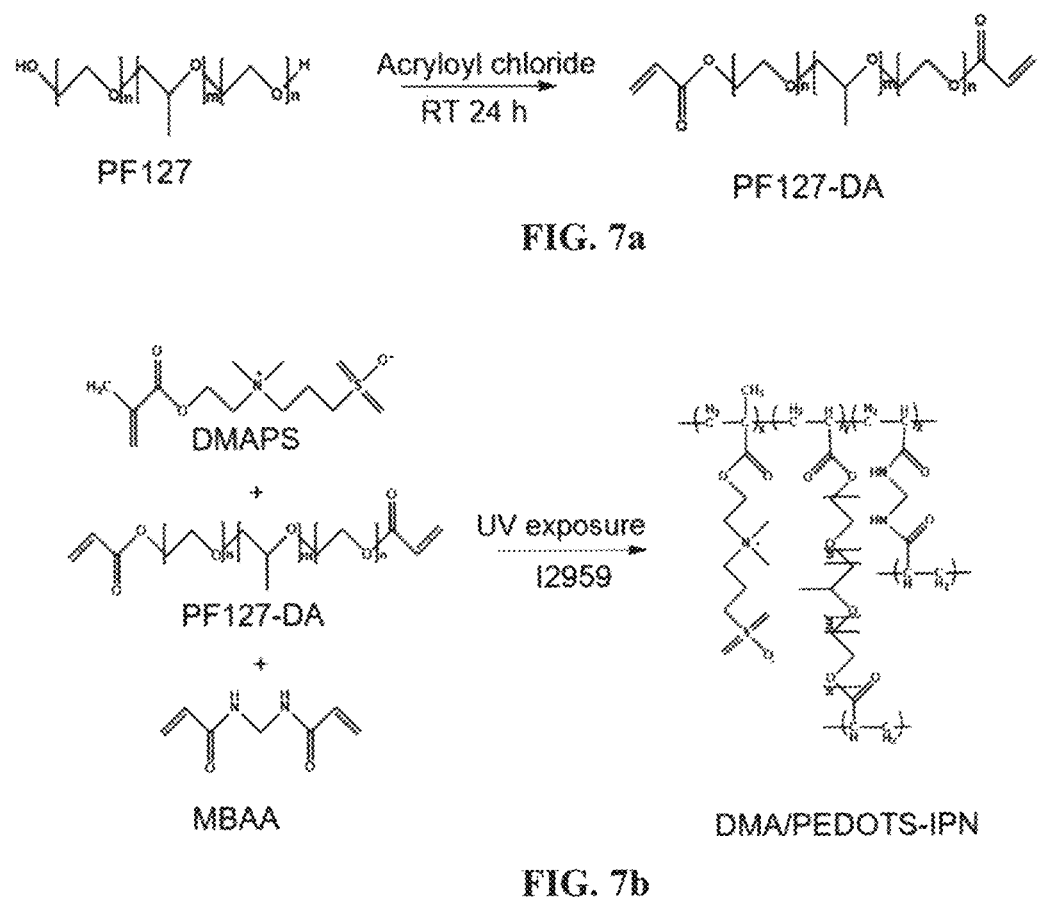
Figure 7C:
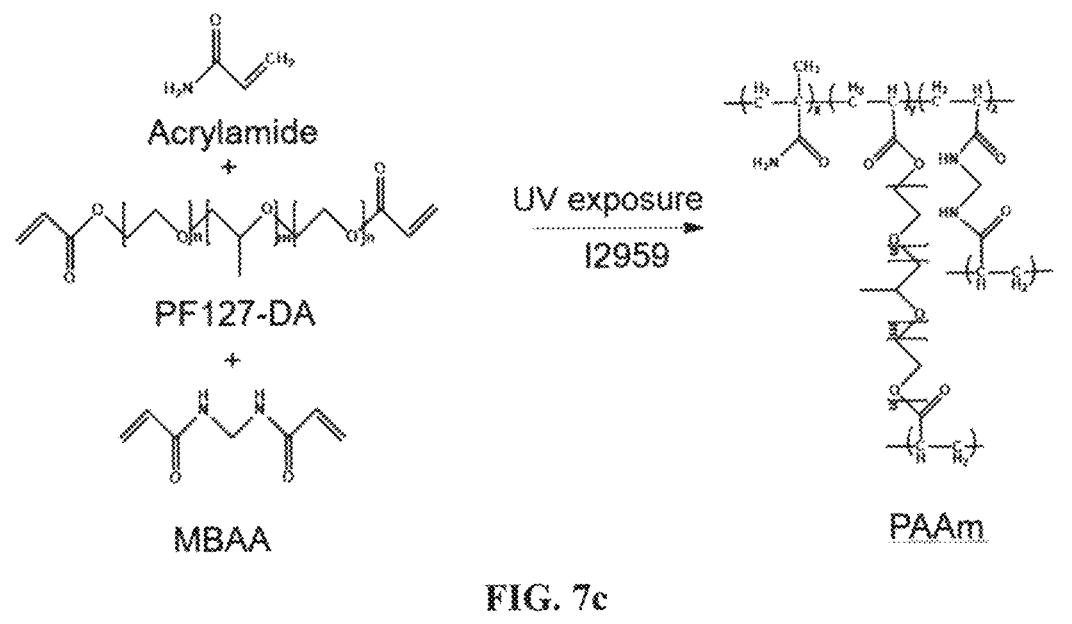
Figure 8A:
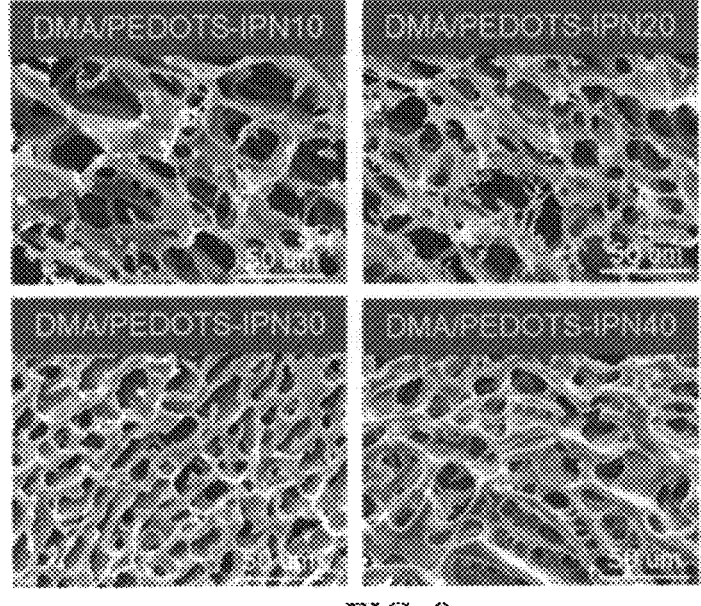
FIGS. 8a to 8b are images and a graph showing the internal structure of an embodiment of hydrogel material according to the present invention.
Figure 8B:
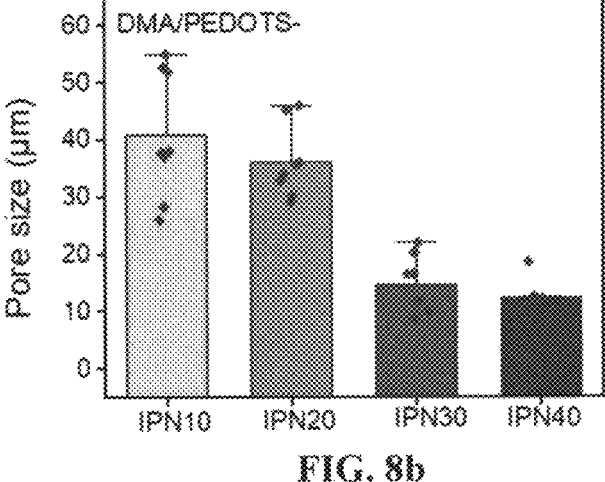

Upon UV exposure, the precursor solution underwent in situ polymerization to form the ready-to-use conductive hydrogel structures. Please see FIGS. 7a to 7c. FIG. 7a shows the procedures for synthesizing PF127-DA polymer; FIG. 7b shows the procedures for crosslinking precursors to form the DMA/PEDOTS-IPN hydrogel; and FIG. 7c shows the structure of a commonly-used (acrylamide) PAAm hydrogel used for comparison in this study. FIGS. 2b and 8a to 8b shows a tunable microscale porous network. FIG. 8a are SEM images of the DMA/PEDOTS-IPN hydrogels with various pore sizes based on different formulations of DMAPS concentration (10%, 20%, 30%, and 40%, wt/vol); and FIG. 8b is a graph showing the quantitative analysis of the pore size of the hydrogels (n=8) (scale bar: 50 μm. The error bars indicate s.d.)

After polymerization, the resulted hydrogel was examined by Fourier-transform infrared spectroscopy (FT-IR). Compared to the specific precursor components (DMAPS and PF127-DA), the disappearance of 1639 cm$^{-1}$ and 1721 cm$^{-1}$ showed the break of C=C or C=O bonds in DMAPS and PF127-DA, respectively; the newly formed C—H bond and addition of S-phenyl group was indicated by signal at 2836 cm$^{-1}$ and at 1081 cm$^{-1}$ in the resulted DMA/PEDOTS-IPN hydrogel {Zhao, 2018 #27; Sriprachuabwong, 2012 #28}.

Figure 3A:
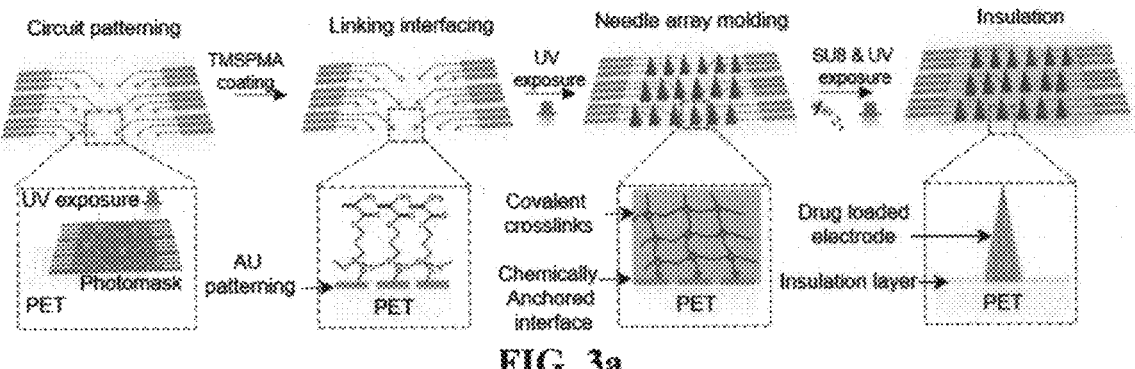
Figure 3B:
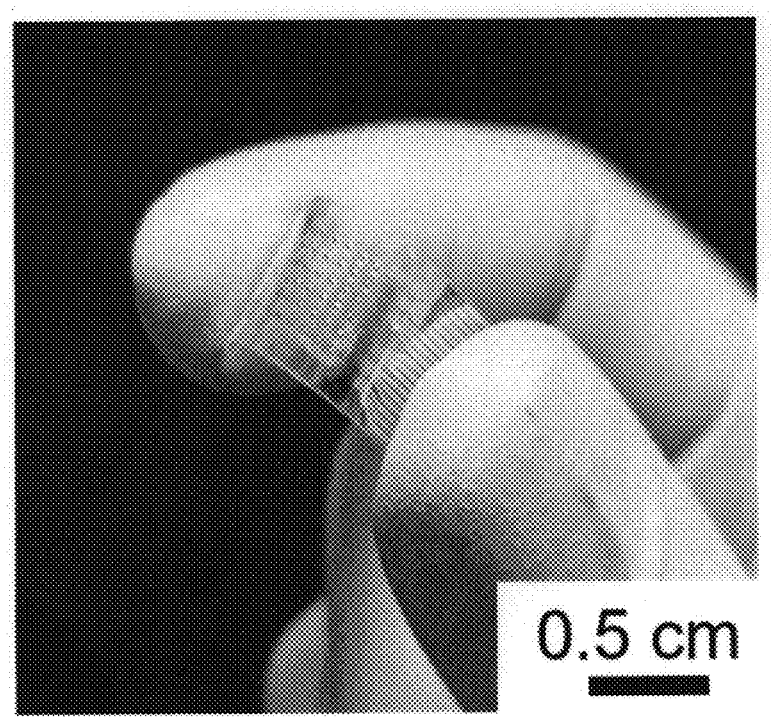
Figure 3C:
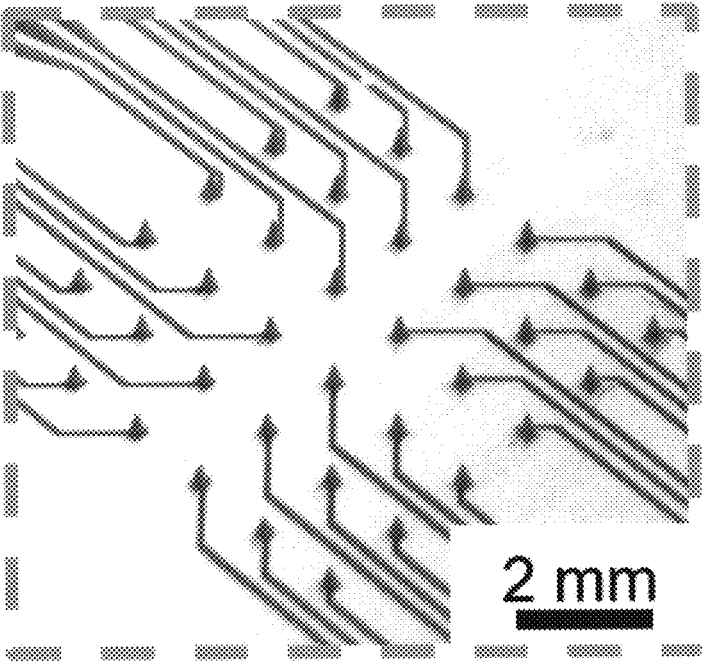
Figure 3D:
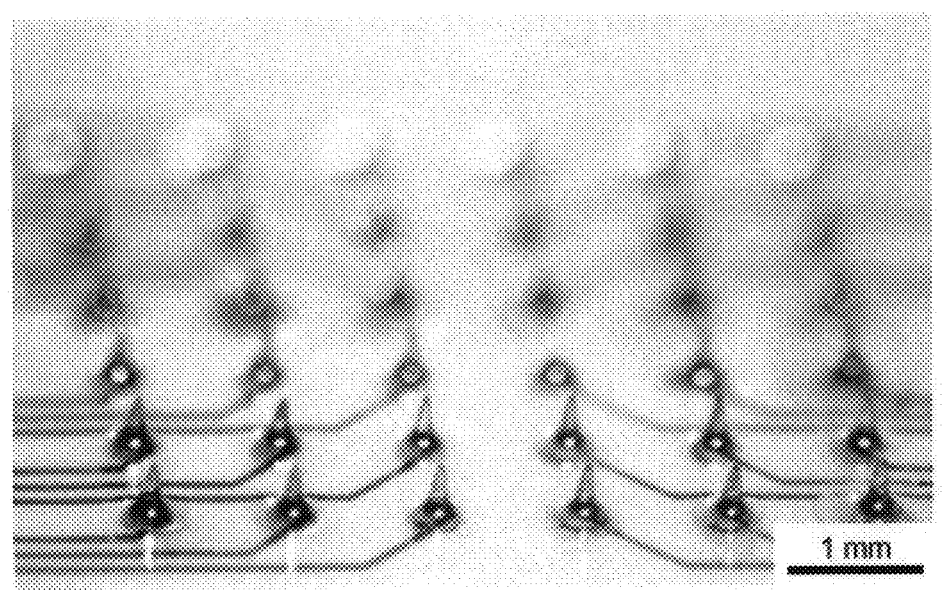
Figure 3E:
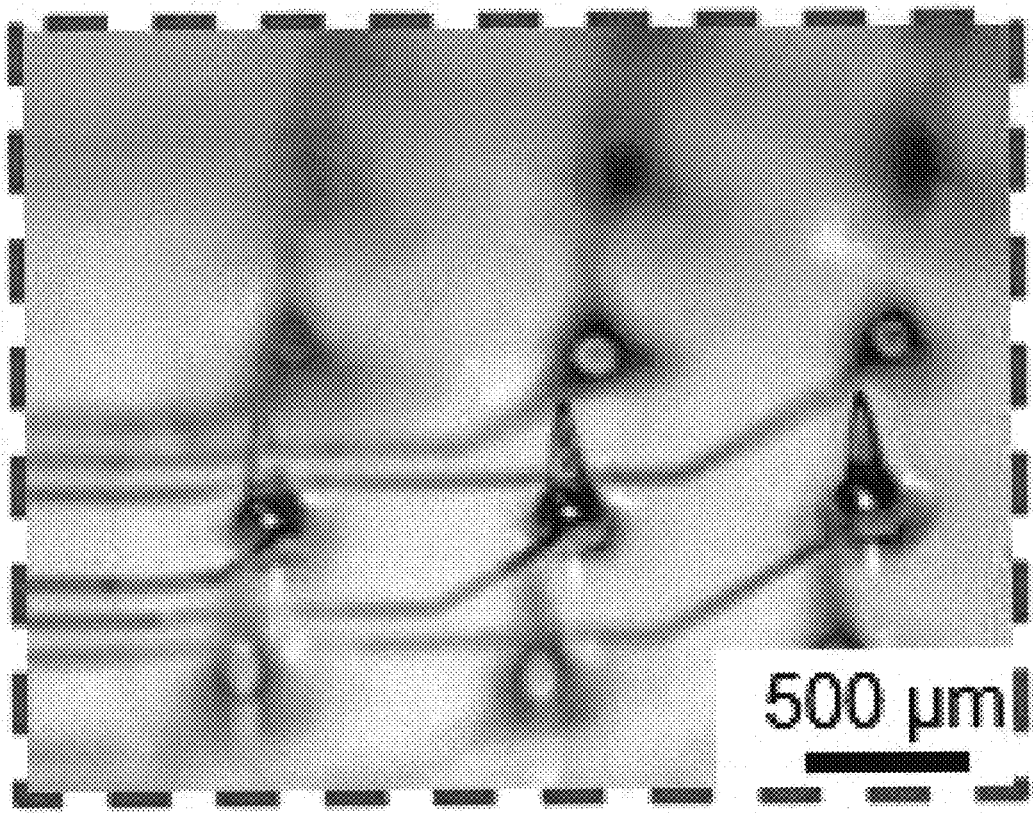
Figure 3F:
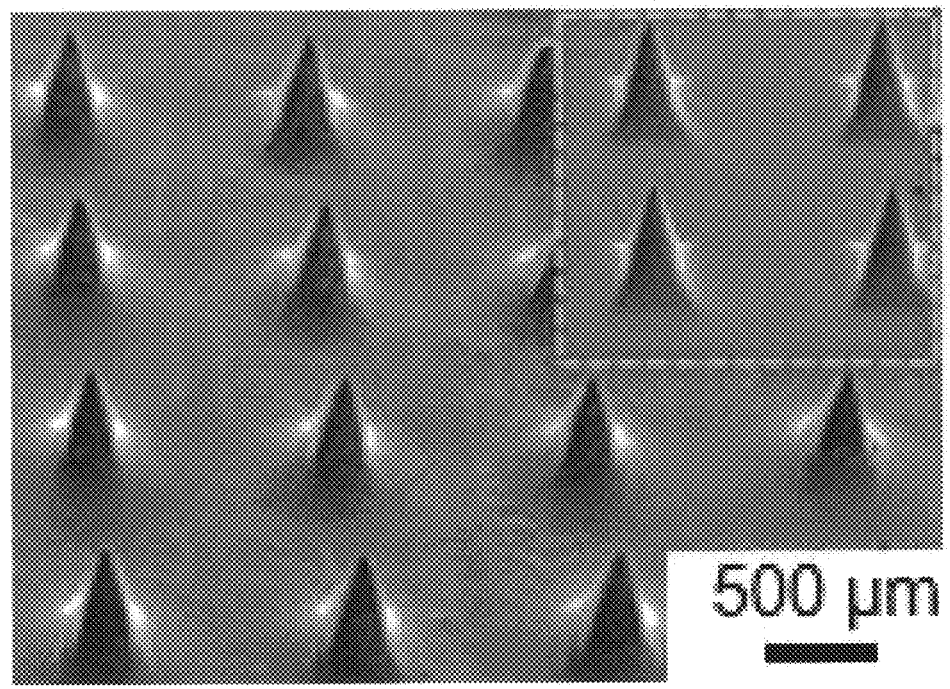
Figure 3G:
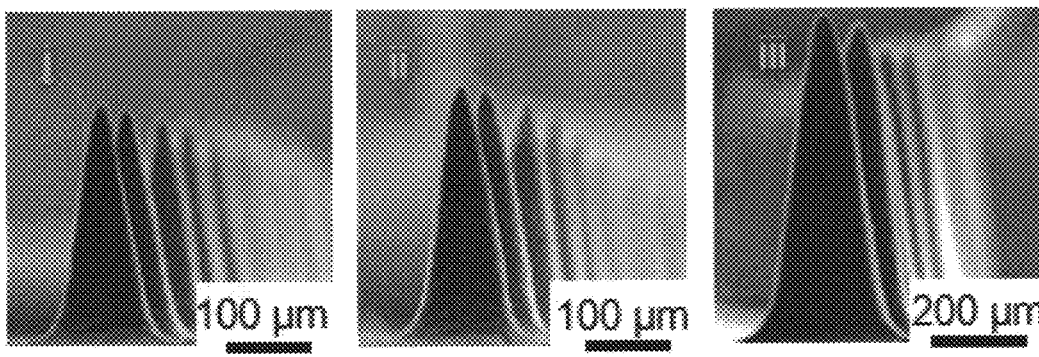
Figure 3H:
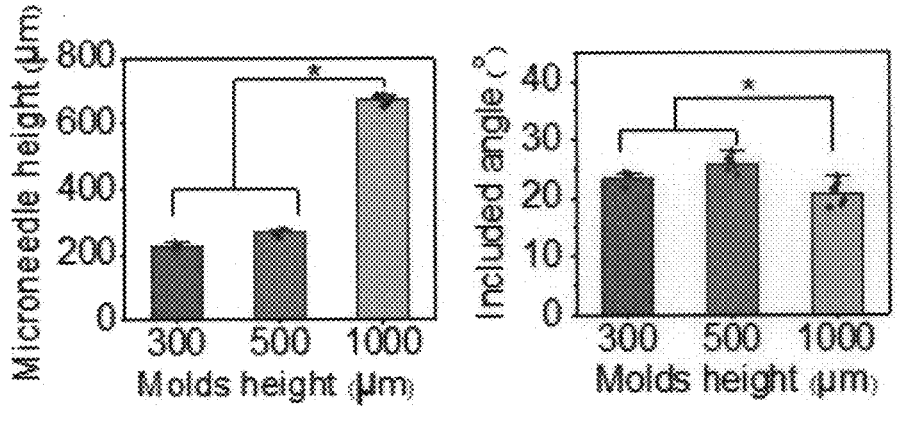
Figure 3I:
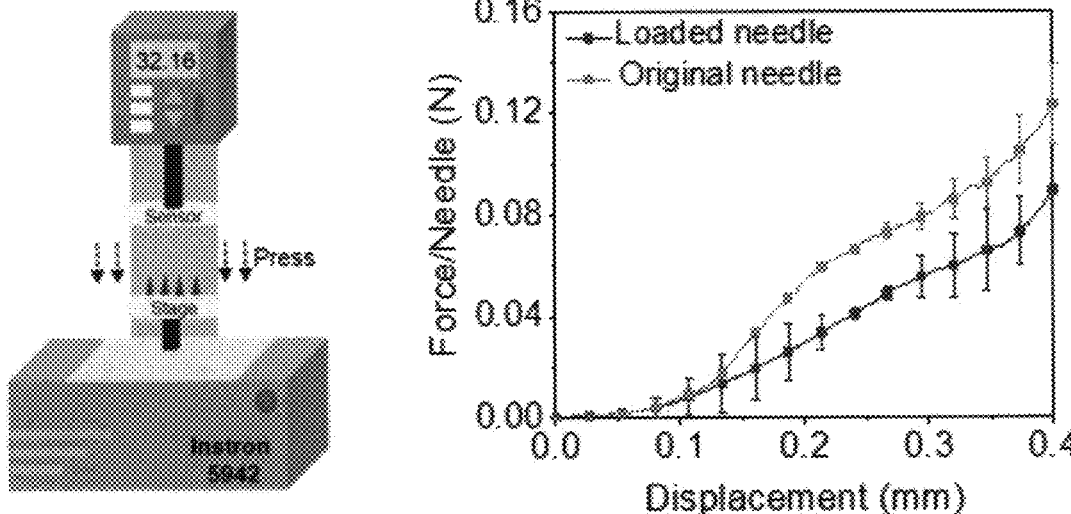

Please see FIG. 2c. These characteristic peaks confirm a success in hydrogel crosslinking, as well as a physical inclusion of the PEDOT:PSS inserts. The polymerized hydrogel exhibits excellent structural stability. After 48 hours in PBS at 37° C., the volume swelling from lyophilized format was about 60% lower than the commonly-used (acrylamide) PAAm hydrogel (210.92±17.27% vs 490.56±15.30%. Please see FIG. 2d and 7. The degradation of the DMA/PEDOTS-IPN hydrogel is also slower, and only minor weight loss (26.33±3.2%) was observed after 24-day incubation in a biomimetic environment. Please see FIG. 2e. The structural and compositional stability of the electroactive hydrogel makes it a suitable material for long-term in vivo usage to manage chronic diseases. The characterization of hydrogel conductivity shows a positive correlation between the conductivity and the concentration of DMAPS (10%~40% wt/vol), ranging from 1.22±0.01 to 15.14±0.58 S m$^{-1}$. Please see FIG. 2f. For a series of hydrogels with various DMAPS formulations, the sample was stretchable up to a strain of 430%, corresponding to elastic modulus ranging from 9.96±0.14 kPa to 35.14±0.14 kPa, which is comparable to the modulus measured from brain tissues (3.15-10 kPa). Please see FIG. 2g and below Table S1.

single microneedle electrode, which is the basic functional unit and can be individually addressed by separate wires. FIGS. 3a to 3i illustrate the fabrication of the μNTron. Specifically, FIG. 3a is a schematic diagram of a four-step fabrication process; FIGS. 3b-3e are representative photograms of the fabricated μNTron [scale bar, b=0.5 cm, c=2 mm, d=1 mm, e=500 μm]; FIG. 3f is a SEM image of the casted microneedle with SU8 insulation layer (insert: without insulation layer of microneedle; scale bar, 500 μm); FIG. 3g is a SEM image of the microneedle casted using mold measured is 300 μm [portion (i)], 500 μm, [portion (ii)] and 1000 μm [portion in height, respectively (scale bar, i, ii=100 μm, iii=200 μm]; FIG. 3h is morphological quantification of the height (left) and the tip angle (right) of the fabricated microneedles on μNTron (n=20) and FIG. 3i shows the mechanical strength of compressed microneedle with (blue) and without (red) loaded GABA (n=3). (All error bars denote the s.d. * for p<0.05 by test.)

Figure 9A:
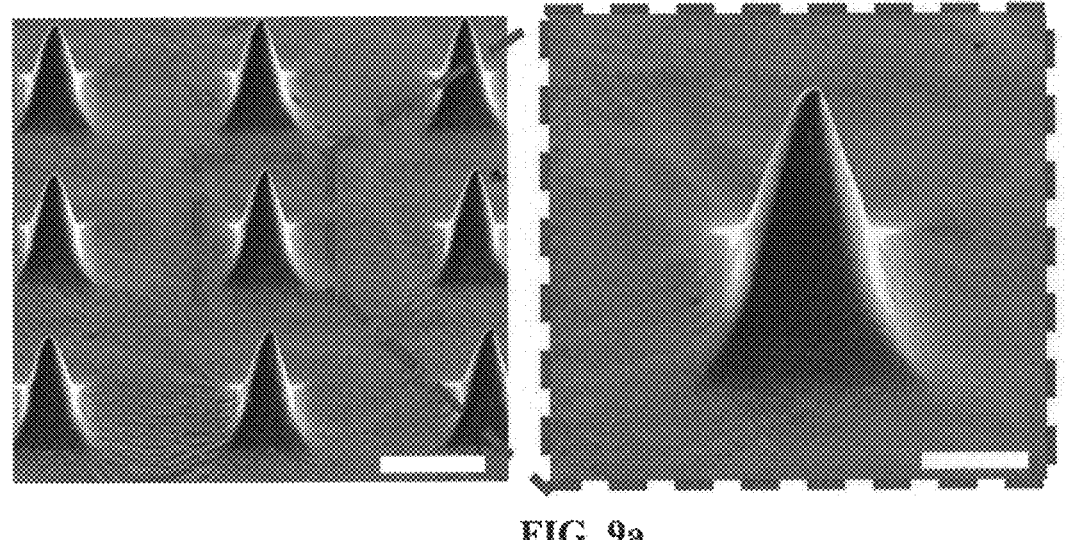
FIGS. 9a to 9b are photographic images showing microneedles of an embodiment of an electronic device according to the present invention.
Figure 9B:
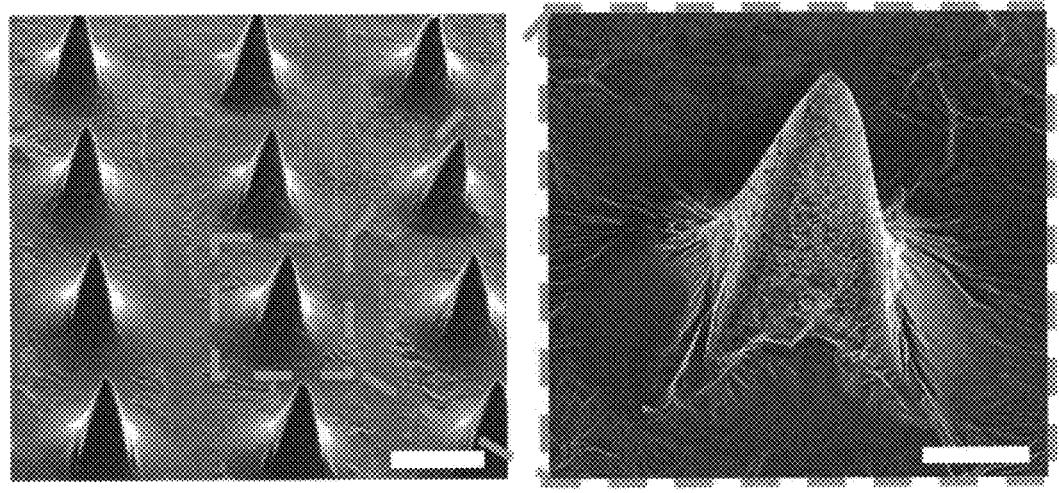

Fabrication of the device involves a convenient four-step method. Please see FIG. 3a and further description below. In one embodiment, the method begins with a thin flexible polyethylene terephthalate (PET) film on which the layout of gold circuit is formed by lift-off procedures. Suitable elements other than gold may be used. Then 3-(trimethoxysilyl) propyl methacrylate (TMSPMA) is coated on the substrate to promote covalent bonding of DMA/PEDOTS-IPN hydrogel. The silane groups at one end of TMSPMA form hydrogen bonds with the hydroxyl and carboxylic groups on the plasma treated PET surfaces; the other end polymerizes with the acrylate groups in DMA/PEDOTS-IPN hydrogel to enable a stable fixation of the hydrogel microneedles on the PET substrate. A layer of SU-8 is then used as the insulation package to seal the circuits while the tips of the microneedles were exposed for biological interfacing. FIGS. 9a to 9b are SEM images of the microneedle electrodes before (see FIG. 9a) and after (see FIG. 9b) the assembly of SU8 insulation layer. The tips of the electrodes were exposed for biological interfacing. Scale bar, 500 μm (left) and 150 μm (right).

Experiments have shown that the fabricated device can sustain repeated bending for at least 100 cycles without any detectable damages. Please see FIGS. 3b and 3c. The

TABLE S1

| Samples | DMAPS (wt/vol) | PF127-DA (wt/vol) | MBAA (wt/vol) | PEDOT:PSS (wt/vol) | UV exposure (min) | Youngs' modulus (KPa) |
|---|---|---|---|---|---|---|
| DMA/PEDOTS-IPN10 | 10% | 14% | 0.5 | 0.7% | 25 | 9.96 + 0.14 |
| DMA/PEDOTS-IPN20 | 20% | 14% | 0.5 | 0.7% | 25 | 13.26 + 0.03 |
| DMA/PEDOTS-IPN30 | 30% | 14% | 0.5 | 0.7% | 25 | 13.73 + 0.01 |
| DMA/PEDOTS-IPN40 | 40% | 14% | 0.5 | 0.7% | 25 | 35.14 + 0.14 |

In contrast to other commonly used materials (e.g. platinum, tungsten and PEDOT:PSS), a matching modulus ensures better integration with the host neural tissues with minimal contact resistivity {Akhtar, 2011 #29; Patil, 2016 #30}. Please see FIG. 2h. In the DMA/PEDOTS-IPN hydrogel, the DMAPS backbone plays an essential role to modulate the mechanical and electrical properties by changing the crosslinking density and therefore the in-situ polymerization among the acrylate groups, and by affecting the physical interaction between the backbone and the PEDOT:PSS inserts.

Fabrication of the μNTron Devices

Figure 4A:
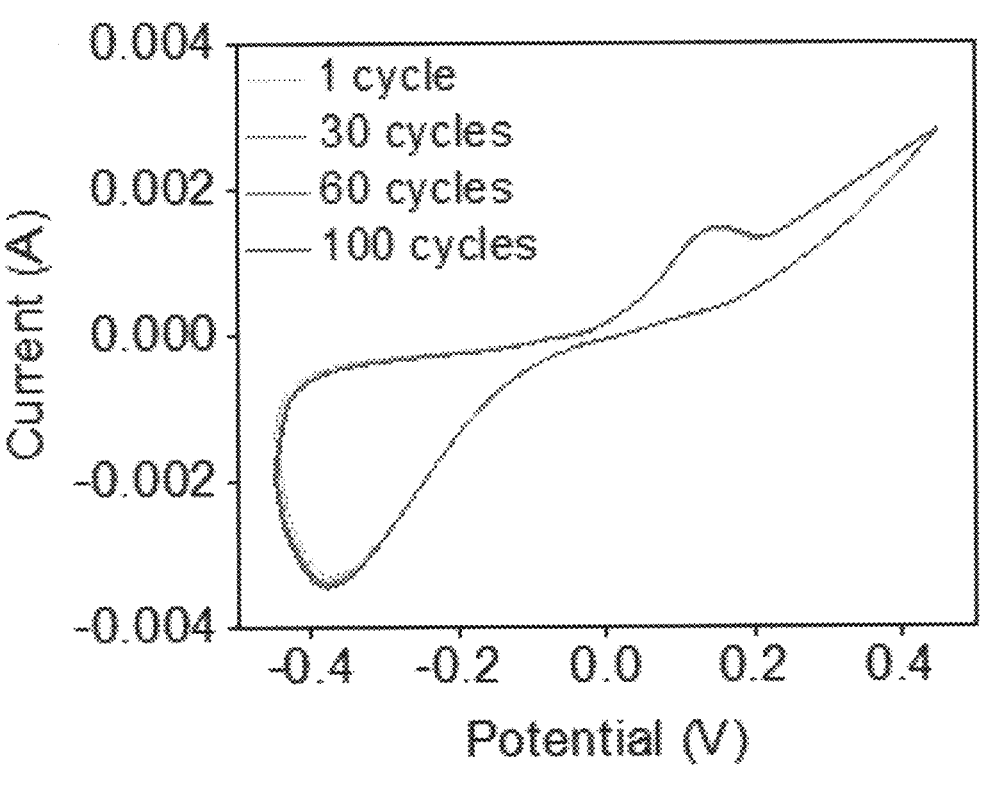
Figure 4B:
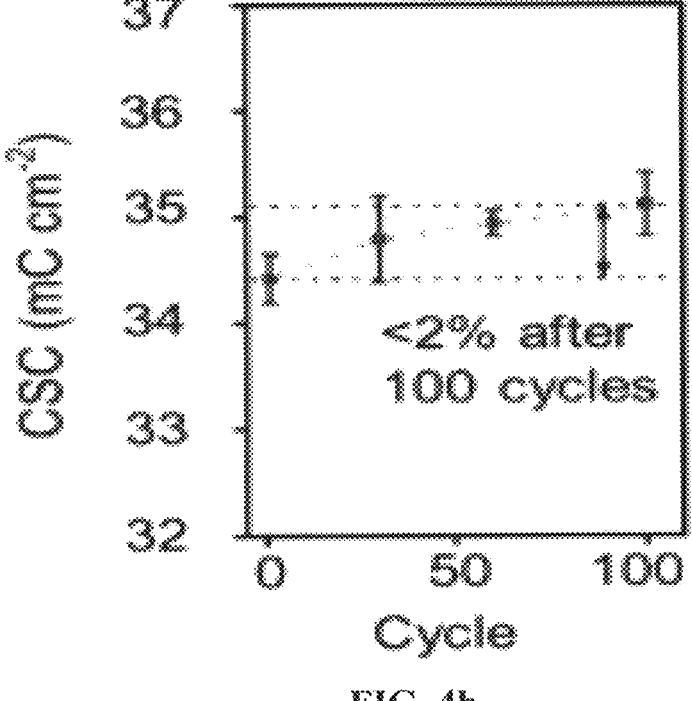
Figure 4C:
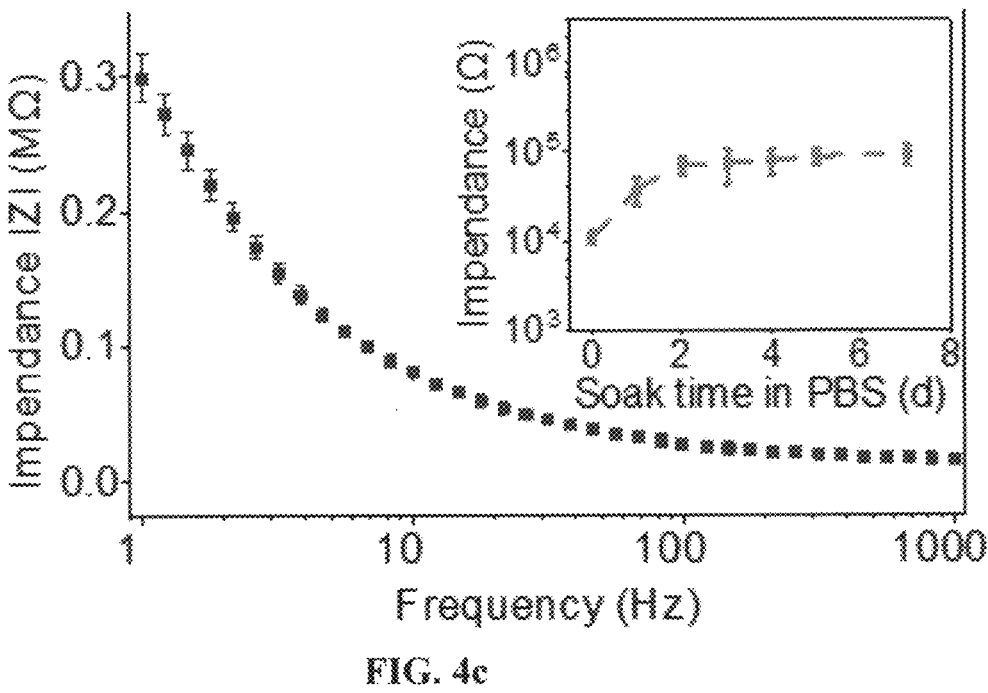
Figure 4D:
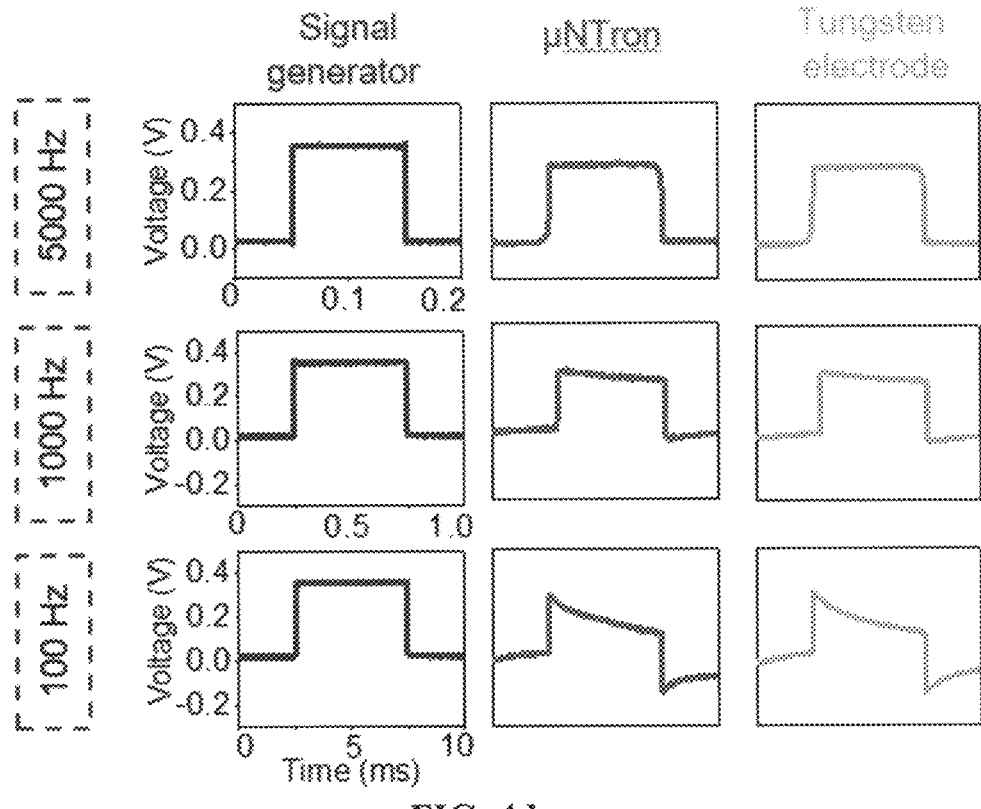
Figures 4E, 4F:
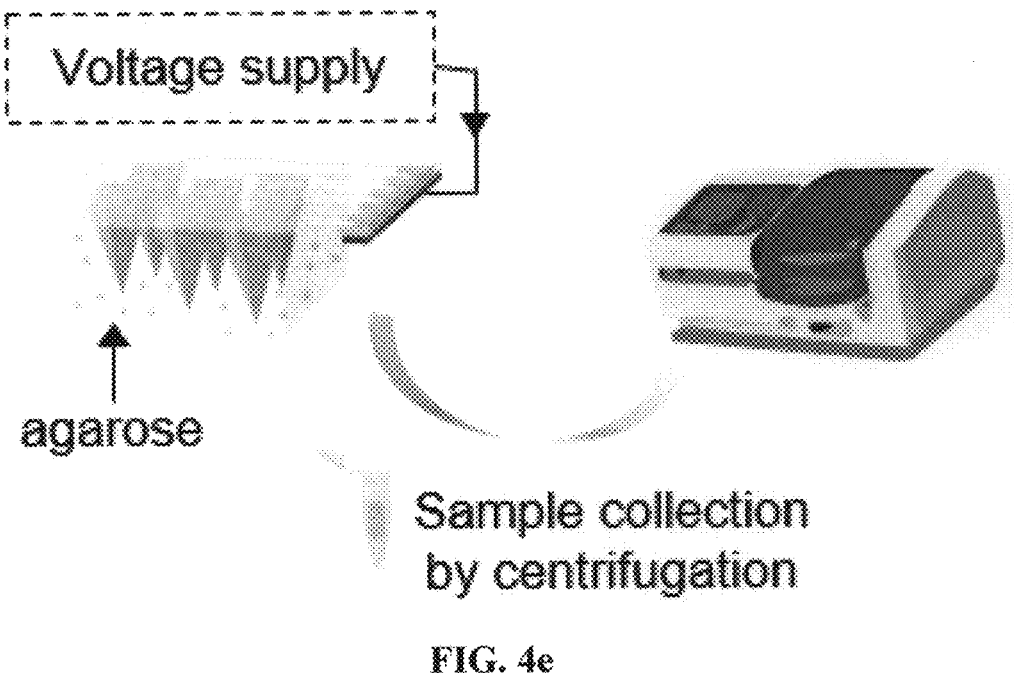
Figure 4G:
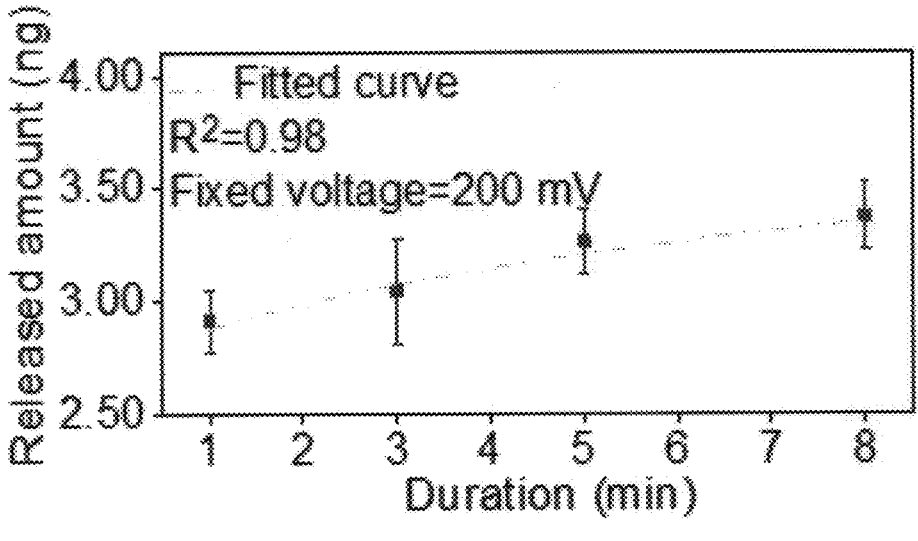
Figure 4H:
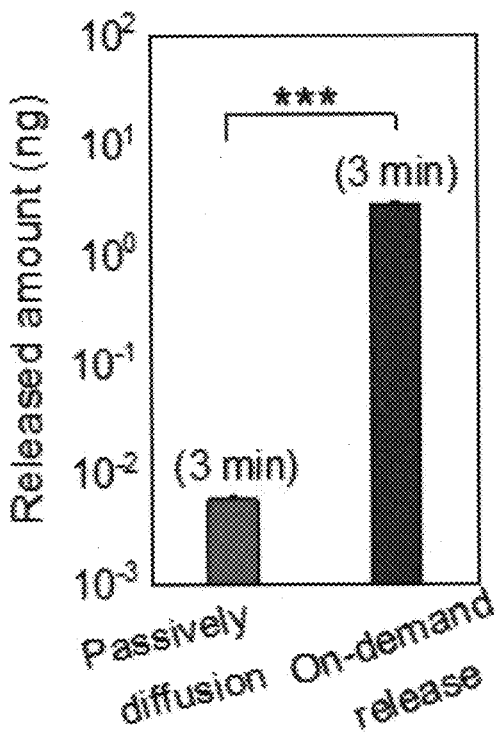
Figure 4I:
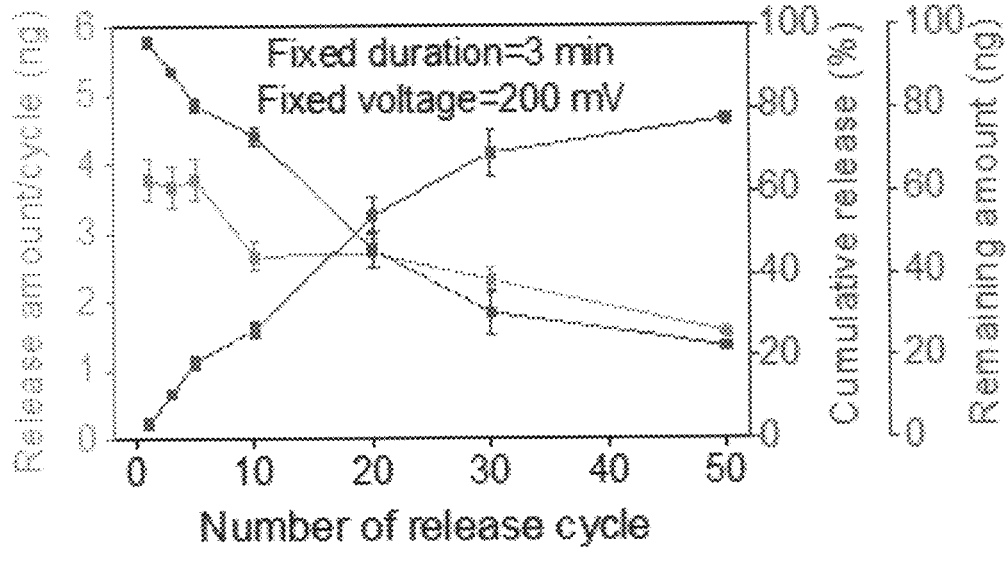

To implement a closed-loop strategy, the μNTron device are used to allow a bi-directional crosstalk between physiology surveillance and pharmaceutical intervention at every transparency of the microneedles can facilitate their aligned assembly on the PET substrate to guarantee proper wiring. Please see FIGS. 3d and 3e. A pyramid shape of each microneedle further improves the placement and fixation of the device in the tissues after being implanted to an animal brain. Please see FIG. 3f. The height of microneedles is measured at 673.02±13.08 μm and the tip sharpness was measured at 20.85±2.18°. Please see FIGS. 3g-3h. This characteristic provides an easy access to relatively deeper cortical tissues with minimized damage, which is important for the surveillance of abnormal neural activity and rapid release of drug molecules to a wider range of brain cells. The mechanical strength of the μNTron device was characterized using a force gauge, showing a failure level beyond 0.07 N/needle for unloaded and 0.05 N/needle for drug-loaded (1 mg/mL, GABA in PBS) microneedles, respectively. Please see FIG. 3i. In both cases, the microneedle electrodes are sufficient to penetrate the brain tissue without breaking. Characterization of Electrical Property of the Device FIGS. 4a to 4i are representations illustrating the characterization of the μNTron in vitro. Specifically, FIG. 4a is a cyclic voltammogram of the DMA/PEDOTS-IPN hydrogel in PBS; FIG. 4b is measured CSC (vs. CV cycle number) of the DMA/PEDOTS-IPN hydrogel in PBS (n=3); FIG. 4c shows impedance at different frequency in PBS (n=3), in which the subset denotes the impedance (1000 Hz) of μNTron after submerged for a prolonged period (n=3); FIG. 4d is a graph of representative recording of square waveform (left) using μNTron (middle) and tungsten electrode (right); FIG. 4e is a diagram of voltage-driven delivery using biomimetic agarose gel, in which the molecules are released into the agarose, and the sample is collected by centrifugation for quantification using spectrometer; FIGS. 4f-4g show voltage-driven controllable release of GABA (1 mg/mL) from a single microneedle of μNTron as a function of different voltage (f) and duration (g) (n=3); FIG. 4h shows a comparison of passive diffusion (in release equilibrium state, >1 day) and voltage driven release (200 mV, 3 min; n=3); and FIG. 4i shows repeated voltage-driven release of GABA (200 mV, 3 min) from a single microneedle of the μNTron for multiple times (release amount/cycle: orange line, left axis; cumulative release percentage: red line; remaining amount: blue line, right axis). All error bars denote the s.d. * for p<0.05, *** for p<0.001 by test.

To characterize the electrochemical stability of the μNTron device, cyclic voltammetry (CV) was performed. The voltammogram remained to be well overlapped even after 100 sweeping cycles in PBS. Please see FIG. 4a. The device stability was further assessed by measuring the charge storage capacity (CSC), which was only slightly increased after 20 cycles, and was plateaued at a level of less than 2% increment after 100 cycles (35.11±0.3 mC cm², see FIG. 4b). When placed in PBS, the electrochemical impedance of the device showed a steady decrease against increasing scanning frequency from 1 to 1000 Hz (see FIG. 4c). The impedance stabilized at a level around 100 kΩ after being tested for more than 7 days (see FIG. 4c), which is comparable to the traditional tungsten electrode (0.1~5 MO). At different frequencies, a similar response in the square waveform recording was observed, when comparing the μNTron device to tungsten electrodes (see FIG. 4d).

Voltage-Driven Release of Biomolecules

Figure 10A:
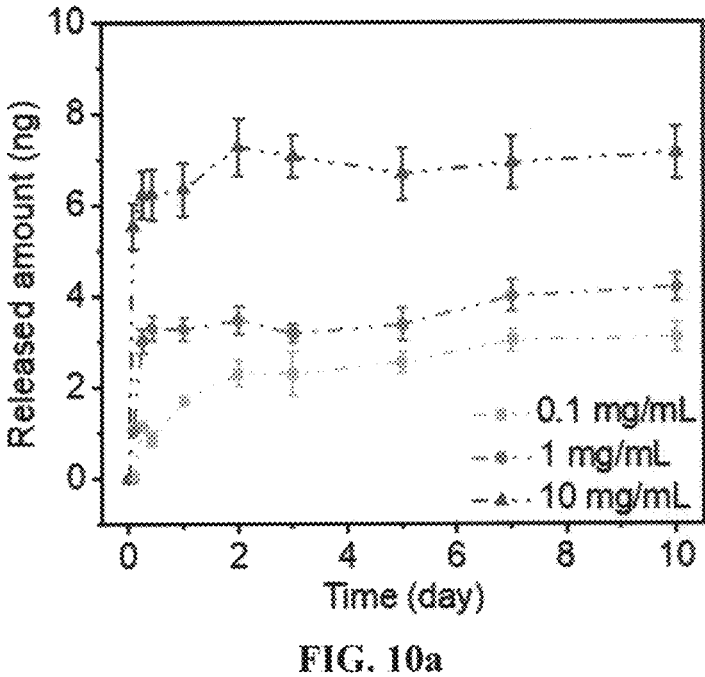
FIGS. 10a to 10c are graphs illustrating the administration of a therapeutic agent from an embodiment of an electronic device according to the present invention.
Figure 10B:
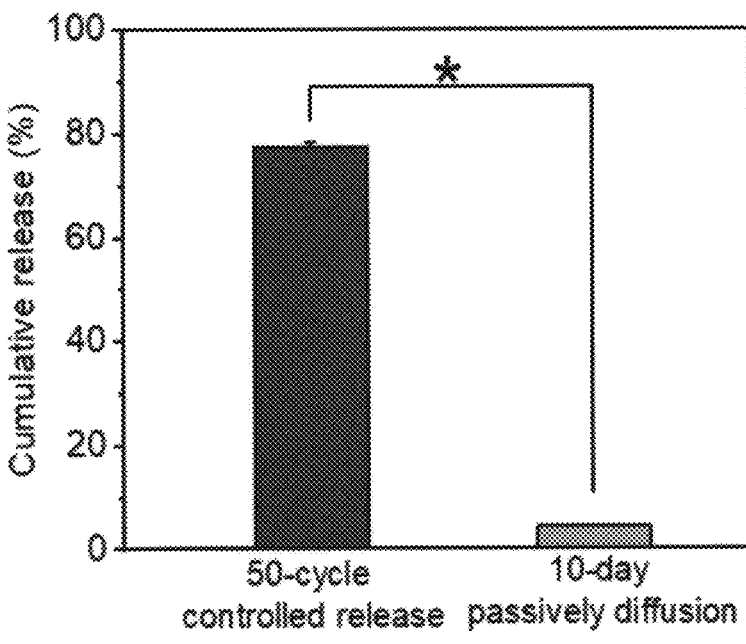
Figure 10C:
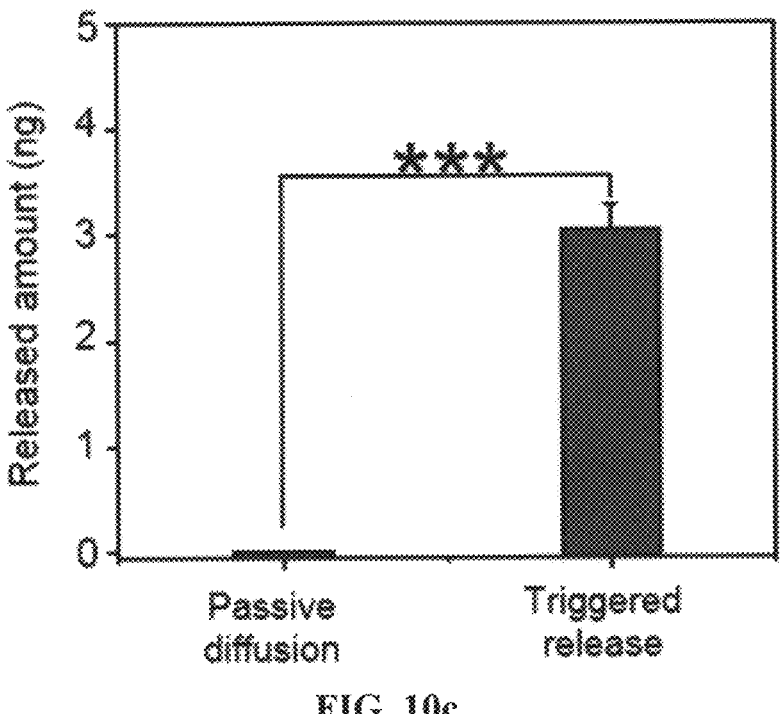

To evaluate the voltage-driven release of biomolecules ex vivo, a block of agarose gel (1.5% w/w in PBS) was used as a biomimetic substrate to mimic the device-tissue interface. In this assay, the released biomolecules were collected and then analyzed by spectroscopy (see FIG. 4e). A neural inhibitor, GABA, was preloaded within the porous hydrogel microneedles. The encapsulated GABA molecules can be released by electro-osmosis upon the application of voltage. While a slight leakage release was be observed (FIGS. 10a-10c), especially in the first 24 hours of the assay, the diffusion based escape of GABA molecules was observed to be associated with the encapsulation dose and was insufficient to change the physiological condition. For example, given an encapsulation of GABA at 1 mg/mL, the cumulative escape of GABA was only 3.29±0.26 ng after 24 hours, which cannot even alter any spontaneous neural activity. FIG. 10a shows cumulative passive release from a microneedle electrode with different loading concentrations of GABA; FIG. 10b shows comparison of the releasing amount from 50 cycles of voltage driven release (200 mV, 3 minutes, 50 cycles) or 10 days passive release, and FIG. 10c shows comparison of the triggered release (200 mV, 3 min) and the leaky release (passive diffusion, 3 min) from an electrode of the μNTron device.

Figure 11A:
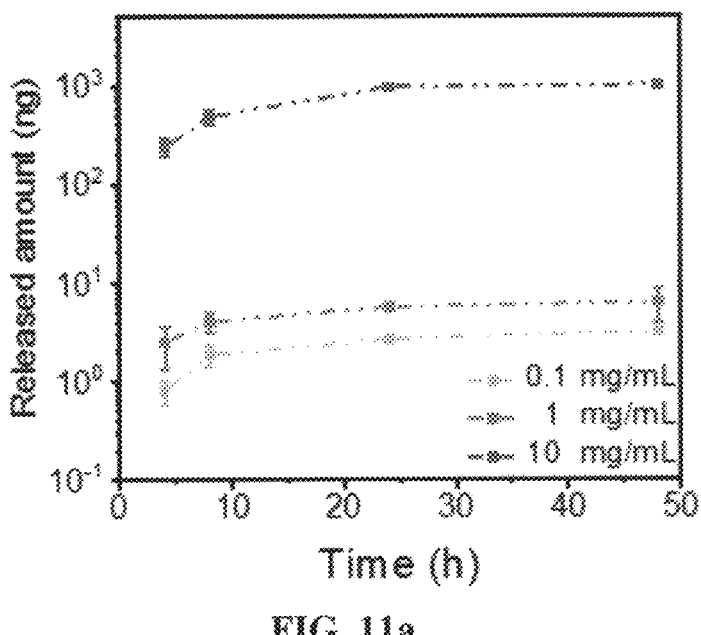
FIGS. 11a to 11f are graphs illustrating administration of a therapeutic agent via an electronic device of the present invention under different circumstances.
Figure 11B:
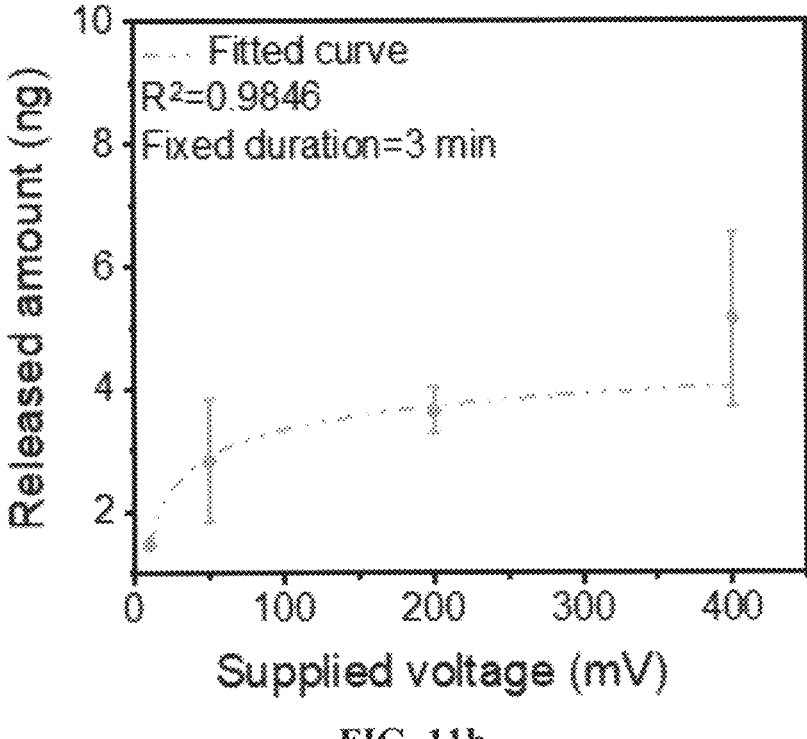
Figure 11C:
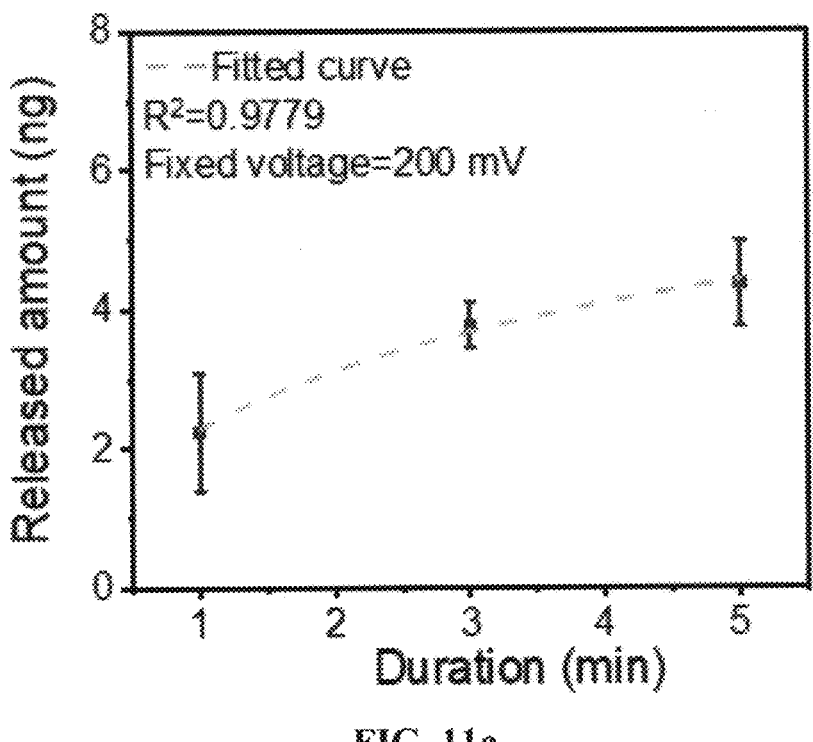
Figure 11D:
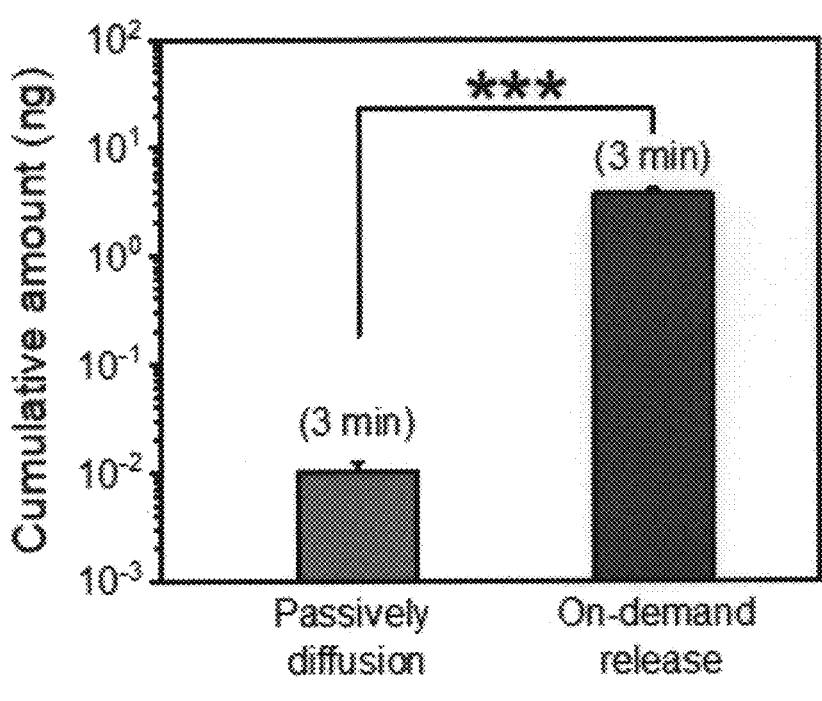
Figure 11E:
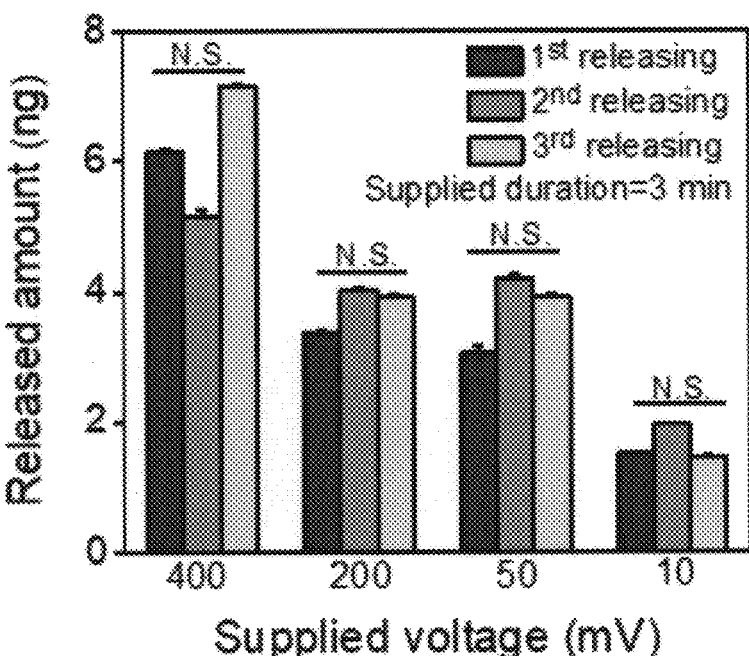
Figure 11F:
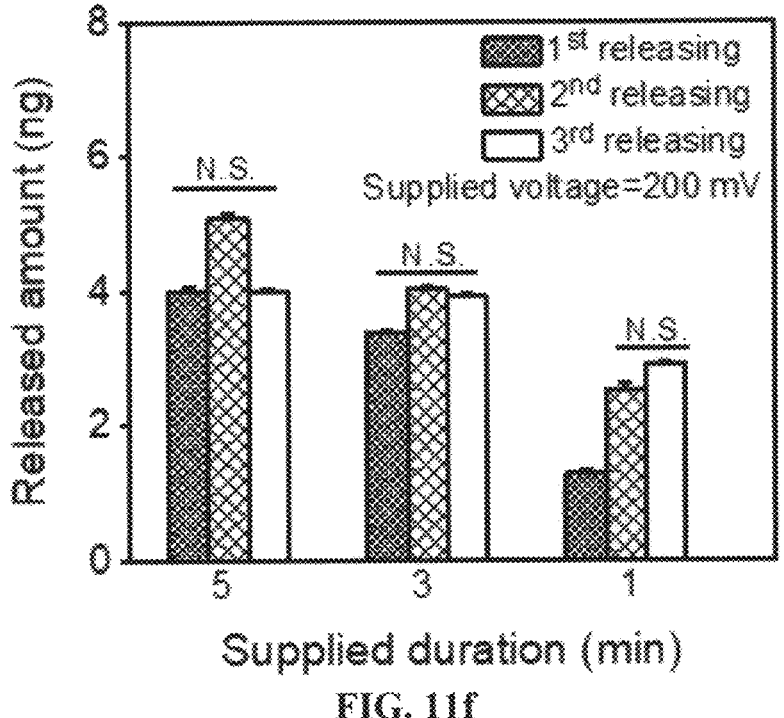

For the active voltage-driven response, a dynamic control of the releasing profile can be programmed by adjusting the amplitude and duration of the applied voltage stimulation. The DMA/PEDOTS-IPN hydrogel based microneedles can sustain a voltage up to 600 mV for 3 minutes to trigger a pulsed GABA release of 3.19±0.13 ng (see FIG. 4f). At a fixed stimulation voltage of 200 mV varying from 1 to 5 minutes, the release showed a positive correlation with the stimulation duration, ranging from 2.91±0.13 ng to 3.36±0.14 ng (see FIG. 4g). Thus, a single pulsed release from the μNTron device would be at least three order of magnitudes more than the release by passive diffusion within the same temporal window (see FIG. 4h), suggesting a drug administration process dominated by the active voltage-driven process. In addition to GABA, similar active releasing dynamics was also observed for other molecules (see FIGS. 11a to 11f). FIG. 11a shows cumulative passive release from a microneedle electrode with different loading concentrations of fluorescein (n=3); FIGS. 11b-c shows control of the voltage-driven release of fluorescein (1 mg/mL loading concentration) from a single electrode by varying the voltage (b) or stimulation duration (c) (n=3); FIG. 11d shows comparison of the release amount from the passive diffusion or the active voltage (200 mV) driven process in a temporal window of 3 minutes; and FIGS. 11e-f show quantification of the cyclic voltage-driven release of fluorescein (1 mg/ml loading concentration) from a single microneedle electrode using different voltage stimulation amplitude (e) and duration (f) (n=3). The error bars indicate s.d. *** for p<0.001, NS, not significant by student t-test.

In a cyclic stimulation up to 50 cycles (200 mV, 3 minutes), the device still showed excellent electrochemical responsiveness, though the absolute releasing dose was observed to drop due to a reduction of the remnant GABA molecules in the microneedle hydrogel electrodes (see FIG. 4h). A consistent administration dose can potentially be compensated by programmed adjustment of the stimulation parameters (e.g. voltage and duration). After 50 stimulation cycles, the cumulative drug release from a μNTron device was around 77.55% of the preloaded amount. Without any triggers, less than 5% of the preloads can be released even after an assay of 10 days (see FIGS. 10a-c), suggesting an excellent drug encapsulation and a well-controlled drug administration using the μNTron device.

Closed-Loop Anti-Seizure Strategy

To test the μNTron device in vivo and to implement a closed-loop strategy to treat brain disease, a seizure animal model was established by injection of 4-ap (25 mM, 500 nL) to one-side of the somatosensory cortex of a mouse brain to reproduce the seizure propagation and occasional outburst. A μNTron device was placed near the injection site with a posterior offset for neurophysiology recording and pharmaceutical intervention (see FIG. 12, which are the two majors functions mutually affecting each other in closed-loop for intelligent management of seizure occurrence. FIG. 12 illustrates the implantation of a device in a mouse brain. The brain skin was incised to expose the skull, and a 3×3 craniotomy window was opened by a dental microdrill. A hole was drilled (0.8 mm A/P and 0.2 mm M/L) to insert glass pipette for 4-ap injection. Two screws on the skull were used as the reference and ground electrodes, respectively. (scale bar: 2 mm)

Figure 5A:
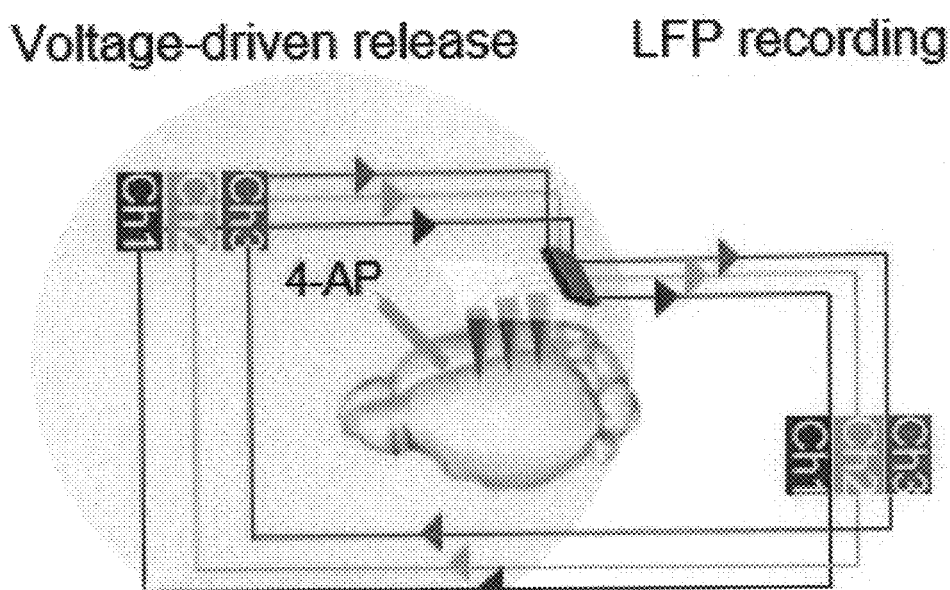
FIGS. 5a to 5j are schematic diagrams, graphs, and photographic images illustrating LEP mapping of elicited seizure and biocompatibility assay in an experiment using the electric device.
Figure 5B:
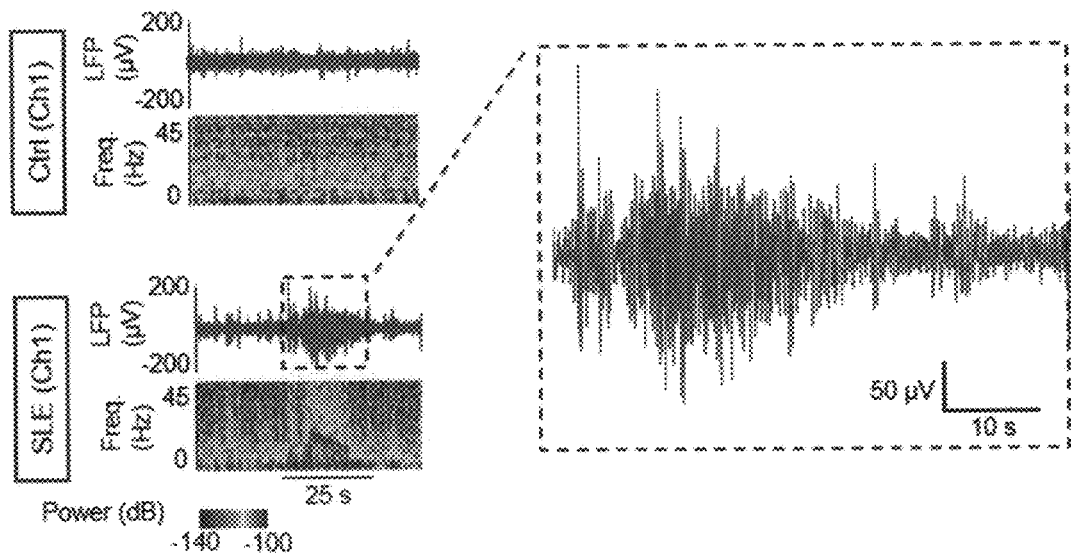
Figure 5C:
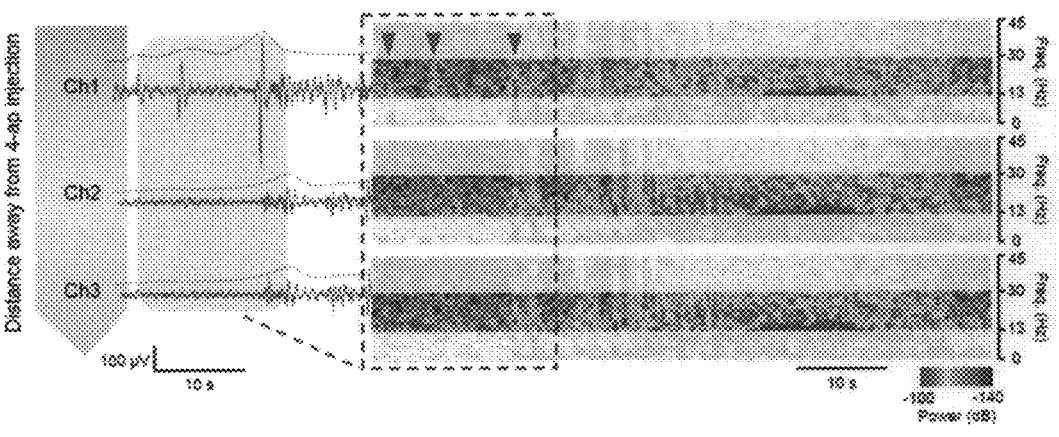
Figure 5D:
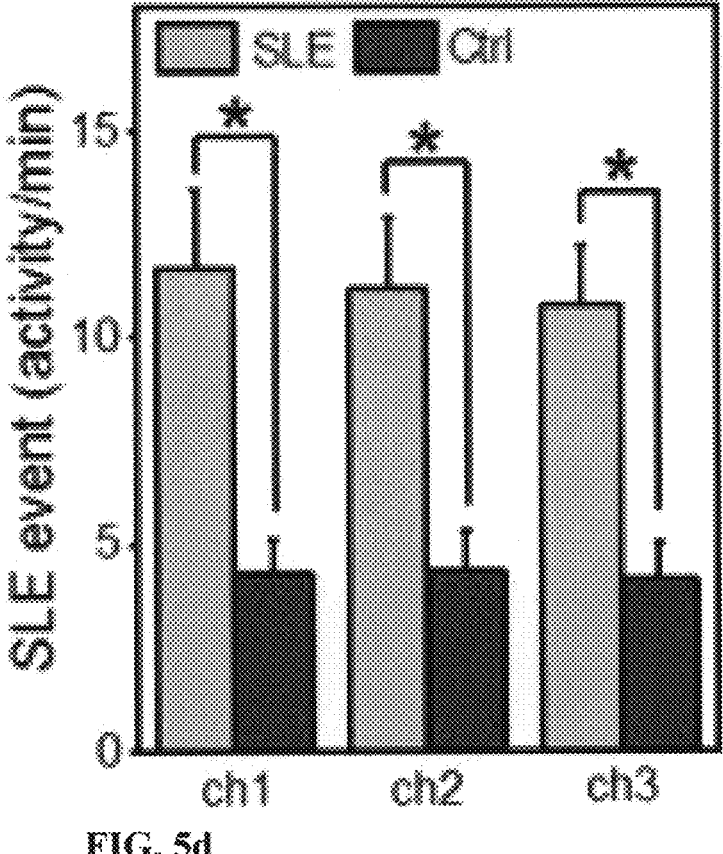
Figure 5E:
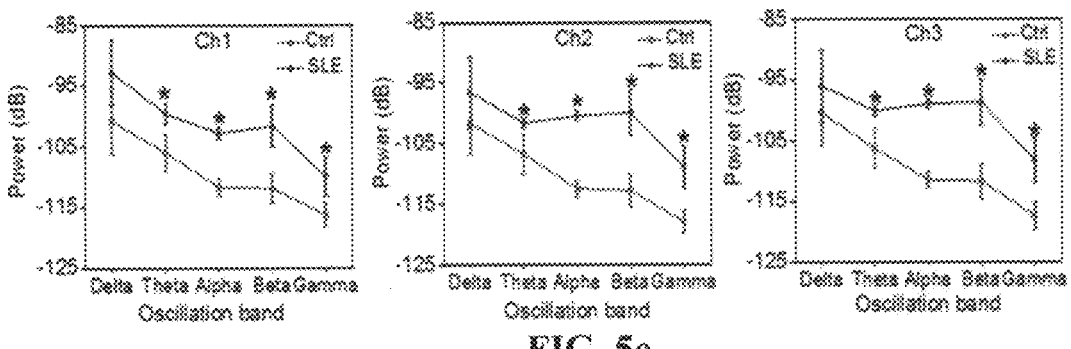
Figure 5F:
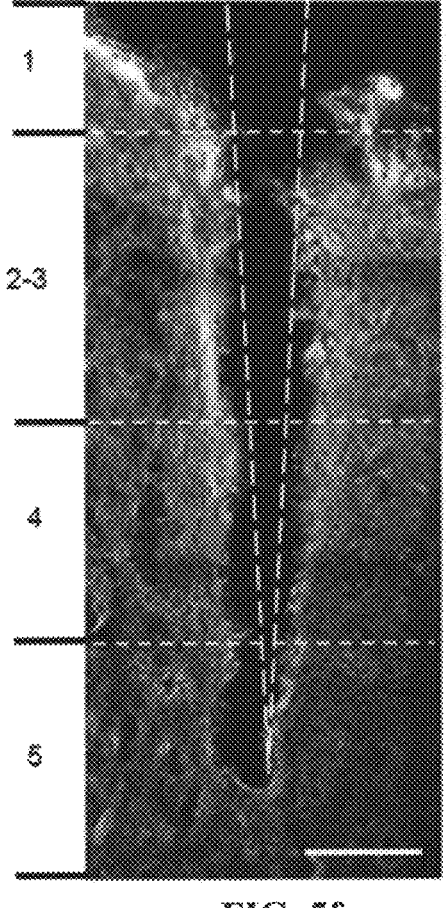
Figure 5G:
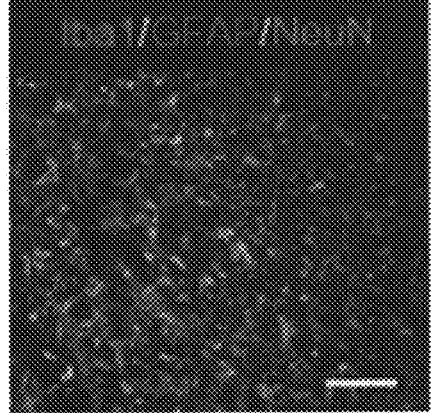
Figure 5G:
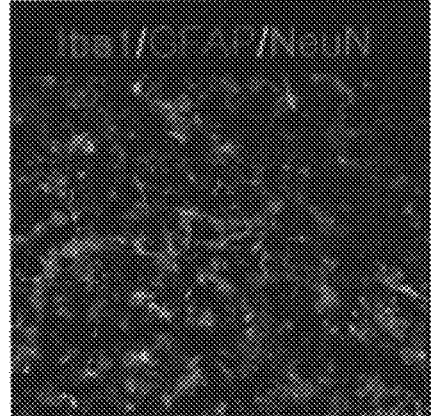
Figure 5G:
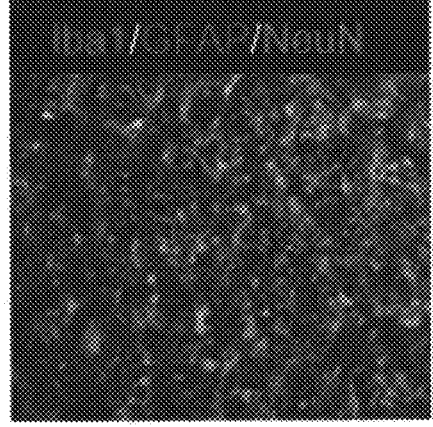
Figure 5H:
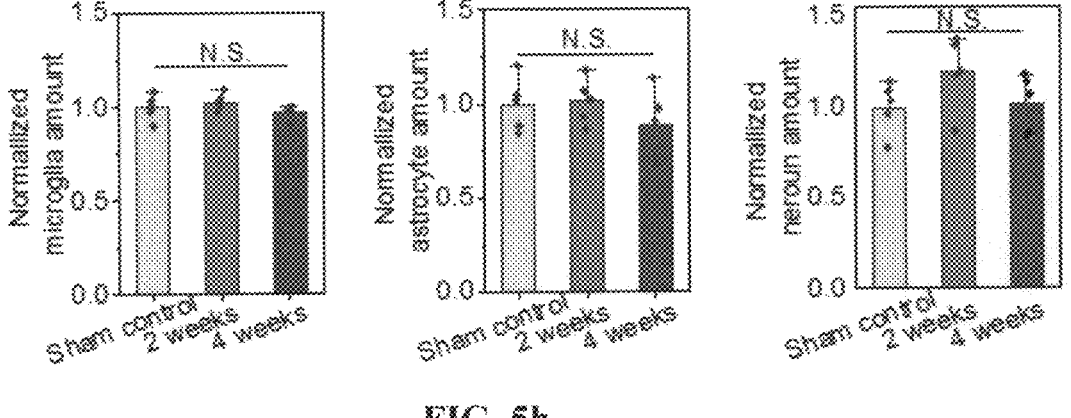
Figure 5I:
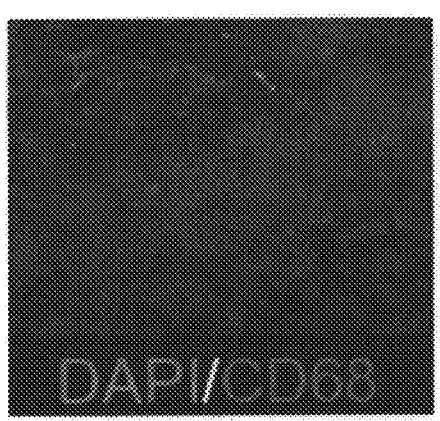
Figure 5I:
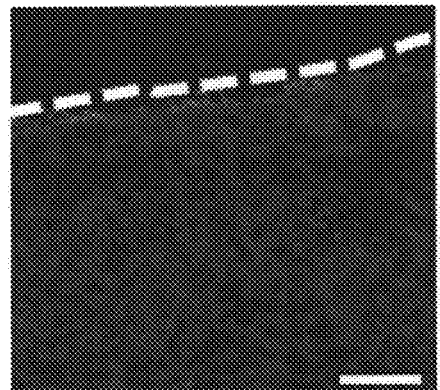
Figure 5I:
Figure 5I:
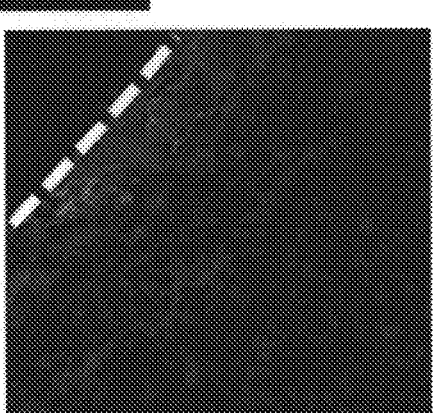
Figure 5J:
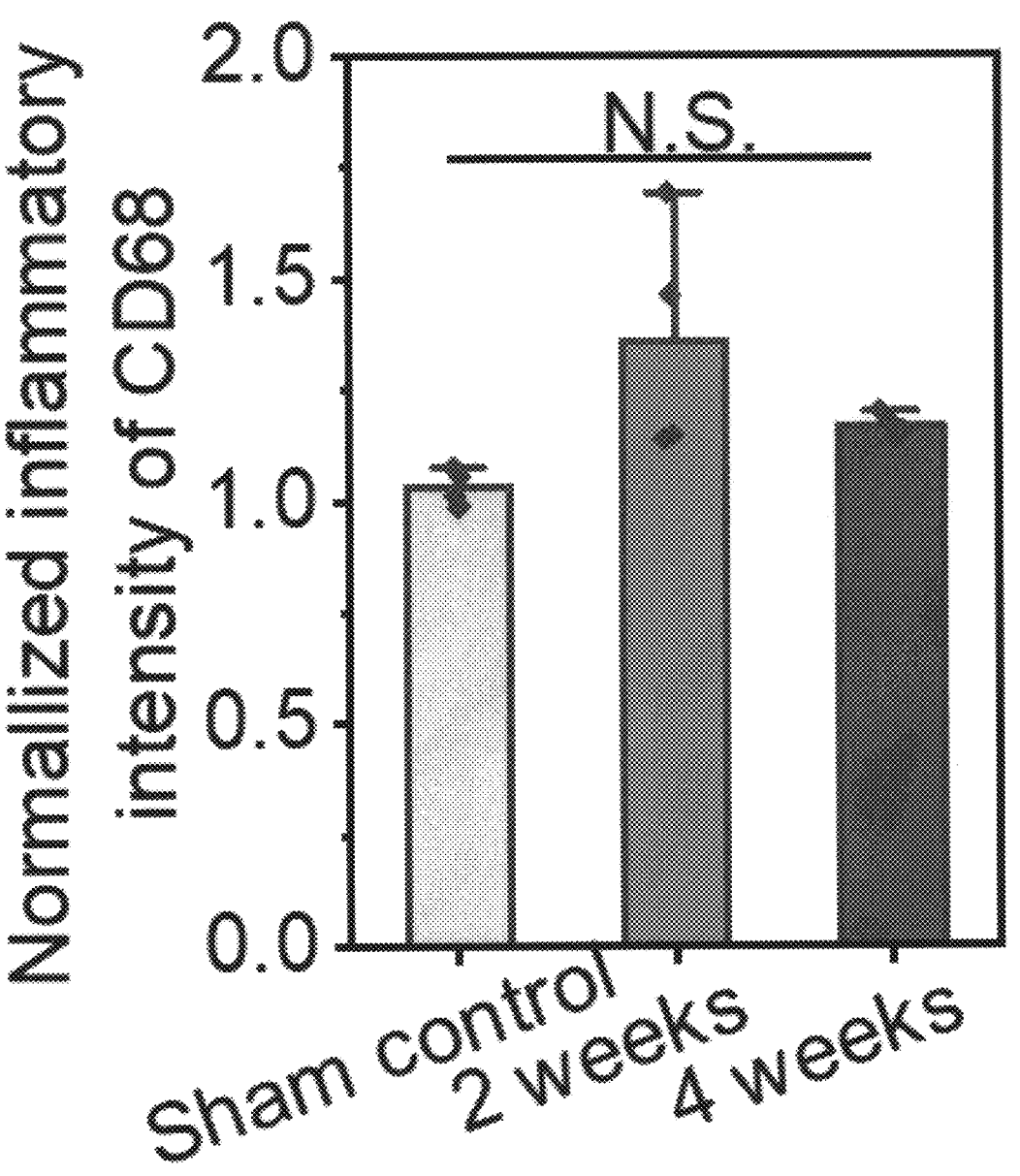

FIGS. 5a-j illustrate LFP mapping of elicited seizure and biocompatibility assay. Specifically, FIG. 5a is a schematic diagram of LFP mapping and seizure model in vivo. Three microneedles of μNTron align with the 4-ap infusion site in the anterior-posterior axis. The distance from 4-ap infusion site increases from Ch1 (2 mm), Ch2 (3 mm), to Ch3 (4 mm). FIG. 5b is a graph of the representative LFP recording (gray) and associated power spectrum (heatmap) of the control signal (upper panel) and the seizure signal (lower panel). FIG. 5c is a graph of representative LFP mapping in a typical SLE. The distance from 4-ap infusion site increases from Ch1, Ch2 to Ch3. FIG. 5d is a graph of statistical analysis of neural activity (above LFP recording baseline) in three different channels (n=5). FIG. 5e are graphs showing the power analysis of LFP recording in the control (red) and the seizure (blue) (n=5). FIG. 5f is an image of representative fluorescence microscopy images of coronal brain after μNTron insertion. (red for Iba1, green for GFAP, and blue for NeuN). Scale bar, 100 μm. FIG. 5f are images of representative fluorescent microscopic images of μNTron implanted regions after 2 weeks and 4 weeks. Scale bar, 50 μm. FIG. 5h are graphs showing statistics analysis of immune responsive in implanted region (n=5 from 3 mice). FIG. 5i are images of coronal brain slices of a μNTron implanted regions labelled by the inflammatory biomarker CD68 for the sham control, 2 weeks and 4 weeks. Scale bar, 50 μm. FIG. 5j is a graph of statistics analysis of immune responsive in implanted region (n=5 from 3 mice). All error bars denote the s.d. * for p<0.05, NS, not significant by test.

Figure 13A:
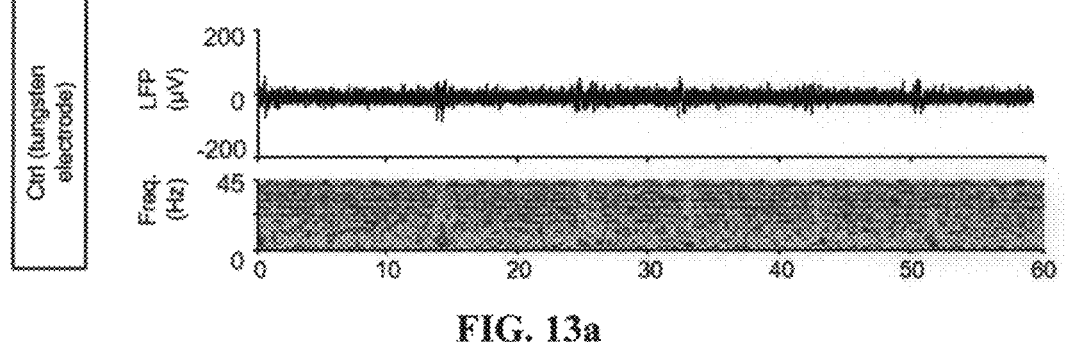
Figure 13B:
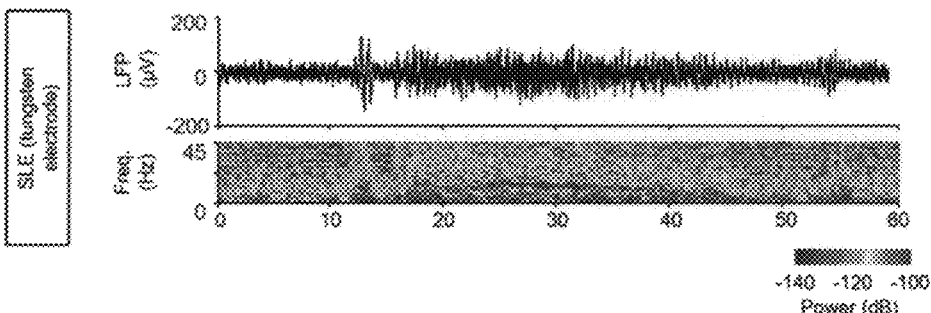
Figure 13C:
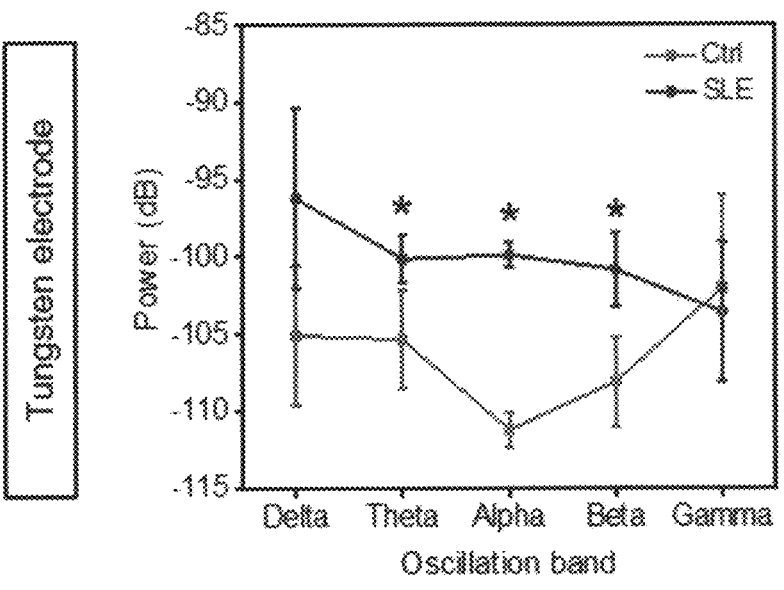
Figure 13D:
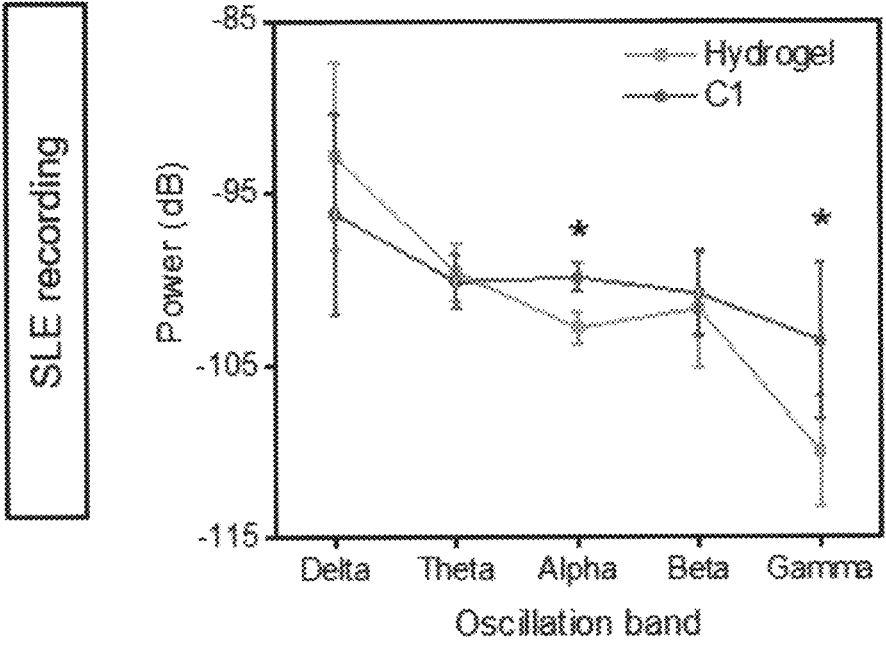
Figure 13E:
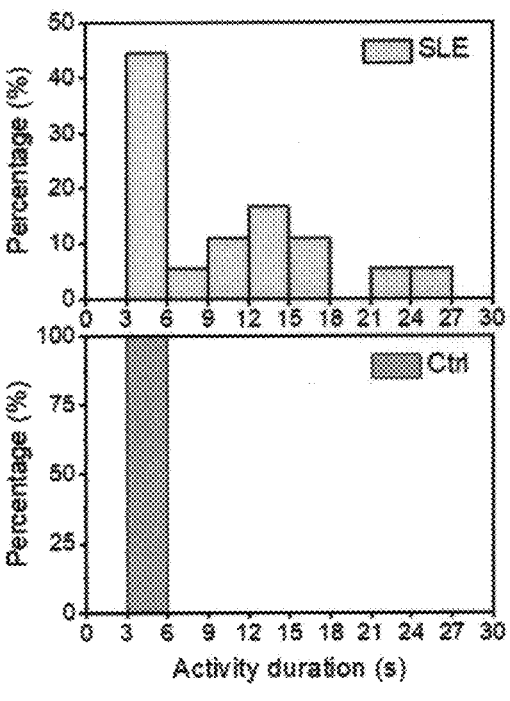

After an initial evaluation of 4-ap induced abnormal neural spiking, out of the night active electrodes, three most affected microneedle channels (Ch1, Ch2, and Ch3) with an offset of 2-, 3- and 4-mm posterior to the injection site were selected for surveillance purpose in this experiment. Upon the injection of 4-ap, a surge of neural spiking was clearly observed by electrical recording of local field potential (LFP), and was elaborated by the associated Fourier-based power spectrum (FIG. 5b). The multi-channel recording provides a spatial and temporal differentiation to show a directional propagation of induced high frequency spiking activity from the 4-ap injection site, which was firstly detected by Ch1 and subsequently by Ch 2 and Ch3 (FIG. 5c). Because of the immediate proximity to the injection site, Ch1 recording was selected as the major source for the feedback signal to capture the onset of a seizure outburst, which would otherwise spread to a wider cortical region without any pharmaceutical intervention (FIG. 5d). Similar recording was acquired using multiple tungsten electrodes, suggesting a comparable recording performance as the commercial electrophysiology system (see FIGS. 13a-d). FIGS. 13a-b illustrates the representative LFP recording from a normal mouse (FIG. 13a) or an epileptic mouse (FIG. 13b) by tungsten electrodes and associated power spectrum FIG. 13c shows quantitative power analysis of LFP recordings from normal (red) or epileptic (blue) animals, the recordings were performed by using the commercial tungsten electrodes (n=5); and FIG. 13d illustrate a direct comparison of the LFP power spectrum acquired by using our μNTron device (orange) or tungsten electrodes (gray) (n=5). The error bars indicate s.d., * denotes p<0.05 by student t-test.)

For predictive feedback to control the drug administration process and to combat a monolithic propagation of a seizure event from the origin point, a quantitative analysis of the LFP recording was derived to improve the anti-seizure management. For example, the power analysis confirmed an up-regulation of neural spiking activity at various oscillation frequencies (δ for 1~4 Hz, θ for 4~8 Hz, α for 8~13 Hz, β for 13~30 Hz, γ for 30~70 Hz, FIG. 5e and FIG. 14, which is consistent with the documentation by previous studies. FIG. 14 shows the spectrum power analysis of neural oscillation frequency (δ for 1~4 Hz, θ for 4~8 Hz, α for 8~13 Hz, β for 13~30 Hz, γ for 30~70 Hz) for signal acquired from normal (Ctrl) or epileptic (SLE) animals.

When taken out from the mouse brain after recording (>3 hours), the organic microneedle electrodes on the μNTron device exhibited well-preserved structural and morphological integrity. Please see FIG. 15. FIG. 15 is the photogram of showing a μNTron device after being used in a mouse brain. Scale bar, 500 μm. FIG. 16a-b are images of representative histological staining for H&E (FIG. 16a) or Nissl blue (FIG. 16b) in the coronal section brain tissues, showing the trace of electrodes implantation (scale bar, 100 um).

At the implantation site, the trace of tissue penetration by the hydrogel microneedles could be clearly observed. Please see FIGS. 16a-b and FIG. 5f. The preserve of healthy nerve cells at the device-tissue interface suggested a good biocompatibility and minimum invasiveness resulted from the device implantation, which was further evidenced by a chronic assay up to 4 weeks long (see FIGS. 5f-j). In comparison to the negative control (no implant), there were no significant changes in the microglia, astrocyte, or neuron recruitment to the regions nearby the penetration site. We also characterized the level of the immune response by measuring the expression of an inflammatory biomarker, tumor necrosis factor CD68. The organic μNTron device caused negligible inflammatory response over the one-month period, though a slightly more inflammation was observed 2 weeks after implantation (see FIGS. 5i-j). These results demonstrate a superior biocompatibility of the μNTron device based on conductive hydrogels, which is essential for long-term in vivo applications in management of chronic diseases. The in vivo electrical recording also proves the feasibility for effective and accurate temporospatial surveillance of neural activity that allows for real-time and efficient feedback in a closed-loop to control the drug releasing events.

Intelligent Anti-Seizure Management

As a proof-of-concept for a closed-loop neuro-treatment that combines electrical recording and controlled drug administration, the μNTron device for the anti-seizure management in epileptic animals was tested on. Depending on how the feedback signal is processed, two different triggering modes, "prevention" or "clearance", were implemented for GABA releasing to combat seizure outburst, emphasizing the critical timing and dose to execute an on-demand pharmaceutical intervention (FIGS. 6a-d). Please see FIGS. 6a-d show the timeline of "prevention" (FIG. 6a) or "clearance" (FIG. 6c) pharmaceutical intervention for anti-seizure treatment. The LFP recording and the associated power spectrum showing the therapeutic efficacy of a "prevention" (FIG. 6b) or "clearance" (FIG. 6d) drug administration. In the "prevention" mode, the voltage-driven GABA release from the hydrogel electrode was executed at an earlier stage when the onset of an SLE was detected after 4-ap injection (FIG. 6a-b), as indicated by a 3.5% or greater power increase of the β oscillation at Ch1 (see FIGS. 17a-b). FIGS. 17a-b show real-time local field potential (LFP) recording (FIG. 17a) and frequency analysis (FIG. 17b). The examined neural oscillation frequencies include δ for 1~4 Hz, θ for 4~8 Hz, α for 8~13 Hz, β for 13~30 Hz, and γ for 30~70 Hz. The signals were evaluated every 5 seconds. Upon triggering, about 3 ng GABA was released by a voltage trigger at 200 mV for 3 minutes. As a result, only a slight expansion of the SLE was observed in the following 30 minutes of continuous surveillance by electrophysiology recording (see FIGS. 6*a-b*).

In the same setup, a blank delivery (no GABA included) was not able to achieve a similar blockage of SLE progress (see FIGS. 18*a-d*), confirming a therapeutic effect resulted from the triggered pharmaceutical intervention, instead of from the voltage stimulation. FIG. 18*a* is a graph showing quantification of SLE events in epileptic animals without any treatment or being treated with a blank device (no GABA) (n=6); FIG. 18*b* is a graph showing the power spectrum analysis of the LFP recordings in epileptic animals without any treatment or being treated with a blank device (no GABA) (n=6); and FIGS. 18*c-d* are graphs showing the analysis of the duration SLE activity in untreated (FIG. 18*c*) and blank device (FIG. 18*d*) cases. The size of each bin is 1 second. All error bars denote the s.d. NS, not significant by student t-test.

In the "clearance" mode (see FIG. 6*c*), a voltage-driven GABA release was executed at a later stage (15 minutes after 4-ap injection) when a SLE was fully developed and was observable in the recording form multiple channels FIG. 19). In the "clearance" mode, a voltage-driven GABA release was executed 15 minutes after 4-ap injection, when an SLE was fully developed and was clearly observable in the recording from multiple channels. Quantitatively, an SLE was defined as a more than 6% power increase of β oscillation (13-30 Hz) in neural firing. Following the delivery of 3 ng GABA (same as in the "prevention" mode), the number evoked SLEs were reduced but still noticeable in the post-delivery recording (see FIG. 6*d*).

Figure 6A:
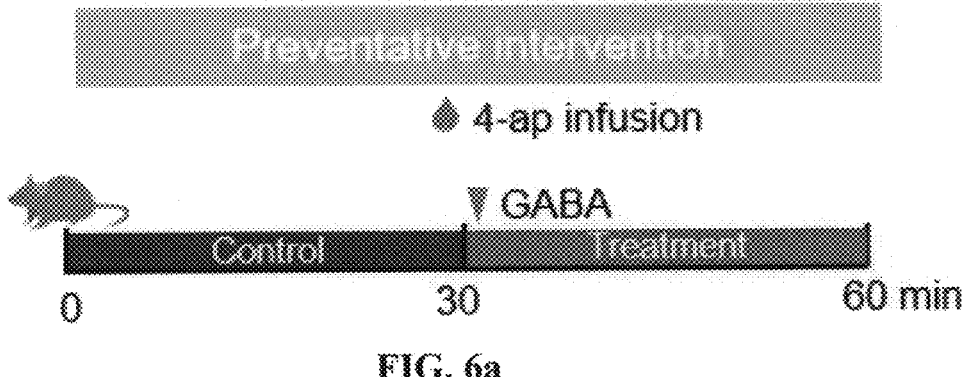
FIGS. 6a to 6h are representations and graphs showing an embodiment of system using a closed-loop methodology to manage seizure of a subject.
Figure 6B:
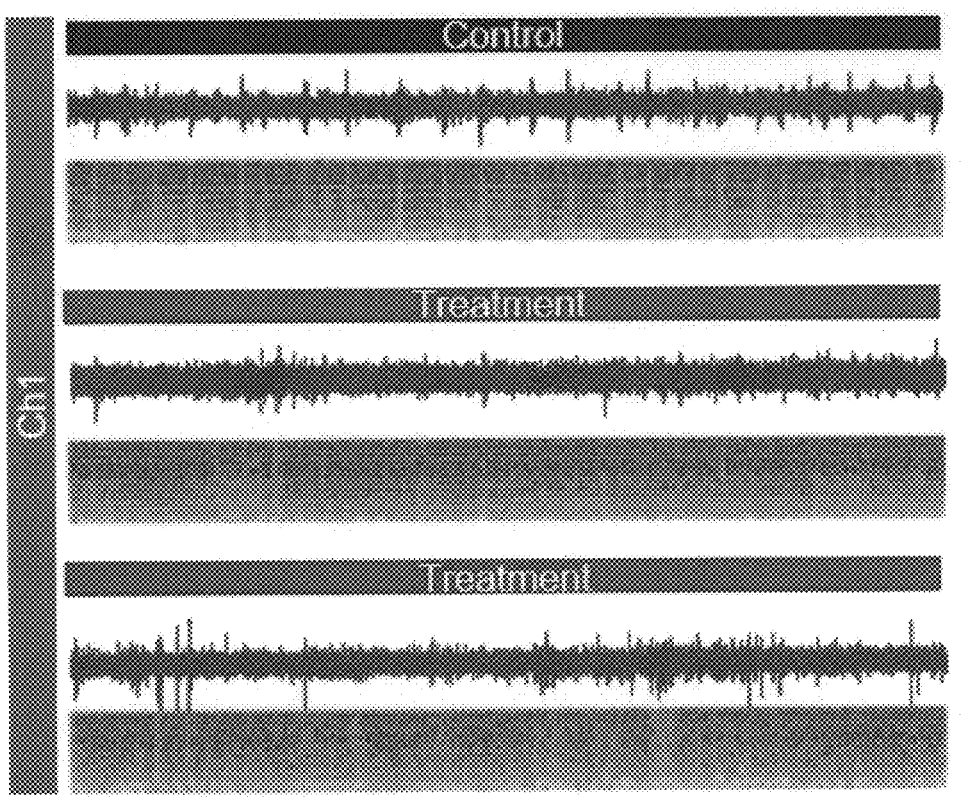
Figure 6C:
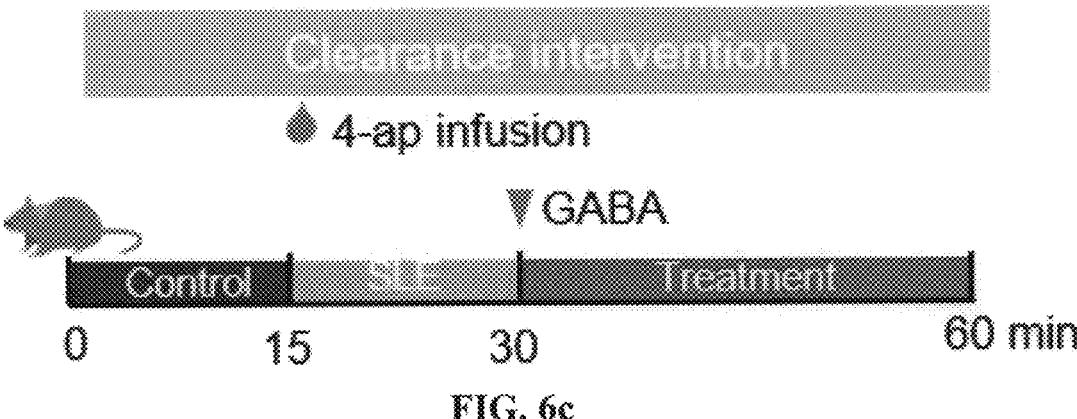
Figure 6D:
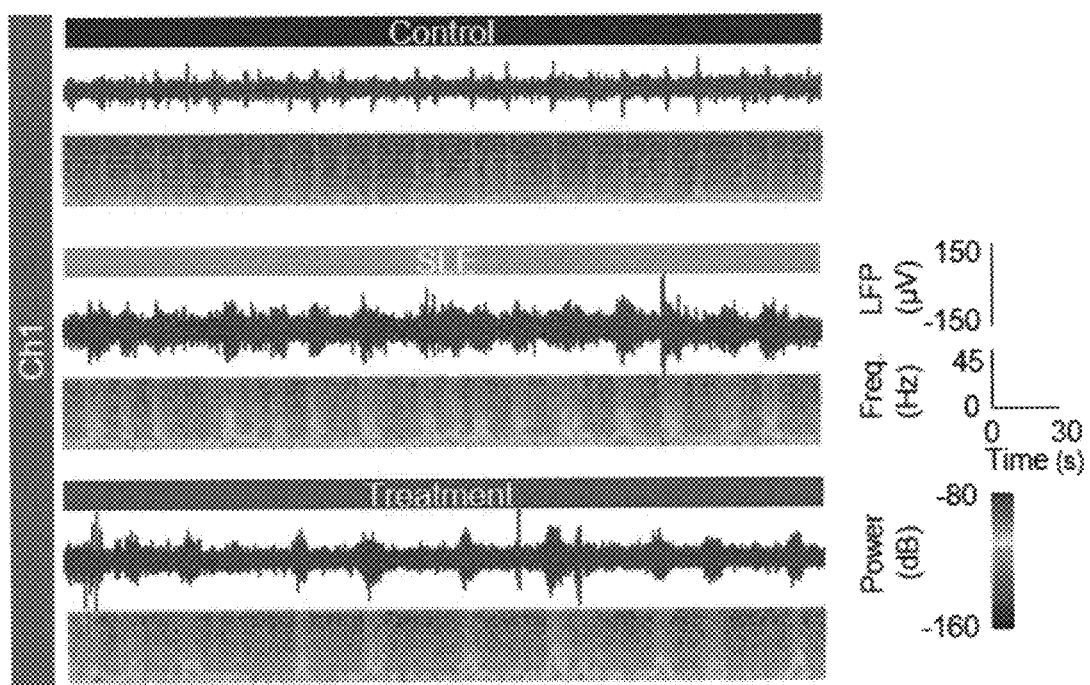
Figure 6E:
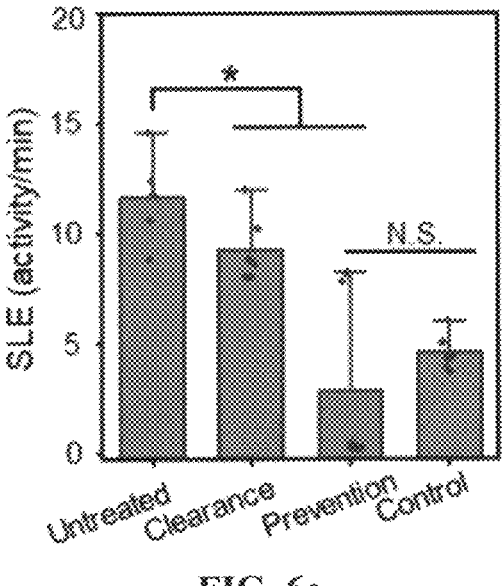
Figure 6F:
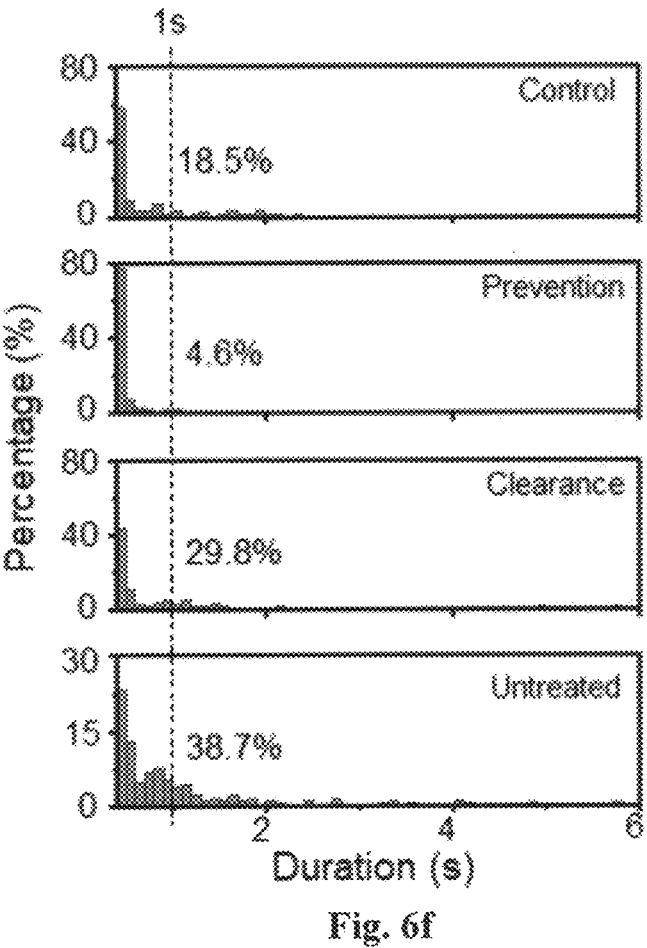

Compared to untreated cases, either "clearance" or "prevention" intervention was able to lower the number of SLEs, which was reduced by 20.6±1.6% in the "clearance" and more significantly by 75.7±4.0% in the "prevention" strategy (see FIG. 6*e*). Similar observation could also be made directly in the LFP recordings. The portion of abnormal sustained firing events (>1 seconds) was substantially reduced (see FIG. 6*f*), which would otherwise account for more than 38% of the total spikes in untreated animals. FIG. 6*e* shows the quantification of the reduction of SLEs in epileptic animals using different anti-seizure strategies ("clearance" or "prevention"). FIG. 6*f* show the histogram analysis of the duration of LFP spiking activity, the temporal bin size is 0.1 seconds. For FIG. 6*e-f*, untreated and normal animals are used as positive and negative controls, n=6, the error bars denote the standard deviation, * indicates p<0.05, NS, not significant by student t-test.

Figure 6G:
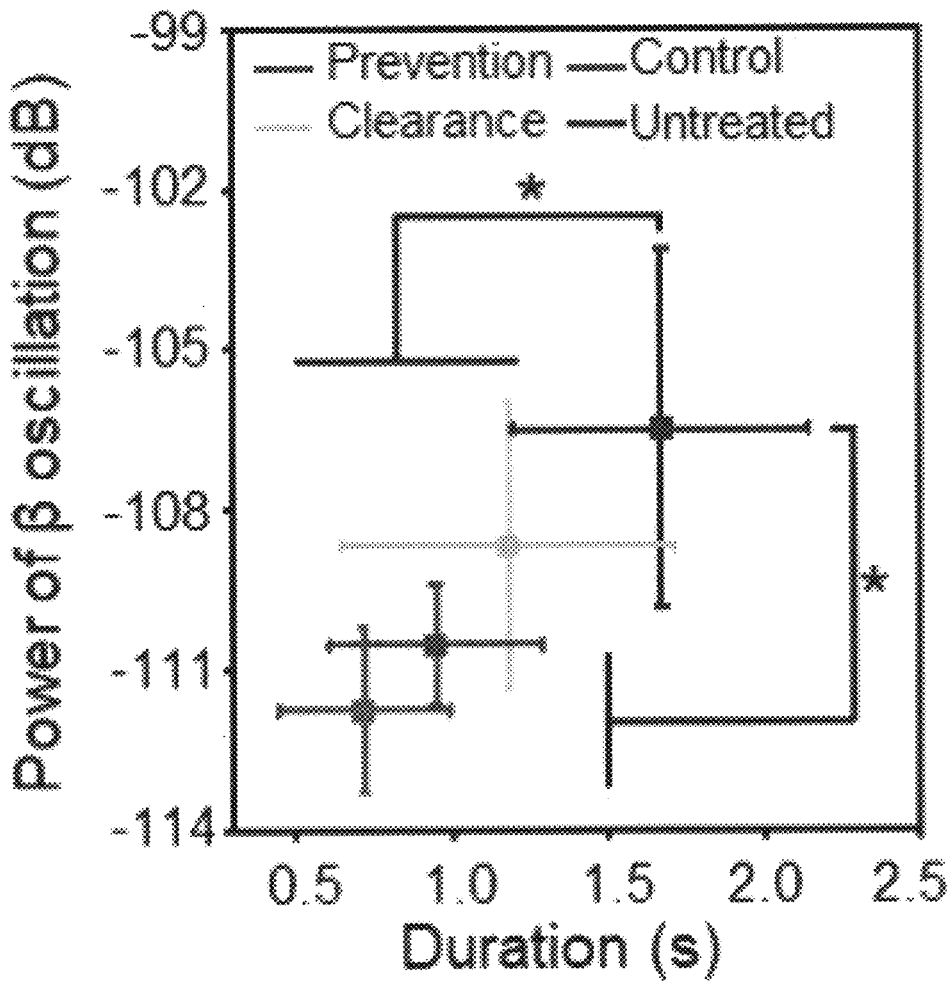
Figure 6H:
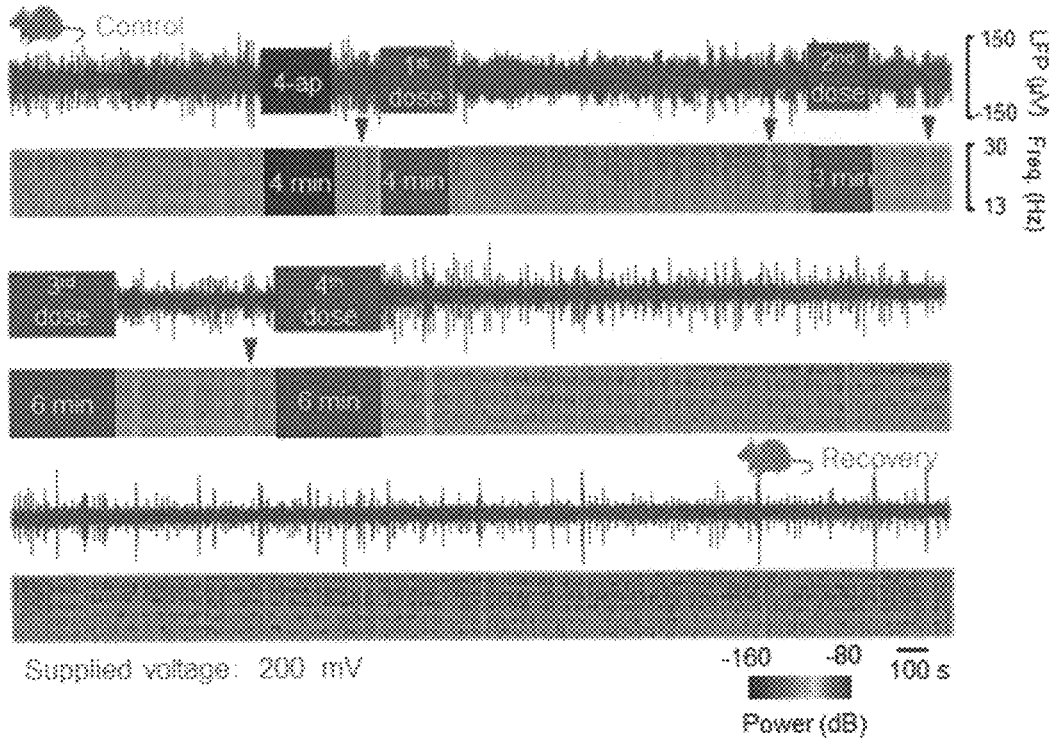

While both "prevention" and "clearance" interventions are useful in anti-seizure management, a predictive strategy is clearly more effective, emphasizing the importance of timing and dose of drug administration in the therapeutic practice, which can be controlled by a more intelligent processing of the feedback signal in a closed-loop neuro-treatment enabled by the μNTron device (FIG. 6*g*). FIG. 6*g* show the analysis the amplitude and duration of abnormal β oscillation (13~30 Hz) in different treatment strategies. Towards this end, the "prevention" strategy was further extended by the inclusion of a self-adaptive adjustment of the GABA administration in longer experiments (FIG. 6*h*). In addition to a real-time extraction of the power analysis of the 3 SLEs as the trigger for GABA release (see FIGS. 17*a-b*), the drug dose was also adjusted by varying the duration of a voltage trigger to compensate the power variation (β oscillation) of a detected SLEs. The relationship between the increase ratio of β SLEs above the control baseline and supplied voltage duration has been exploited which could be regarded as a reference to guide regulate real-time pathological behaviors (see FIG. 20). FIG. 20 shows the adaptive dosing control by varying voltage stimulation (200 mV, 3~6 minutes) based on the change of β oscillation amplitude to trigger drug release from individual electrodes of a μNTron device.

In this way, an animal can go back to almost normal from a seizure outbreak after 4 brief GABA administrations in a few hours with a total dose of just ~13 ng, which would otherwise require continuous maintenance of a relatively high blood concentration by traditional drug administration methods.

The present invention has demonstrated a closed-loop strategy for intelligent neuro-treatment using multifunctional organic electronics. The core component is based on a single-component and multi-functional organic device, μNtron, which can be used to perform electrophysiology recording and to control in vivo drug release. In the closed-loop neuro-treatment, the two functions are connected by a feedback mechanism, where the recorded electrophysiological signal is analyzed and extracted as a trigger to control a voltage-driven drug release process; conversely, the pharmaceutical intervention rescues the brain tissue from abnormal conditions (e.g. seizure outbreak), which is further reflected by continuous surveillance of neural activities. In epileptic animals, the closed-loop strategy was successfully used for intelligent anti-seizure management, in which the timing and dose of pharmaceutical intervention was adaptively determined by a predictive analysis of cortical spiking conditions.

From a material perspective, the μNtron device was fabricated from a photo-polymerizable conductive IPN hydrogel using the biocompatible DMAPS and PEDOT:PSS as the major components. Unlike many other conductive hydrogels that typically need specific crosslinking agents to link conductive monomers and polymerize monomers separately to balance the conductivity and mechanical stability, the use of DMAPS simplifies the synthesis process and forms a hydrogel framework by a one-step in situ polymerization without post-processing. Besides acting as the main monomer composition of second polymerize network for enhancing S also acts as the crosslinking agent to form the first conductive polymer network by physical crosslinking interaction with PEDOT+ hydrogel mechanical strength, the DMAPS. The sulfonic acid group was used electrostatically interact with PEDOT+; the acrylate group was used to form a stable polymer network with the PF127-DA, MBAA. Thus, just changing the DMAPS content is sufficient to vary the hydrogel crosslinking structure to render varying mechanical strength for tissue penetration, stable structure to resist deformation, and small micropores for drug encapsulation. At microscale, the electroactive hydrogel microneedles were strong enough to penetrate cortical brain tissue without compromising the structural integrity. At macroscale, the μNtron device has a flexible construction with a matching modulus to brain tissues, therefore ensuring a seamless integration with ridged brain surfaces for better signal transmission.

A denser crosslinked network also increases the ionic strength that can weaken the electrostatic attraction between PEDOT+ and PSS−, which increases the conductivity thought the π-π stacking of PEDOT+. Due to its good carrier mobility and electrochemical stability, PEDOT:PSS was used as a dopant in the hydrogel to improve the electrical performance. The increased conductivity is especially important for recording electrophysiological signal, this is because high conductivity could improve signal to noise ratio effectively. For electroactive chemical releasing, the release of charged drug is achieved through electrostatic interactions, with enhanced release observed upon reduction or oxidation of conductive polymer. The reaction builds up an electrical field for more efficient electro-osmosis of charged molecules, which were driven to migrate towards the electrode bearing opposite charges, leading to the escape of drug molecules from the hydrogel microneedles. For the µNtron device, a working voltage less than 200 mV was sufficient to drive necessary drug release. This triggering voltage is substantially lower than the required level (usually >800 mV) in electrophoretic techniques to achieve a similar releasing rate, and warrants a safe and long-term operation in brain tissues.

Synthesis of Crosslinker PF127-DA

Pluronic® F-127 (PF127) was acylated following a previously reported protocol {Zhao, 2018 #27}. Briefly, 5 g PF127 and 0.07 g triethylamine (J&K Chemical) were dissolved in 25 mL anhydrous dichloromethane in ice bath with N2 protection. 600 µL acryloyl chloride were slowly added to above solution in dropwise within 20 minutes. The mixture was then stirred for 24 hours, and the reaction temperature was gradually increased to room temperature (RT). The resulted product was concentrated by rotational evaporation to remove the solvent, then dialyzed (cut off molecular weight, 3500) against deionized water for three days. The purified product was obtained by lyophilization, and the chemical structure of PF127-DA was confirmed by FT-IR spectroscopy.

Synthesis of DMA/PEDOTS-IPN Hydrogels

To prepare the DMA/PEDOTS-IPN hydrogel precursor solution, DMAPS was slowly added to filtered PEDOT:PSS dispersion under constant stirring to induce gelation of PEDOT:PSS. The crosslinker PF127-DA, MBAA and photo-initiator Irgacure 2959 (3% of DMAPS and PF127-DA total solid mass) were dissolved in DI water and mixed with PEDOT:PSS solution (PF127-DA can be rapidly dissolved in DI water under ice-water environment). DMA/PEDOT-IPN hydrogels (14 wt % PF127-DA) of four different DMAPS content concentrations (10, 20, 30, and 40 wt %) were prepared in this study (see above Table S1). The polymerization of hydrogel precursor solution was induced by UV exposure (30 mW/cm$^{-2}$, 365 nm, Blak-Ray) for 25 minutes. DMA/PEDOT-IPN30 hydrogel was employed for the subsequent experiments and µNtron device fabrication.

The following references are incorporated in their entirety and a skilled person is considered to be aware of disclosure of these references.

Mage P, Ferguson B, Maliniak D, Ploense K, Kippin T, & Soh H, Closed-loop control of circulating drug levels in live animals. Nature Biomedical Engineering 1:1-10 (2017).

Srinivasan S S, Maimon B E, Diaz M, Song H, & Herr H M, Closed-loop functional optogenetic stimulation. Nature Communications 9:1-10 (2018).

Armstrong C, Krook-Magnuson E, Oijala M, & Soltesz I, Closed-loop optogenetic intervention in mice. Nature Protocols 8:1475 (2013).

Yu J, et al., Glucose-responsive insulin patch for the regulation of blood glucose in mice and minipigs. Nature Biomedical Engineering 4:499-506 (2020).

Li X, et al., A fully integrated closed—loop system based on mesoporous microneedles—iontophoresis for diabetes treatment. Advanced Science:2100827 (2021).

Bouthour W, Mégevand P, Donoghue J, Lüscher C, Birbaumer N, & Krack P, Biomarkers for closed-loop deep brain stimulation in Parkinson disease and beyond. Nature Reviews Neurology 15:343-352 (2019).

Merchant F M, et al., Real-time closed-loop suppression of repolarization *alternans* reduces arrhythmia susceptibility in vivo. Circulation: Arrhythmia and Electrophysiology 13:e008186 (2020).

Bergey G K, et al., Long-term treatment with responsive brain stimulation in adults with refractory partial seizures. Neurology 84:810-817 (2015).

Vonck K & Boon P, Epilepsy: closing the loop for patients with epilepsy. Nature reviews. Neurology 11:252-254 (2015).

Qazi R, et al., Wireless optofluidic brain probes for chronic neuropharmacology and photostimulation. Nature Biomedical Engineering 3:655-669 (2019).

Mickle A D, et al., A wireless closed-loop system for optogenetic peripheral neuromodulation. Nature 565:361-365 (2019).

Proctor C M, et al., Electrophoretic drug delivery for seizure control. Science Advances 4:eaau1291 (2018).

Joo H, et al., Soft implantable drug delivery device integrated wirelessly with wearable devices to treat fatal seizures. Science advances 7:eabd4639 (2021).

Grosenick L, Marshel J H, & Deisseroth K, Closed-loop and activity-guided optogenetic control. Neuron 86:106-139 (2015).

McGlynn E, Nabaei V, Ren E, Galeote—Checa G, Das R, Curia G, & Heidari H, The Future of Neuroscience: Flexible and Wireless Implantable Neural Electronics. Advanced Science:2002693 (2021).

Qu J, Zhao X, Ma P X, & Guo B, Injectable antibacterial conductive hydrogels with dual response to an electric field and pH for localized "smart" drug release. Acta Biomaterialia 72:55-69 (2018).

Ge J, Neofytou E, Cahill III T J, Beygui R E, & Zare R N, Drug release from electric-field-responsive nanoparticles. ACS Nano 6:227-233 (2012).

Hao L, et al., Spatiotemporal magnetocaloric microenvironment for guiding the fate of biodegradable polymer implants. Advanced Functional Materials:2009661 (2021).

English M A, et al., Programmable CRISPR-responsive smart materials. Science 365:780-785 (2019).

Xie K, et al., Organic electrochemical transistor arrays for real-time mapping of evoked neurotransmitter release in vivo. Elife 9:e50345 (2020).

Liu Y, et al., Soft and elastic hydrogel-based microelectronics for localized low-voltage neuromodulation. Nature biomedical engineering 3:58-68 (2019).

Liu J, et al., Genetically targeted chemical assembly of functional materials in living cells, tissues, and animals. Science 367:1372-1376 (2020).

Yuk H, Lu B, Lin S, Qu K, Xu J, Luo J, & Zhao X, 3D printing of conducting polymers. Nature Communications 11:1-8 (2020).

Chen J, Peng Q, Thundat T, & Zeng H, Stretchable, injectable, and self-healing conductive hydrogel enabled by multiple hydrogen bonding toward wearable electronics. Chem Mater 31:4553-4563 (2019).

Zhao X, Guo B, Wu H, Liang Y, & Ma P X, Injectable antibacterial conductive nanocomposite cryogels with rapid shape recovery for noncompressible hemorrhage and wound healing. Nature Communications 9:2784 (2018).

Spirachuabwong C, Karuwan C, Wisitsorrat A, Phokharatkul D, Lomas T, Sritongkham P, & Tuantranont A, Inkjet-printed graphene-PEDOT: PSS modified screen printed carbon electrode for biochemical sensing. J Mater Chem 22:5478-5485 (2012).

Akhtar R, Sherratt M J, Cruickshank J K, & Derby B, Characterizing the elastic properties of tissues. Materials Today 14:96-105 (2011).

Patil A C & Thakor N V, Implantable neurotechnologies: a review of micro- and nanoelectrodes for neural recording. Medical & Biological Engineering & Computing 54:23-44 (2016).

Wang Y, et al., A highly stretchable, transparent, and conductive polymer. Science Advances 3:e1602076 (2017).

Yuk H, Zhang T, Lin S, Parada GA, & Zhao X, Tough bonding of hydrogels to diverse non-porous surfaces. Nature Materials 15:190-196 (2016).

Rutecki P A, Lebeda F J, & Johnston D, Epileptiform activity induced by changes in extracellular potassium in hippocampus. Journal of Neurophysiology 54:1363-1374 (1985).

Stringer J L & Lothman E W, Epileptiform discharges induced by altering extracellular potassium and calcium in the rat hippocampal slice. Experimental neurology 101:147-157 (1988).

Wenzel M, Hamm J P, Peterka D S, & Yuste R, Reliable and elastic propagation of cortical seizures in vivo. Cell Reports 19:2681-2693 (2017).

Nam J, et al., Supramolecular peptide hydrogel-based soft neural interface augments brain signals through a three-dimensional electrical network. ACS Nano 14:664-675 (2020).

Cook M, et al., Anti-seizure therapy with a long-term, implanted intra-cerebroventricular delivery system for drug-resistant epilepsy: A first-in-man study. EClinical Medicine 22:100326 (2020).

Pirozzi C, et al., Butyrate prevents valproate—induced liver injury: In vitro and in vivo evidence. The FASEB Journal 34:676-690 (2020).

Feig V R, Tran H, Lee M, & Bao Z, Mechanically tunable conductive interpenetrating network hydrogels that mimic the elastic moduli of biological tissue. Nature Communications 9:1-9 (2018).

Deng Z, Guo Y, Zhao X, Ma PX, & Guo B, Multifunctional stimuli-responsive hydrogels with self-healing, high conductivity, and rapid recovery through host-guest interactions. Chem Mater 30:1729-1742 (2018).

Shi Y, Ma C, Peng L, & Yu G, Conductive "smart" hybrid hydrogels with PNIPAM and nanostructured conductive polymers. Adv Funct Mater 25:1219-1225 (2015).

Zhao X, Chen X, Yuk H, Lin S, Liu X, & Parada G, Soft materials by design: unconventional polymer networks give extreme properties. Chemical Reviews 121:4309-4372 (2021).

Zeglio E, Rutz A L, Winkler T E, Malliaras G G, & Herland A, Conjugated polymers for assessing and controlling biological functions. Advanced Materials 31:e1806712 (2019).

Amorini F, et al., Electrically controlled "sponge effect" of PEDOT:PSS governs membrane potential and cellular growth. ACS Applied Materials & Interfaces 9:6679-6689 (2017).

Jonsson A, Song Z, Nilsson D, Meyerson BA, Simon DT, Linderoth B, & Berggren M, Therapy using implanted organic bioelectronics. Science Advances 1:e1500039 (2015).

Kim C Y, et al., Soft subdermal implant capable of wireless battery charging and programmable controls for applications in optogenetics. Nature communications 12:1-13 (2021).

Park Y, et al., Three-dimensional, multifunctional neural interfaces for cortical spheroids and engineered assembloids. Science Advances 7:eabf9153 (2021).

Won S M, Song E, Reeder J T, & Rogers J A, Emerging modalities and implantable technologies for neuromodulation. Cell 181:115-135 (2020).

Li Z, Song N, & Yang Y—W, Stimuli-responsive drug-delivery systems based on supramolecular nanovalves. Matter 1:345-368 (2019).

A. Berenyl et al, 10 Aug. 2012, Science, Vol 337, 735-737

C. M. Proctor et al, 29 Aug. 2018, Science Advances, 4:eaau1291 1-8

H. Joo, et al, 1 Jan. 2021, Sciences Advances, 7:eabd4639 1-12

J. C. Sanchez, et al, 12 Feb. 2021, U.S. Pat. No. 8,374,696B2

What is claimed is:

1. A composition for the manufacture of a hydrogel material, consisting essentially of:

N-(3-Sulfopropyl)-N-methacroyloxyethyl-N,N-dimethyl-ammonium betaine (DMAPS) serving as a backbone of the hydrogel material, poly(3,4-ethylenedioxythiophene) polystyrene sulfonate (PEDOT:PSS) serving as a conductive component, at least one crosslinking agent, a photo-initiator, and a photo-initiator auxiliary element, wherein:

the crosslinking agent is a compound provided with acryloyl groups as terminal groups, and wherein the crosslinking agent includes a covalent crosslinker of N, N'-methylenebisacrylamide (MBA) and a physical cross-linker of diacrylate functionalized poly(ethylene glycol)-b-poly(propylene glycol)-b-poly(ethylene glycol), the photo-initiator and the photo-initiator auxiliary element facilitate crosslinking of the DMAPS and the PEDOT:PSS in the hydrogel material, the photo-initiator auxiliary element is selected from the group consisting of lithium phenyl-2,4,6-trimethylbenzoylphosphinate (LAP), 2-isopropylthioxanthone (ITX), 2-(4-methylbenzyl)-2-(dimethyamino)-1-(4-morpholinophenyl)butan-1-one, phenylbis(2,4,6-trimethylbenzoyl)phosphine oxide, 2-methyl-4'-(methyl-thio)-2-morpholinopropiophenone and diphenyl(2,4,6-trimethylbenzoyl)phosphine oxide (TPO), and said composition is configured to undergo photo-cross-linking in the presence of light and said photo-initiator auxiliary system".

2. A composition as claimed in claim 1, wherein the photo-initiator is or includes 2-hydroxy-4'-(2-hydroxy-ethoxy)-2-methylpropiophenone.

3. A composition as claimed in claim 1, comprising a catalyst, wherein the catalyst is ammonium persulfate.

4. A hydrogel material comprising an interpenetrating structure of:

N-(3-Sulfopropyl)-N-methacroyloxyethyl-N,N-dimethyl-ammonium betaine (DMAPS) serving as a backbone of the hydrogel material, poly(3,4-ethylenedioxythiophene) polystyrene sulfonate (PEDOT:PSS) serving as a conductive component, and at least one crosslinking agent linking the DMAPS and the PEDOT:PSS together in the hydrogel material forming a network of polymerized PEDOT:PSS and PEDOT:PSS (DMA/PEDOTS), wherein:

the crosslinking agent is or includes a compound provided with acryloyl groups as terminal groups, and wherein the crosslinking agent is selected from the group consisting of N, N'-methylenebisacrylamide (MBA) and, diacrylate functionalized poly(ethylene glycol)-b-poly (propylene glycol)-b-poly(ethylene glycol), a photo-initiator and a photo-initiator auxiliary element for assisting the photo-crosslinking of the DMAPS and the PEDOT:PSS by the crosslinking agent, the photo-initiator auxiliary element is selected from the group consisting of lithium phenyl-2,4,6-trimethylbenzoylphosphinate (LAP), 2-isopropylthioxanthone (ITX), 2-(4-methylbenzyl)-2-(dimethyamino)-1-(4-morpholinophenyl)butan-1-one, phenylbis(2,4,6-trimethylbenzoyl)phosphine oxide, 2-methyl-4'-(methyl-thio)-2-morpholinopropiophenone and diphenyl(2,4,6-trimethylbenzoyl)phosphine oxide (TPO).

5. A hydrogel material as claimed in claim 4, wherein the content of the DMAPS in the hydrogel material is 5-60 wt %, and the content of the PEDOT:PSS in the hydrogel material is 0.01-20 wt %.

6. A hydrogel material as claimed in claim 4, wherein the photo-initiator is or includes 2-hydroxy-4'-(2-hydroxy-ethoxy)-2-methylpropiophenone.

7. A hydrogel material as claimed in claim 4, comprising ammonium persulfate and/or N,N,N',N'-tetramethylethyl-enediamine as a catalyst.

8. A composition as claimed in claim 1, wherein the composition is configured within a microneedle array including a plurality of independently addressable electrodes, each of which is capable of recording electrophysiological signals and releasing a pre-loaded therapeutic agent in response to electrical stimulation.

* * * * *